United States Patent [19]

Dumas

[11] Patent Number: 4,661,147
[45] Date of Patent: Apr. 28, 1987

[54] HERBICIDAL SULFONAMIDES
[75] Inventor: Donald J. Dumas, Wilmington, Del.
[73] Assignee: E. I. Du Pont de Nemours and Company, Wilmington, Del.
[21] Appl. No.: 726,452
[22] Filed: Apr. 29, 1985

Related U.S. Application Data

[63] Continuation-in-part of Ser. No. 617,606, Jun. 5, 1984, abandoned.
[51] Int. Cl.$^4$ .................... A01N 43/54; C07D 239/42
[52] U.S. Cl. ............................................ 71/92; 71/88; 71/90; 71/93; 71/96; 544/208; 544/209; 544/211; 544/212; 544/219; 544/253; 544/278; 544/310; 544/312; 544/317; 544/319; 544/320; 544/321; 544/327; 544/331; 544/332; 548/263; 548/268
[58] Field of Search ............... 544/332, 320, 321, 310, 544/312, 317, 319, 327, 331; 71/92

[56] References Cited

U.S. PATENT DOCUMENTS 4,370,480  1/1983  Levitt et al. .............................. 71/92
4,394,506  7/1983  Levitt ................................... 544/321

*Primary Examiner*—Glennon H. Hollrah
*Assistant Examiner*—James H. Turnipseed

[57] ABSTRACT

The invention relates to certain sulfonylurea compounds having an ester group ortho to the sulfonylurea linkage which have been found to be excellent preemergent and postemergent herbicides or plant growth regulators.

30 Claims, No Drawings

HERBICIDAL SULFONAMIDES

RELATED APPLICATION

This application is a continuation-in-part of my copending application U.S. Ser. No. 617,606 filed June 5, 1984 which is now abandoned.

BACKGROUND OF THE INVENTION

This invention relates to certain novel sulfonylurea compounds, agriculturally suited compositions thereof and their use as preemergent and postemergent herbicides or plant growth regulators.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

A number of different types of N-[(heterocyclic)aminocarbonyl]arylsulfonamides are known as herbicides.

U.S. Pat. No. 4,394,506 discloses sulfonylurea herbicides substituted on the benzene ring ortho to the sulfonylurea bridge.

U.S. Pat. No. 4,127,405 discloses sulfonylurea herbicides substituted ortho to the sulfonylurea segment.

U.S. Pat. No. 4,420,325 discloses sulfonylurea herbicides wherein the benzene ring is substituted ortho to the sulfonylurea substituent.

U.S. Pat. No. 4,383,113 discloses herbicidal ortho-carboalkoxybenzenesulfonylureas.

EP-A No. 30,142 published June 10, 1981 discloses herbicidal thiophene sulfonylureas substituted with alkoxycarbonyl groups.

EP-A No. 70,698 published Jan. 26, 1983 discloses herbicidal indole sulfonylureas.

Herbicidal pyrazole sulfonylureas are disclosed in EP-A-No. 95,925 published Dec. 7, 1983 and EP-A-No. 87,780 published Sept. 7, 1983.

The current population explosion and concomitant world food and fiber shortage demand improvement in the efficiency of producing these crops. Preventing or minimizing loss of valuable crops by killing or inhibiting the growth of undesired vegetation is one way of improving this efficiency. Even though there are a wide variety of products useful for killing and inhibiting growth of undesired vegetation the need still exists for more effective herbicides.

SUMMARY OF THE INVENTION

Now new compounds and compositions thereof have been found that are preemergent or postemergent herbicides or plant growth regulators. The compounds of the invention are of the formula I

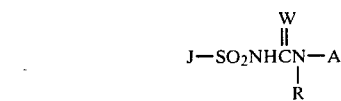

wherein
J is

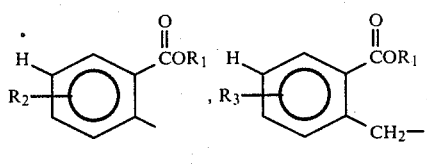

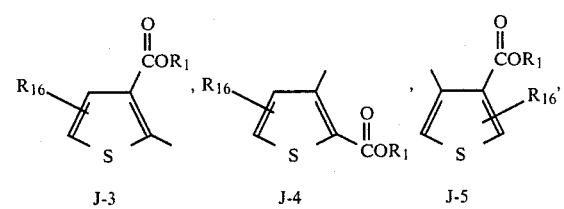

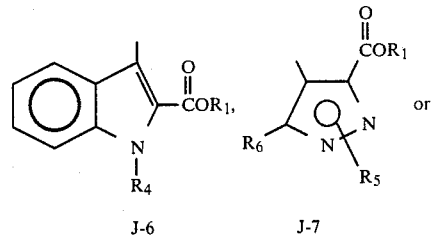

or

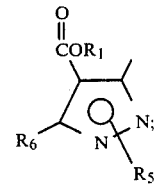

W is O or S;
R is H or CH$_3$;
R$_1$ is C$_2$–C$_5$ alkyl, C$_4$ alkenyl or C$_4$ alkynyl substituted with one or two substituents selected from:

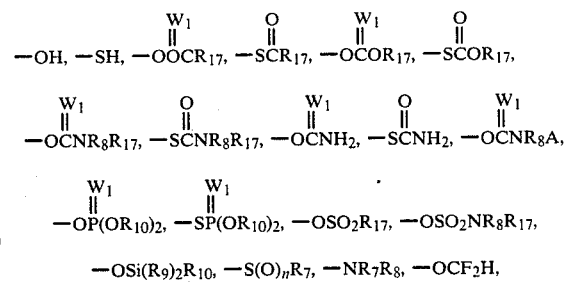

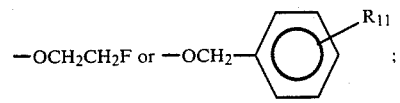

provided that (1) when $R_1$ is disubstituted, then the two substituents are identical and are not on the same carbon atom;
(2) when $R_1$ is $C_2$-$C_3$ alkyl and monosubstituted, then the substituent is other than $-SR_7$ or $-SO_2R_7$; and
(3) the carbon atom of $R_1$ adjacent to the ester oxygen does not carry any of the above substituents and must be substituted by at least one hydrogen atom;

$W_1$ is O or S;
n is 0, 1, or 2;
$R_2$ is H, Cl, F, Br, $C_1$-$C_3$ alkyl, $C_1$-$C_3$ alkoxy, $C_1$-$C_3$ alkylthio, $C_1$-$C_3$ haloalkoxy, $C_1$-$C_3$ haloalkylthio, $C_1$-$C_2$ haloalkyl, or $C_1$-$C_2$ alkyl substituted with $OCH_3$ or $SCH_3$;
$R_3$ is H, F, Cl, $CH_3$ or $OCH_3$;
$R_4$ is H or $CH_3$;
$R_5$ is H, $C_1$-$C_3$ alkyl, $CH_2CH=CH_2$ or phenyl;
$R_6$ is H or $C_1$-$C_3$ alkyl;
$R_7$ is $C_1$-$C_4$ alkyl substituted with 0-3 atoms of F, Cl or Br, 0-2 methoxy groups or 0-1 cyano groups, $C_3$-$C_4$ alkenyl substituted with 0-3 atoms of F, Cl or Br, $C_3$-$C_4$ alkynyl or

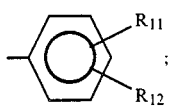

$R_8$ is H or $C_1$-$C_2$ alkyl;
$R_9$ is $C_1$-$C_2$ alkyl;
$R_{10}$ is $C_1$-$C_4$ alkyl or $C_6H_5$;
$R_{11}$ and $R_{12}$ are independently H, F, Cl, Br, $CH_3$, $OCH_3$, $SCH_3$, $SO_2CH_3$, $NO_2$ or $CF_3$;
A is

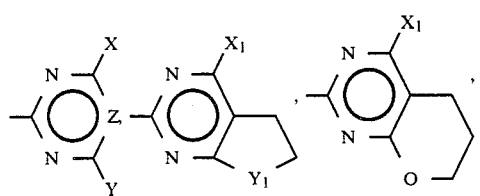

A-1   A-2   A-3

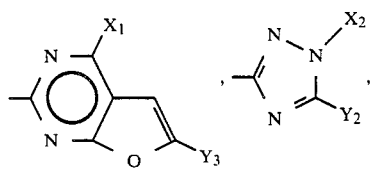

A-4   A-5

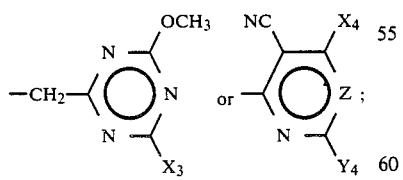

A-6   A-7

X is $CH_3$, $OCH_3$, $OCH_2CH_3$, Cl, F, Br, $OCF_2H$, $CH_2F$, $OCH_2CH_2F$, $OCH_2CHF_2$, $OCH_2CF_3$ or $CF_3$;
Y is H, $CH_3$, $OCH_3$, $OC_2H_5$, $CH_2OCH_3$, $NHCH_3$, $N(OCH_3)CH_3$, $NH_2$, $N(CH_3)_2$, $C_2H_5$, $CF_3$, $SCH_3$, $OCH_2CH=CH_2$, $OCH_2C\equiv CH$, $OCH_2CH_2OCH_3$,

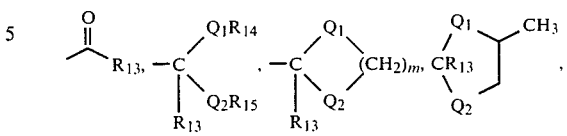

$OCF_2H$, $SCF_2H$, $CH_2S(O)_p(C_1$-$C_4$ alkyl), cyclopropyl or $CH_2OC_2H_5$;
m is 2 or 3;
p is 0, 1 or 2;
$Q_1$ and $Q_2$ are independently O or S;
$R_{13}$ is H or $CH_3$;
$R_{14}$ and $R_{15}$ are independently $C_1$-$C_2$ alkyl;
$R_{16}$ is H, F, Cl or $CH_3$;
$R_{17}$ is $C_1$-$C_{10}$ alkyl substituted with 0-3 atoms of F, Cl or Br, 0-2 methoxy groups or 0-1 cyano groups, $C_3$-$C_{10}$ alkenyl substituted with 0-3 atoms of F, Cl or Br, $C_3$-$C_{10}$ alkynyl substituted with 0-3 atoms of F, Cl or Br, or

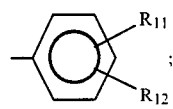

Z is CH or N;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$Y_3$ is H or $CH_3$;
$X_3$ is $CH_3$ or $OCH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
provided that
(a) when W is S, then R is H,
A is

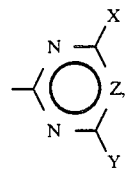

and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CF_3$, $OCH_2CH_2OCH_3$, $CH(OCH_3)_2$ or

(b) when X is Cl, F or Br, then Z is CH and Y is $OCH_3$, $OC_2H_5$, $NH_2$, $N(OCH_3)CH_3$, $NHCH_3$, $N(CH_3)_2$ or $OCF_2H$; and
(c) when X or Y is $OCF_2H$, then Z is CH;
and their agriculturally suitable salts.

Compounds of the invention which are preferred for their higher herbicidal activity, greater plant growth regulant activity and/or more favorable ease of synthesis are:

(1) Compounds of Formula I wherein W is O; R is H; $R_1$ is monosubstituted $C_2$–$C_5$ alkyl; $R_7$ is $CH_3$, $C_2H_5$, $C_3$ alkenyl or $C_3$ alkynyl; $R_9$ is $CH_3$; $R_{10}$ is $CH_3$; and $R_{17}$ is $C_1$–$C_4$ alkyl substituted with 0–3 atoms of F, Cl or Br, 0–2 methoxy groups or 0–1 cyano group, $C_3$–$C_4$ alkenyl substituted with 0–3 atoms of F, Cl or Br or $C_3$–$C_4$ alkynyl.

(2) Compounds of Preferred 1 wherein A is A-1; $R_2$ is H, F, Cl, $CH_3$, $OCH_3$, $OC_2H_5$, $SCH_3$, $SC_2H_5$, $CH_2OCH_3$ or $CF_3$; $R_6$ is H; $R_{16}$ is H; and Y is $CH_3$, $C_2H_5$, $OCH_3$, $OC_2H_5$, $CH_2OCH_3$, $CH_2OC_2H_5$, $NHCH_3$, $N(CH_3)_2$, cyclopropyl, $CH(OCH_3)_2$ or

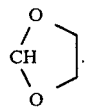

(3) Compounds of Preferred 2 wherein $R_{17}$ is $CH_3$, $C_2H_5$ or $CH_2CH=CH_2$; $W_1$ is O; and $R_1$ is monosubstituted $C_2$–$C_3$ alkyl.
(4) Compounds of Preferred 3 wherein J is J-1 and $R_2$ is H.
(5) Compounds of Preferred 3 wherein J is J-2.
(6) Compounds of Preferred 3 wherein J is J-3.
(7) Compounds of Preferred 3 wherein J is J-4.
(8) Compounds of Preferred 3 wherein J is J-5.
(9) Compounds of Preferred 3 wherein J is J-6.
(10) Compounds of Preferred 3 wherein J is J-7.
(11) Compounds of Preferred 3 wherein J is J-8.
(12) Compounds of Preferred 3 wherein X is $CH_3$, $OCH_3$, $OC_2H_5$, Cl, Br, $OCHF_2$ or $CF_3$; and Y is $CH_3$, $OCH_3$, $NHCH_3$ or $CH(OCH_3)_2$.

The compound of the invention which is specifically preferred for reasons of its highest herbicidal activity, greatest plant growth regulant activity and/or most favorable ease of synthesis is: 2-[[(4,6-dimethylpyrimidin-2-yl)aminocarbonyl]aminosulfonyl]benzoic acid, 2-hydroxyethyl ester, m.p. 110°–113° C.

DETAILED DESCRIPTION OF THE INVENTION

Synthesis

Compounds of Formula I can be prepared by one or more of the procedures shown in Equations 1, 5, and 6. J, W, R, and A are as previously defined.

Equation 1

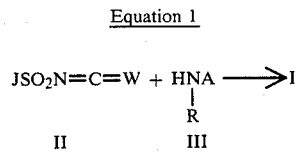

The reaction of Equation 1 is best carried out in an inert aprotic organic solvent such as dichloromethane, 1,2-dichloroethane, tetrahydrofuran, or acetonitrile, at a temperature between 20° and 85° C. The order of addition is not critical; however, it is often convenient to add the sulfonyl isocyanate (or isothiocyanate), or a solution of it in the reaction solvent, to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtation, by recrystallization from mixtures of solvents such as 1,2-dichloroethane, 1-chlorobutane and heptane or by chromatography on silica gel.

Sulfonylisocyanates (II, W is O) are known in the art and are prepared from the corresponding sulfonamides (IV) by one of the following two general methods.

Equation 2

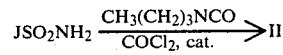

The sulfonamide IV and an alkyl isocyanate (e.g., n-butyl isocyanate) in xylene or other solvent boiling above 135° C. are mixed in the presence or absence of a catalytic amount of 1,4-diaza[2.2.2]bicyclooctane (DABCO) and heated to 135°–140° C. After 5–60 minutes phosgene is slowly added to the heated mixture at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (II).

If desired, the alkyl isocyanate-sulfonamide adduct can be made and isolated before reaction with the phosgene. In this case the sulfonamide (IV), alkyl isocyanate, and anhydrous base (e.g, $K_2CO_3$) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful when sulfonamide (IV) is high melting and has low solubility in the phosgenation solvent.

Sulfonyl isocyanates (II) can also be prepared by the following method.

Equation 3

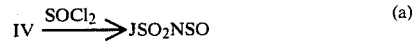

The sulfonamide (IV) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (V) (Equation 3a).

The thionyl chloride is evaporated and the residue is treated with an inert solvent (e.g. toluene) containing at least one equivalent (typically 2–3 equivalents) of phosgene. A catalytic amount of pyridine (typically 0.1 equivalent) is added, and the mixture is heated to about 60°–140° C., with 80°–100° preferred. Conversion to the isocyanate (II) is usually substantially complete within 15 minutes to 3 hours (Equation 3b). The mixture is then cooled and filtered, and the solvent is evaporated, leaving the sulfonyl isocyanate (II).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in *Arch. Pharm.* 299, 174 (1966).

Equation 4

$$IV \xrightarrow{CS_2}{KOH} JSO_2N=C\begin{matrix}SK\\SK\end{matrix} \quad (a)$$

VI $$VI \xrightarrow{COCl_2} II \quad (b)$$

Many of the compounds of Formula I can be prepared by the procedure shown in Equation 5.

Equation 5

$$JSO_2NH\overset{W}{\underset{\|}{C}}OC_6H_5 + III \longrightarrow I$$

VII

The reaction of Equation 5 is carried out by contacting phenylcarbamates or phenylthiocarbamates of Formula VII with aminoheterocycles of Formula III in an inert organic solvent such as dioxane or tetrahydrofuran at temperatures of about 20°-100° C. for a period of about one-half to twenty-four hours. The product can be isolated by evaporation of the reaction solvent and purified by methods previously described.

Phenylcarbamates and phenylthiocarbamates of Formula VII can be prepared by the methods described, or modifications thereof known to those skilled in the art, in U.S. Pat. No. 4,443,243.

Alternatively, many of the compounds of Formula I can be prepared by the method described in Equation 6.

Equation 6

$$IV + C_6H_5O\overset{W}{\underset{\|}{C}}N\underset{R}{A} \longrightarrow I$$

VIII

The reaction of Equation 6 can be carried out by contacting equimolar amounts of a sulfonamide of Formula IV with a heterocyclic phenylcarbamate or phenylthiocarbamate of Formula VIII in the presence of a base such as 1,8-diazabicyclo[5.4.0]undec-7-ene (DBU), by methods analogous to those described in South African Patent Application 830441. The phenylcarbamates and phenylthiocarbamates of Formula VIII can be prepared by methods, or modifications thereof known to those skilled in the art, described in South African Patent Application No. 825671 and South African Patent Application No. 825045.

The sulfonamides of Formula IV can be prepared as shown in Equation 7.

Equation 7

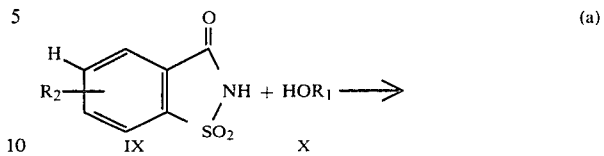
(a)

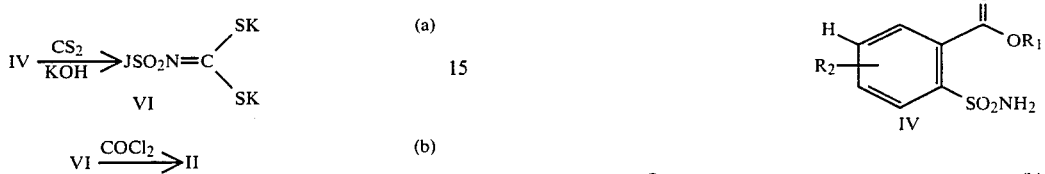
(b)

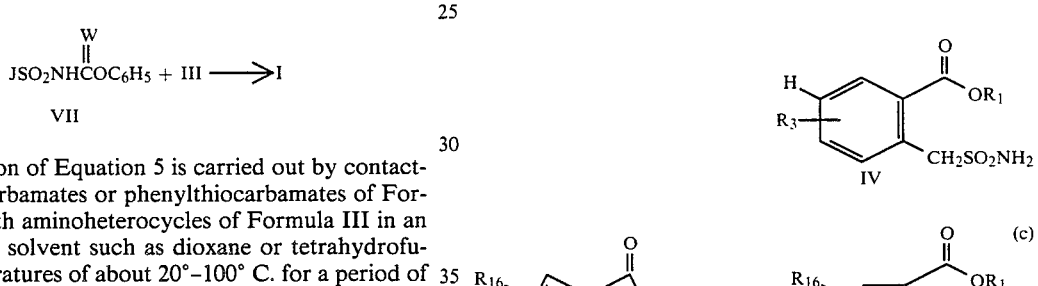

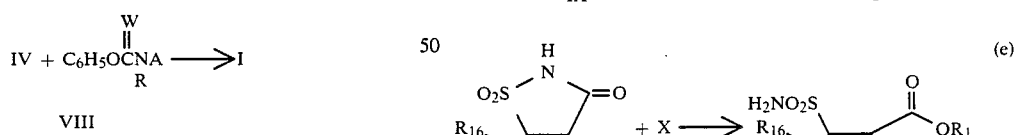

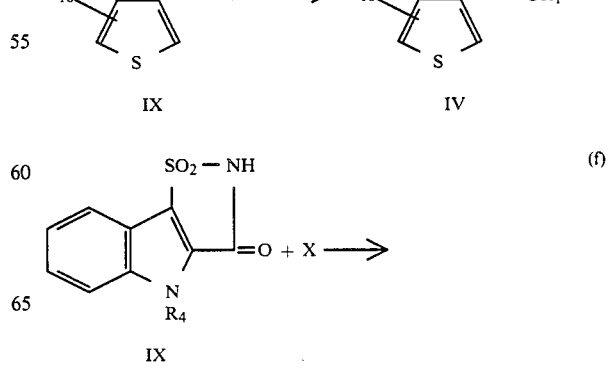

-continued
Equation 7

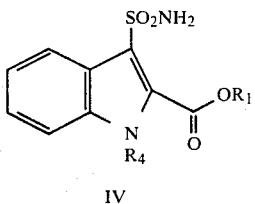

IV

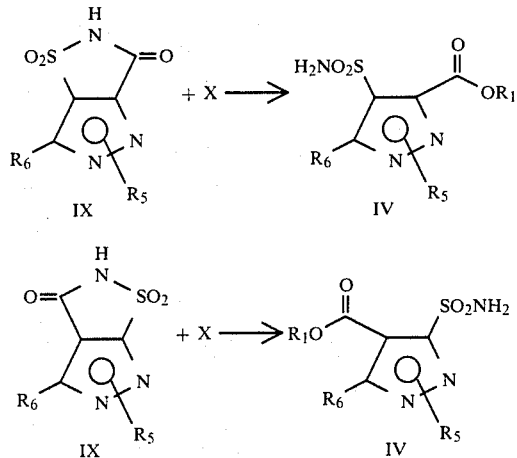

Treatment of a condensed isothiazole-3(2H)-one-1,1-dioxide of Formula IX or a condensed 1,2-thiazine-3(2H)-one-1,1-dioxide of Formula XI with an appropriately substituted alcohol in the presence of an acid catalyst such as hydrogen chloride or para-toluenesulfonic acid gives sulfonamides IV. The reaction may be carried out at ambient to reflux temperature using excess alcohol as the solvent or in an inert solvent such as toluene or xylene.

The alcohols of Formula X are known or can be prepared by methods known in the art. In cases where $R_1$ is substituted with

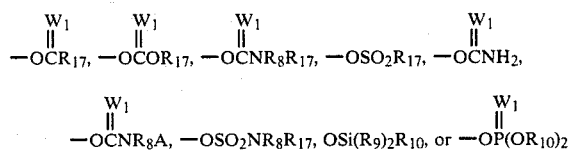

it is often more convenient to first prepare the corresponding sulfonamides (of Formula IV), sulfonylureas, or sulfonylthioureas (of Formula I) in which $R_1$ is substituted with one or two hydroxy groups. The hydroxy group (or groups) can then be functionalized to give the desired derivatives using methods which are well known in the art.

In the same way, when $R_1$ is substituted with

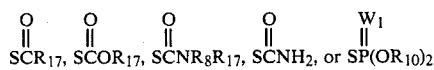

it is often more convenient to first prepare the corresponding sulfonamides (of Formula IV), sulfonylureas, or sulfonylthioureas (of Formula I) in which $R_1$ is substituted with one or two mercapto groups. The mercapto group (or groups) can then be functionalized to give the desired derivatives using methods which are well known in the art.

It is expected that any derivative of an alcohol or thiol which is converted to the alcohol or thiol in a spray solution, on the plant surface, in plant tissue, or in the soil will give an effective herbicide when incorporated as a substituent on $R_1$.

When $R_1$ is substituted with one or two

groups it is expected that derivatives wherein A is a heterocycle other than those described herein will also be effective herbicides.

When $R_1$ is substituted with one or two $S(O)_nR_7$ groups and n is equal to 1 or 2, the sulfonamides (of Formula IV), sulfonylureas and sulfonylthioureas (of Formula I) may also be prepared from the corresponding compounds in which n is equal to 0 by contact with an oxiding agent such as hydrogen peroxide or meta-chloroperbenzoic acid. The level of oxidation may be controlled by the amount of oxidant used and by the reaction temperture according to procedures which are known in the art.

Condensed isothiazole-3(2H)-one-1,1-dioxides of Formula IX and condensed 1,2-thiazine-3(2H)-one-1,1-dioxides of Formula XI are known or can be prepared by methods known in the art as shown in Equation 8.

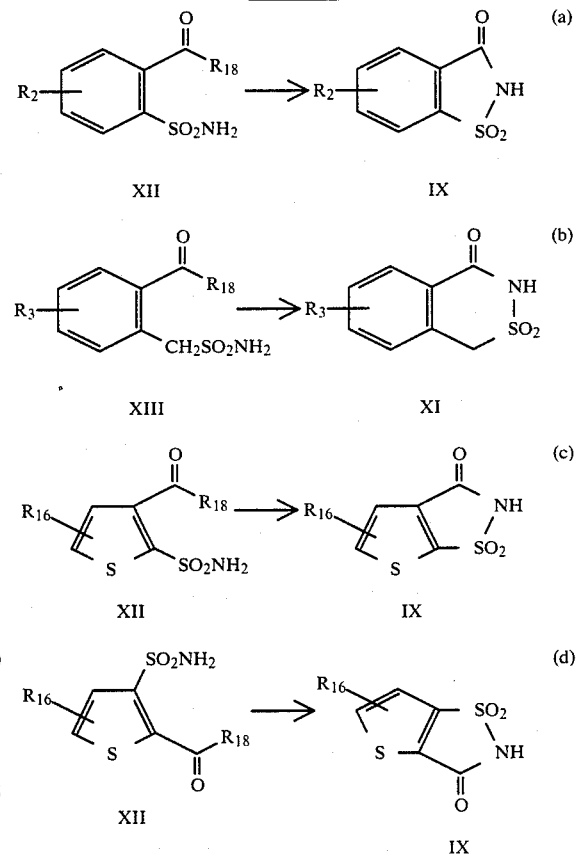

-continued

Equation 8

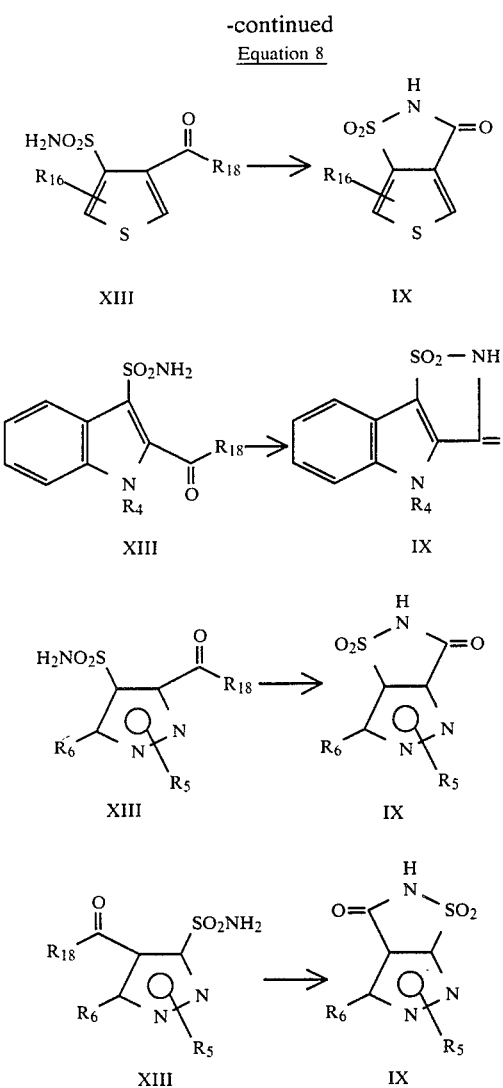

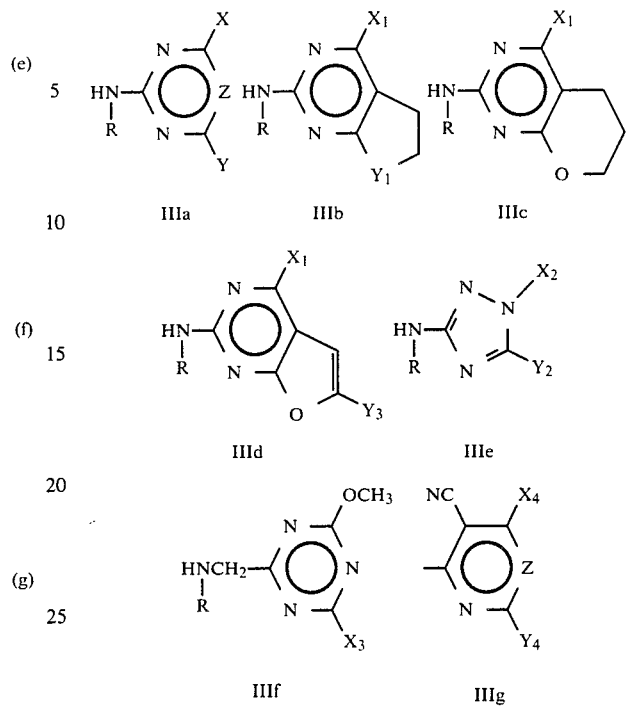

Sulfonamides of Formulas XII and XIII where $R_{18}$ is a displaceable substituent such as alkoxy, aryloxy, halo, or hydroxy are cyclized to compounds of Formulas IX and XI under a variety of acidic and basic conditions (including those found in U.S. Pat. No. 4,430,355 (1984).

The sulfonamides of Formula XII and XIII can be prepared by methods which are known in the art. The benzenesulfonamides are disclosed in U.S. Pat. No. 4,394,506 (1983). The benzylsulfonamides are disclosed in U.S. Pat. No. 4,420,325 (1983). The thiophenesulfonamides are disclosed in European Patent Application No. 30,142 (published June 10, 1981). The indolesulfonamides are disclosed in European Patent Application No. 70,698 (published Jan. 26, 1983). The pyrazolesulfonamides are disclosed in European Patent Application No. 87,780 (published Sept. 7, 1983).

The heterocyclic amines of Formulae IIIa–IIIg below are either known or can be prepared by obvious methods by one skilled in the art.

For a review of the synthesis and reactions of 2-amino- and 2-methylaminopyrimidines IIIa (Z=CH) see *The Chemistry of Heterocyclic Compounds*, Vol. 16, Wiley-Interscience, New York (1962). For a review of the synthesis and reactions 2-amino- and 2-methylamino-s-triazines IIIa (Z=N) see *The Chemistry of Heterocyclic Compounds*, Vol. 13, Wiley-Interscience, New York (1959), F. C. Schaefer, U.S. Pat. No. 3,154,537 and F. C. Schaefer and K. R. Huffman *J. Org. Chem.*, 28, 1812 (1963). The synthesis of the bicyclic amines IIIb and IIIc is taught in U.S. Pat. No. 4,339,267. The synthesis of bicyclic amines IIId is taught in U.S. Pat. No. 4,487,626. The preparation of aminomethyltriazines IIIf is taught in U.S. Pat. No. 4,496,392. The preparation off cyanopyridines and cyanopyrimidines IIIg is taught in European Publication No. 125,864 (published Nov. 21, 1984).

The amines of Formula III where X or $X_1$ Is $OCF_2H$ and/or Y is $OCF_2H$ or $SCF_2H$ can be prepared by methods taught in South African Patent Application No. 825,045, or by suitable modifications that would be obvious to one skilled in the art.

The pyrimidines of Formula IIIa (Z=CH) where Y is

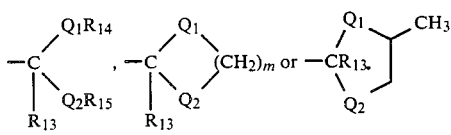

can be prepared according to the methods taught in European Patent Application No. 82306492.8 (Publication No. 84,224) or suitable modifications thereof known to one skilled in the art.

The triazoles of Formula IIIe can be prepared according to the methods taught in U.S. Pat. No. 4,421,550.

EXAMPLE 1

2-Aminosulfonylbenzoic acid, 2-hydroxyethyl ester

Hydrogen chloride gas was passed through a mixture of 54.9 g of saccharin and 500 ml of ethylene glycol for 1½ hours. The mixture, which had warmed to 41° C., was then stirred at ambient temperature for 65 hours. The resulting solution was poured into 2 liters of ice water and the product extracted with ethyl acetate. The extracts were washed with water, dried (MgSO$_4$), and the solvent removed under reduced pressure to give a colorless oil which slowly crystallized. The white solid was triturated with n-butylchloride to give 44.9 g of the title compound, m.p. 84°–86.5° C.

IR (neat) 1720 cm$^{-1}$ (ester):

NMR (CDCl$_3$/DMSO-d$_6$)δ: 3.8 (m, 2H, CH$_2$OH); 4.4 (m, 2H, CO$_2$CH$_2$—); 5.15 (br, 1H, OH); 7.2 (br s, 2H, NH$_2$); and 7.6–8.2 (m, 4H, aromatics).

EXAMPLE 2

2-Aminosulfonfylbenzoic acid, 2-trimethylsilyloxyethyl ester

To a slurry of 12.25 g of 2-aminosulfonylbenzoic acid, 2-hydroxyethyl ester, 125 ml of dry methylene chloride, and 7.7 ml of triethylamine was added dropwise over 10 minutes 6.3 ml of trimethylsilyl chloride (exotherm to 36° C.). The resulting solution was allowed to stand at ambient temperature for 18 hours and then washed with saturated sodium chloride solution, dried (MgSO$_4$), and the solvent removed under reduced pressure to give an oil which was chromatographed on silica gel eluting with 25% EtOAc:hexane to give a colorless oil which slowly crystallized. Trituration with hexane gave 8.0 g of white crystals, m.p. 72°–76° C.

IR (nujol) 1738 cm$^{-1}$ (ester).

NMR (CDCl$_3$)δ: 0.1 (s, 9H, Si(CH$_3$)$_3$); 3.9 (m, 2H, —CH$_2$OSiMe$_3$); 4.4 (m, 2H, CO$_2$CH$_2$—); 5.95 (br s, 2H, NH$_2$); and 7.4–8.2 (m, 4H, aromatics).

EXAMPLE 3

2-[[(4,6-dimethylpyrimidin-2-yl)aminocarbonyl-]aminosulfonyl]benzoic acid, 2-hydroxyethyl ester

Method A

To a solution of 0.49 g of 2-aminosulfonylbenzoic acid, 2-hydroxyethyl ester and 0.49 g of 4,6-dimethylpyrimidin-2-yl-carbamic acid, phenyl ester in 10 ml of dry acetonitrile was added 0.30 ml of 1,8-diazabicyclo[5.4.0]undec-7-ene (DBU). After stirring for 2 hours at ambient temperature the solution was diluted with 10 ml of water and acidified to pH 2 with 5% HCl. The solvent was removed under reduced pressure and the wet residue triturated with n-butyl chloride to give a white solid which was collected, washed thoroughly with n-butyl chloride and dried in vacuo. 0.6 g, m.p. 103°–107° C.(dec).

Method B

To a solution of 0.64 g of 2-aminosulfonylbenzoic acid, 2-trimethylsilyloxyethyl ester and 0.49 g of 4,6-dimethylpyrimidin-2-yl-carbamic acid, phenyl ester in 20 ml of acetonitrile was added 0.30 ml of DBU. After ½ hour the solvent was removed under reduced pressure, the residue dissolved in 25 ml of methylene chloride, washed with 5% NH$_4$Cl, dried (MgSO$_4$), and the solvent removed under reduced pressure. The residue was triturated with ether to give 0.46 g of white solid, m.p. 102°–106° C.(dec). The NH$_4$Cl wash was acidified to pH 1 with 5% HCl. extracted with methylene chloride, dried (MgSO$_4$), and the solvent removed under reduced pressure to give a white foam which was triturated with n-butylchloride to give an additional 0.23 g of the title compound, m.p. 110°–113° C.(d).

IR (nujol) 1730 cm$^{-1}$ (ester), 1715 cm$^{-1}$ (sulfonylurea).

NMR(CDCl$_3$)δ: 2.48 (s, 6H, CH$_3$'s); 3.96 (m, 2H, CH$_2$OH); 4.50 (m, 2H, CO$_2$CH$_2$—); 6.75 (s, 1H, pyr. C5—H); 7.66 (m, 3H, aromatics); 8.0 (br s, 1H, NH); 8.32 (m, 1H, aromatic); and 13.2 (br s, 1H, NH).

EXAMPLE 4

2-Aminosulfonylbenzoic acid, 2-methanesulfonyloxy ethyl ester

To a mixture of 12.25 g of 2-aminosulfonylbenzoic acid, 2-hydroxyethyl ester, 125 ml of dry methylene chloride, and 7.7 ml of triethylamine was added dropwise a solution of 3.9 ml of methanesulfonyl chloride in 25 ml of methylene chloride (exotherm to 37° C.). The resulting solution was allowed to stand for 18 hours and an additional 0.2 ml of methanesulfonyl chloride then added. After an additional 24 hours the reaction mixture was washed successively with water, 5% HCl, water, and saturated sodium chloride, dried (MgSO$_4$), and the solvent removed under reduced pressure to give a white solid which was triturated with n-butylchloride to give 8.0 g of the title compound, m.p. 124°–126° C.

IR (nujol) 1710 cm$^{-1}$ (ester).

NMR(CDCl$_3$)δ: 3.20 (s, 3H, OSO$_2$CH$_3$); 4.53 (s, 4H, —CH$_2$CH$_2$—); 7.3 (br s, 2H, NH$_2$); and 7.7–8.1 (m, 4H, aromatics).

EXAMPLE 5

2-[[(4,6-dimethoxypyrimidin-2-yl)aminocarbonyl-]aminosulfonyl]benzoic acid, 2-methanesulfonyloxy ester To a solution of 0.65 g of 2-aminosulfonylbenzoic acid, 2-methanesulfonyloxyethyl ester, 0.55 g of 4,6-dimethoxypyrimidin-2-yl-carbamic acid, phenyl ester and 10 ml of dry acetonitrile was added 0.30 ml of DBU. After 1 hour the solution was diluted with 10 ml of water and acidified to pH 1 with 5% HCl. The white solid precipitate was collected, washed with water and then with ether to give 0.52 g, m.p. 118°–120° C.(dec).

IR(nujol): 1730 cm$^{-1}$ (ester), 1708 cm$^{-1}$ (sulfonylurea).

NMR(CDCl$_3$)δ: 3.05 (s, 3H; OSO$_2$CH$_3$); 3.99 (s, 6H, OCH$_3$'s); 4.55 (m, 4H, —CH$_3$CH$_2$—); 5.80 (s, 1H, pyr. C5—H); 7.35 (br s, 1H, NH); 7.75 (m, 3H, aromatics); 8.50 (m, 1H, aromatic); and 12.63 (br s, 1H, NH).

Using the procedures and examples shown above, one skilled in the art can prepare the compounds in Tables 1–20.

TABLE 1

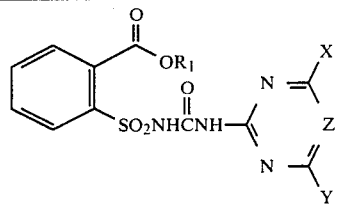

| R₁ | X | Y | Z | m.p. (°C.) |
|---|---|---|---|---|
| CH₂CH₂OH | CH₃ | CH₃ | CH | 110-113 (d) |
| CH₂CH₂OH | CH₃ | OCH₃ | CH | 97-100 (d) |
| CH₂CH₂OH | OCH₃ | OCH₃ | CH | 123-126 (d) |
| CH₂CH₂OH | Cl | OCH₃ | CH | 124-127 (d) |
| CH₂CH₂OH | Br | OCH₃ | CH | |
| CH₂CH₂OH | OCH₃ | OCF₂H | CH | |
| CH₂CH₂OH | CH₃ | OCF₂H | CH | |
| CH₂CH₂OH | OCF₂H | OCF₂H | CH | |
| CH₂CH₂OH | OCH₃ | OCH₂CH₃ | CH | |
| CH₂CH₂OH | OCH₃ | CH(OCH₃)₂ | CH | |
| CH₂CH₂OH | CF₃ | CF₃ | CH | |
| CH₂CH₂OH | OCH₂CH₂F | OCH₃ | CH | |
| CH₂CH₂OH | CH₃ | CH₂OCH₃ | CH | |
| CH₂CH₂OH | OCH₃ | CH₂OCH₃ | CH | |
| CH₂CH₂OH | OCH₂CH₂F | CH₃ | CH | |
| CH₂CH₂OH | CH₂F | OCH₃ | CH | |
| CH₂CH₂OH | CH₃ | CH₃ | N | 144-146 (d) |
| CH₂CH₂OH | CH₃ | OCH₃ | N | 140-143 (d) |
| CH₂CH₂OH | OCH₃ | OCH₃ | N | 137-139 (d) |
| CH₂CH₂OH | OCH₃ | OCH₂CH₃ | N | |
| CH₂CH₂OH | OCH₂CH₂F | OCH₃ | N | |
| CH₂CH₂OH | OCH₂CHF₂ | OCH₃ | N | |
| CH₂CH₂OH | OCH₂CF₃ | OCH₃ | N | |
| CH₂CH₂OH | OCH₂CF₃ | CH₃ | N | |
| CH₂CH₂OH | OCH₃ | NHCH₃ | N | |
| CH₂CH₂OH | OCH₃ | N(CH₃)₂ | N | |
| CH₂CH₂OH | OCH₂CH₂F | CH₃ | N | |
| CH₂CH₂OH | OCH₂CF₃ | CH₃ | N | |
| CH₂CH₂OH | CH₃ | OCH₂C≡CH | N | |
| CH₂CH(OH)CH₃ | CH₃ | CH₃ | CH | 110-112 (d) |
| CH₂CH(OH)CH₃ | CH₃ | OCH₃ | CH | 141-143 (d) |
| CH₂CH(OH)CH₃ | OCH₃ | OCH₃ | CH | 150-152 (d) |
| CH₂CH(OH)CH₃ | Cl | OCH₃ | CH | 147-149 (d) |
| CH₂CH(OH)CH₃ | Br | OCH₃ | CH | |
| CH₂CH(OH)CH₃ | OCH₃ | OCF₂H | CH | |
| CH₂CH(OH)CH₃ | CH₃ | OCF₂H | CH | |
| CH₂CH(OH)CH₃ | OCF₂H | OCF₂H | CH | |
| CH₂CH(OH)CH₃ | OCH₃ | OCH₂CH₃ | CH | |
| CH₂CH(OH)CH₃ | OCH₃ | CH(OCH₃)₂ | CH | |
| CH₂CH(OH)CH₃ | CF₃ | CF₃ | CH | |
| CH₂CH(OH)CH₃ | OCH₂CH₂F | OCH₃ | CH | |
| CH₂CH(OH)CH₃ | CH₃ | CH₂OCH₃ | CH | |
| CH₂CH(OH)CH₃ | OCH₃ | CH₂OCH₃ | CH | |
| CH₂CH(OH)CH₃ | OCH₂CH₂F | CH₃ | CH | |
| CH₂CH(OH)CH₃ | CH₂F | OCH₃ | CH | |
| CH₂CH(OH)CH₃ | CH₃ | CH₃ | N | |
| CH₂CH(OH)CH₃ | CH₃ | OCH₃ | N | 147-150 (d) |
| CH₂CH(OH)CH₃ | OCH₃ | OCH₃ | N | 142-144 (d) |
| CH₂CH(OH)CH₃ | OCH₃ | OCH₂CH₃ | N | |
| CH₂CH(OH)CH₃ | OCH₂CH₂F | OCH₃ | N | |
| CH₂CH(OH)CH₃ | OCH₂CHF₂ | OCH₃ | N | |
| CH₂CH(OH)CH₃ | OCH₂CF₃ | OCH₃ | N | |
| CH₂CH(OH)CH₃ | OCH₂CF₃ | CH₃ | N | |
| CH₂CH(OH)CH₃ | OCH₃ | NHCH₃ | N | |
| CH₂CH(OH)CH₃ | OCH₃ | N(CH₃)₂ | N | |
| CH₂CH(OH)CH₃ | OCH₂CH₂F | CH₃ | N | |
| CH₂CH(OH)CH₃ | OCH₂CF₃ | CH₃ | N | |
| CH₂CH(OH)CH₃ | CH₃ | OCH₂C≡CH | N | |
| CH(CH₃)CH₂OH | CH₃ | CH₃ | CH | |
| CH(CH₃)CH₂OH | CH₃ | OCH₃ | CH | |
| CH(CH₃)CH₂OH | OCH₃ | OCH₃ | CH | |
| CH(CH₃)CH₂OH | Cl | OCH₃ | CH | |
| CH(CH₃)CH₂OH | Br | OCH₃ | CH | |
| CH(CH₃)CH₂OH | CH₃ | OCF₂H | CH | |
| CH(CH₃)CH₂OH | OCH₃ | OCF₂H | CH | |
| CH(CH₃)CH₂OH | OCF₂H | OCF₂H | CH | |
| CH(CH₃)CH₂OH | OCH₃ | CH(OCH₃)₂ | CH | |
| CH(CH₃)CH₂OH | CH₃ | CH₃ | N | |
| CH(CH₃)CH₂OH | CH₃ | OCH₃ | N | |
| CH(CH₃)CH₂OH | OCH₃ | OCH₃ | N | |

TABLE 1-continued

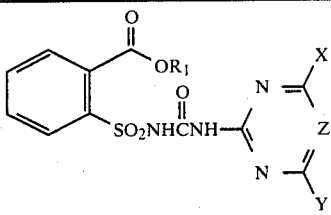

| R₁ | X | Y | Z | m.p. (°C.) |
|---|---|---|---|---|
| CH(CH₃)CH₂OH | OCH₂CF₃ | OCH₃ | N | |
| CH(CH₃)CH₂OH | OCH₂CH₃ | NHCH₃ | N | |
| CH₂CH₂CH₂OH | CH₃ | CH₃ | CH | 112–116 (d) |
| CH₂CH₂CH₂OH | CH₃ | OCH₃ | CH | 109–114 (d) |
| CH₂CH₂CH₂OH | OCH₃ | OCH₃ | CH | 139–141 (d) |
| CH₂CH₂CH₂OH | Cl | OCH₃ | CH | 127–131 (d) |
| CH₂CH₂CH₂OH | Br | OCH₃ | CH | |
| CH₂CH₂CH₂OH | CH₃ | OCF₂H | CH | |
| CH₂CH₂CH₂OH | OCH₃ | OCF₂H | CH | |
| CH₂CH₂CH₂OH | OCF₂H | OCF₂H | CH | |
| CH₂CH₂CH₂OH | OCH₃ | CH(OCH₃)₂ | CH | |
| CH₂CH₂CH₂OH | CH₃ | CH₃ | N | 147–148 (d) |
| CH₂CH₂CH₂OH | CH₃ | OCH₃ | N | 136–139 (d) |
| CH₂CH₂CH₂OH | OCH₃ | OCH₃ | N | 131–134 (d) |
| CH₂CH₂CH₂OH | OCH₂CF₃ | OCH₃ | N | |
| CH₂CH₂CH₂OH | OCH₂CH₃ | NHCH₃ | N | |
| CH₂CH(OH)CH₂CH₃ | CH₃ | CH₃ | CH | |
| CH₂CH(OH)CH₂CH₃ | CH₃ | OCH₃ | CH | |
| CH₂CH(OH)CH₂CH₃ | OCH₃ | OCH₃ | CH | |
| CH(CH₂OH)CH₂CH₃ | Cl | OCH₃ | CH | |
| CH(CH₂OH)CH₂CH₃ | Br | OCH₃ | CH | |
| CH(CH₂OH)CH₂CH₃ | CH₃ | OCF₂H | CH | |
| CH₂CH₂CH(OH)CH₃ | OCH₃ | OCF₂H | CH | |
| CH₂CH₂CH(OH)CH₃ | OCF₂H | OCF₂H | CH | |
| CH₂CH₂CH(OH)CH₃ | OCH₃ | CH(OCH₃)₂ | CH | |
| CH(CH₃)CH₂CH₂OH | CH₃ | CH₃ | N | |
| CH(CH₃)CH₂CH₂OH | CH₃ | OCH₃ | N | |
| CH(CH₃)CH₂CH₂OH | OCH₃ | OCH₃ | N | |
| CH₂CH₂CH₂CH₂OH | OCH₂CF₃ | OCH₃ | N | |
| CH₂CH₂CH₂CH₂OH | OCH₂CH₃ | NHCH₃ | N | |
| CH₂CH₂CH₂CH₂OH | CH₃ | OCH₃ | N | |
| CH₂CH(CH₃)CH₂OH | CH₃ | CH₃ | CH | |
| CH₂CH(CH₃)CH₂OH | CH₃ | OCH₃ | CH | |
| CH₂CH(CH₃)CH₂OH | OCH₃ | OCH₃ | CH | |
| CH₂CH(CH₃)CH₂OH | Cl | OCH₃ | CH | |
| CH₂CH(CH₃)₂OH | Br | OCH₃ | CH | |
| CH₂CH(OH)CH₂CH₂CH₃ | CH₃ | OCF₂H | CH | |
| CH₂CH(OH)CH₂CH₂CH₃ | OCH₃ | OCF₂H | CH | |
| CH₂CH(OH)CH₂CH₂CH₃ | OCF₂H | OCF₂H | CH | |
| CH₂CH(OH)CH₂CH₂CH₃ | OCH₃ | CH(OCH₃)₂ | CH | |
| CH(CH₂OH)CH₂CH₂CH₃ | CH₃ | CH₃ | N | |
| CH(CH₂OH)CH₂CH₂CH₃ | CH₃ | OCH₃ | N | |
| CH₂CH₂CH(OH)CH₂CH₃ | OCH₃ | OCH₃ | N | |
| CH₂CH₂CH(OH)CH₂CH₃ | OCH₂CF₃ | OCH₃ | N | |
| CH₂CH₂CH(OH)CH₂CH₃ | OCH₂CH₃ | NHCH₃ | N | |
| CH(CH₂CH₃)CH₂CH₂OH | CH₃ | CH₃ | CH | |
| CH(CH₂CH₃)CH₂CH₂OH | CH₃ | OCH₃ | CH | |
| CH(CH₂CH₃)CH₂CH₂OH | OCH₃ | OCH₃ | CH | |
| CH₂CH₂CH₂CH(OH)CH₃ | Cl | OCH₃ | CH | |
| CH₂CH₂CH₂CH(OH)CH₃ | Br | OCH₃ | CH | |
| CH₂CH₂CH₂CH(OH)CH₃ | CH₃ | OCF₂H | CH | |
| CH(CH₃)CH₂CH₂CH₂OH | OCH₃ | OCF₂H | CH | |
| CH(CH₃)CH₂CH₂CH₂OH | OCF₂H | OCF₂H | CH | |
| CH(CH₃)CH₂CH₂CH₂OH | OCH₃ | CH(OCH₃)₂ | CH | |
| CH₂C(CH₃)(OH)CH₂CH₃ | CH₃ | CH₃ | N | |
| CH₂CH(CH₃)CH(OH)CH₃ | CH₃ | OCH₃ | N | |
| CH₂CH(CH₃)CH(OH)CH₃ | OCH₃ | OCH₃ | N | |
| CH(CH₃)CH(CH₃)CH₂OH | OCH₂CF₃ | OCH₃ | N | |
| CH(CH₃)CH(CH₃)CH₂OH | OCH₂CH₃ | NHCH₃ | N | |
| CHCH(CH₃)CH₂CH₂OH | CH₃ | OCH₃ | N | |
| CHCH(CH₃)CH₂CH₂OH | CH₃ | CH₃ | CH | |
| CH₂CH₂CH(CH₃)CH₂OH | CH₃ | OCH₃ | CH | |
| CH₂CH₂CH(CH₃)CH₂OH | OCH₃ | OCH₃ | CH | |
| CH₂CH(CH₂OH)CH₂CH₃ | Cl | OCH₃ | CH | |
| CH₂CH(CH₂OH)CH₂CH₃ | Br | OCH₃ | CH | |
| CHC(CH₃)₂CH₂OH | CH₃ | OCF₂H | CH | |
| CHC(CH₃)₂CH₂OH | OCH₃ | OCF₂H | CH | |
| CH₂CH(CH₃)CH(OH)CH₃ | OCF₂H | OCF₂H | CH | |
| CH(CH₃)CH(CH₃)CH₂OH | OCH₃ | CH(OCH₃)₂ | CH | |
| CH₂CH(CH₃)CH₂CH₂OH | CH₃ | CH₃ | N | |

TABLE 1-continued

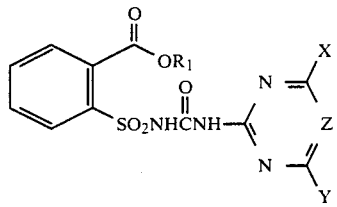

| R₁ | X | Y | Z | m.p. (°C.) |
|---|---|---|---|---|
| CH₂CH₂CH(CH₃)CH₂OH | CH₃ | OCH₃ | N | |
| CH₂CH(OH)CH(CH₃)₂ | OCH₃ | OCH₃ | N | |
| CH(CH₂OH)CH(CH₃)₂ | OCH₂CF₃ | OCH₃ | N | |
| CH₂CH₂CH(CH₃)CH₂OH | OCH₂CH₃ | NHCH₃ | N | |
| CH₂CH=CHCH₂OH | CH₃ | CH₃ | CH | |
| CH₂CH=CHCH₂OH | CH₃ | OCH₃ | CH | |
| CH₂CH=CHCH₂OH | OCH₃ | OCH₃ | CH | |
| CH₂CH(OH)CH=CH₂ | Cl | OCH₃ | CH | |
| CH₂CH(OH)CH=CH₂ | OCH₃ | CH(OCH₃)₂ | CH | |
| CH(CH₂OH)CH=CH₂ | CH₃ | OCH₃ | N | |
| CH(CH₂OH)CH=CH₂ | OCH₃ | OCH₃ | N | |
| CH₂C≡CCH₂OH | CH₃ | CH₃ | CH | |
| CH₂C≡CCH₂OH | CH₃ | OCH₃ | CH | |
| CH₂C≡CCH₂OH | OCH₃ | OCH₃ | CH | |
| CH₂CH(OH)C≡CH | Cl | OCH₃ | CH | |
| CH₂CH(OH)C≡CH | OCH₃ | CH(OCH₃)₂ | CH | |
| CH(CH₂OH)C≡CH | CH₃ | OCH₃ | N | |
| CH(CH₂OH)C≡CH | OCH₃ | OCH₃ | N | |
| CH₂CH₂OSO₂CH₃ | CH₃ | CH₃ | CH | 152-155 (d) |
| CH₂CH₂OSO₂CH₃ | CH₃ | OCH₃ | CH | 91-95 (d) |
| CH₂CH₂OSO₂CH₃ | OCH₃ | OCH₃ | CH | 118-120 (d) |
| CH₂CH₂OSO₂CH₃ | Cl | OCH₃ | CH | 96-100 (d) |
| CH₂CH₂OSO₂CH₃ | OCH₃ | CH(OCH₃)₂ | CH | |
| CH₂CH₂OSO₂CH₃ | CH₃ | OCH₃ | N | 151-153 (d) |
| CH₂CH₂OSO₂CH₃ | OCH₃ | OCH₃ | N | 141-151 (d) |
| CH₂CH₂CH₂OSO₂CH₃ | CH₃ | CH₃ | CH | 152-155 (d) |
| CH₂CH₂CH₂OSO₂CH₃ | CH₃ | OCH₃ | CH | 131-135 (d) |
| CH₂CH₂CH₂OSO₂CH₃ | OCH₃ | OCH₃ | CH | 103-106 (d) |
| CH₂CH₂CH₂OSO₂CH₃ | Cl | OCH₃ | CH | 136-138 (d) |
| CH₂CH₂CH₂OSO₂CH₃ | OCH₃ | CH(OCH₃)₂ | CH | |
| CH₂CH₂CH₂OSO₂CH₃ | CH₃ | OCH₃ | N | 151-153.5 (d) |
| CH₂CH₂CH₂OSO₂CH₃ | OCH₃ | OCH₃ | N | 145-147 (d) |
| CH₂CH(OSO₂CH₃)CH₃ | CH₃ | CH₃ | CH | |
| CH₂CH(OSO₂CH₃)CH₃ | CH₃ | OCH₃ | CH | |
| CH₂CH(OSO₂CH₃)CH₃ | OCH₃ | OCH₃ | CH | |
| CH₂CH(OSO₂CH₃)CH₃ | Cl | OCH₃ | CH | |
| CH₂CH(OSO₂CH₃)CH₃ | OCH₃ | CH(OCH₃)₂ | CH | |
| CH₂CH(OSO₂CH₃)CH₃ | CH₃ | OCH₃ | N | |
| CH₂CH(OSO₂CH₃)CH₃ | OCH₃ | OCH₃ | N | |
| CH₂CH(OSO₂CH₃)CH₂CH₃ | CH₃ | CH₃ | CH | |
| CH₂CH(OSO₂CH₃)CH₂CH₃ | CH₃ | OCH₃ | CH | |
| CH₂CH(OSO₂CH₃)CH₂CH₃ | OCH₃ | OCH₃ | CH | |
| CH₂CH(CH₃)CH₂OSO₂CH₃ | Cl | OCH₃ | CH | |
| CH₂CH(CH₃)CH₂OSO₂CH₃ | OCH₃ | CH(OCH₃)₂ | CH | |
| CH(CH₂OSO₂CH₃)CH₂CH₂CH₃ | CH₃ | OCH₃ | N | |
| CH(CH₂)CH₂OSO₂CH₃ | OCH₃ | OCH₃ | N | |
| CH₂CH(OSO₂CH₃)CH₂CH₃ | CH₃ | CH₃ | CH | |
| CH₂CH(OSO₂CH₃)CH₂CH₃ | CH₃ | OCH₃ | CH | |
| CH₂CH(OSO₂CH₃)CH₂CH₃ | OCH₃ | OCH₃ | CH | |
| CH₂CH(CH₃)CH₂OSO₂CH₃ | Cl | OCH₃ | CH | |
| CH₂CH(CH₃)CH₂OSO₂CH₃ | OCH₃ | CH(OCH₃)₂ | CH | |
| CH(CH₂OSO₂CH₃)CH₂CH₂CH₃ | CH₃ | OCH₃ | N | |
| CH(CH₂OSO₂CH₃)CH₂CH₂CH₃ | OCH₃ | OCH₃ | N | |
| CH₂CH₂OSO₂CH₂CH₃ | CH₃ | CH₃ | CH | |
| CH₂CH₂OSO₂CH₂CH₃ | CH₃ | OCH₃ | CH | |
| CH₂CH₂OSO₂CH₂CH₃ | OCH₃ | OCH₃ | CH | |
| CH₂CH₂OSO₂CH₂CH₃ | Cl | OCH₃ | CH | |
| CH₂CH₂OSO₂CH₂CH₃ | OCH₃ | CH(OCH₃)₂ | CH | |
| CH₂CH₂OSO₂CH₂CH₃ | CH₃ | OCH₃ | N | |
| CH₂CH₂OSO₂CH₂CH₃ | OCH₃ | OCH₃ | N | |
| CH₂CH₂OSO₂CH₂CH₂CH₃ | CH₃ | CH₃ | CH | |
| CH₂CH₂OSO₂CH₂CH₂CH₃ | CH₃ | OCH₃ | CH | |
| CH₂CH₂OSO₂CH₂CH₂CH₃ | OCH₃ | OCH₃ | CH | |
| CH₂CH₂OSO₂CH₂CH₂CH₃ | Cl | OCH₃ | CH | |
| CH₂CH₂OSO₂CH₂CH₂CH₃ | OCH₃ | CH(OCH₃)₂ | CH | |
| CH₂CH₂OSO₂CH₂CH₂CH₃ | CH₃ | OCH₃ | N | |
| CH₂CH₂OSO₂CH₂CH₂CH₃ | OCH₃ | OCH₃ | N | |
| CH₂CH₂OSO₂CH(CH₃)₂ | CH₃ | CH₃ | CH | |
| CH₂CH₂OSO₂CH(CH₃)₂ | CH₃ | OCH₃ | CH | |
| CH₂CH₂OSO₂CH(CH₃)₂ | OCH₃ | OCH₃ | CH | |

TABLE 1-continued

Structure: benzoate with -C(=O)OR₁ ortho to -SO₂NHC(=O)NH- linked to a triazine/pyrimidine ring bearing X, Y, Z substituents.

| R₁ | X | Y | Z | m.p. (°C.) |
|---|---|---|---|---|
| CH₂CH₂OSO₂CH(CH₃)₂ | Cl | OCH₃ | CH | |
| CH₂CH₂OSO₂CH(CH₃)₂ | OCH₃ | CH(OCH₃)₂ | CH | |
| CH₂CH₂OSO₂CH(CH₃)₂ | CH₃ | OCH₃ | N | |
| CH₂CH₂OSO₂CH(CH₃)₂ | OCH₃ | OCH₃ | N | |
| CH₂CH₂OSO₂—p-C₆H₄CH₃ | CH₃ | CH₃ | CH | |
| CH₂CH₂OSO₂—p-C₆H₄CH₃ | CH₃ | OCH₃ | CH | |
| CH₂CH₂OSO₂—p-C₆H₄CH₃ | OCH₃ | OCH₃ | CH | |
| CH₂CH₂OSO₂—p-C₆H₄CH₃ | Cl | OCH₃ | CH | |
| CH₂CH₂OSO₂—p-C₆H₄CH₃ | OCH₃ | CH(OCH₃)₂ | CH | |
| CH₂CH₂OSO₂—p-C₆H₄CH₃ | CH₃ | OCH₃ | N | |
| CH₂CH₂OSO₂—p-C₆H₄CH₃ | OCH₃ | OCH₃ | N | |
| CH₂CH₂OCOCH₃ | CH₃ | CH₃ | CH | 160–162 (d) |
| CH₂CH₂OCOCH₃ | CH₃ | OCH₃ | CH | 162–164 (d) |
| CH₂CH₂OCOCH₃ | OCH₃ | OCH₃ | CH | 119–122 (d) |
| CH₂CH₂OCOCH₃ | Cl | OCH₃ | CH | |
| CH₂CH₂OCOCH₃ | OCH₃ | CH(OCH₃)₂ | CH | |
| CH₂CH₂OCOCH₃ | CH₃ | OCH₃ | N | 128–131 (d) |
| CH₂CH₂OCOCH₃ | OCH₃ | OCH₃ | N | 140–141.5 (d) |
| CH₂CH₂OCO₂CH₃ | CH₃ | CH₃ | CH | |
| CH₂CH₂OCO₂CH₃ | CH₃ | OCH₃ | CH | |
| CH₂CH₂OCO₂CH₃ | OCH₃ | OCH₃ | CH | |
| CH₂CH₂OCO₂CH₃ | Cl | OCH₃ | CH | |
| CH₂CH₂OCO₂CH₃ | OCH₃ | CH(OCH₃)₂ | CH | |
| CH₂CH₂OCO₂CH₃ | CH₃ | OCH₃ | N | |
| CH₂CH₂OCO₂CH₃ | OCH₃ | OCH₃ | N | |
| CH₂CH₂OCON(CH₃)₂ | CH₃ | CH₃ | CH | |
| CH₂CH₂OCON(CH₃)₂ | CH₃ | OCH₃ | CH | |
| CH₂CH₂OCON(CH₃)₂ | OCH₃ | OCH₃ | CH | |
| CH₂CH₂OCON(CH₃)₂ | Cl | OCH₃ | CH | |
| CH₂CH₂OCON(CH₃)₂ | OCH₃ | CH(OCH₃)₂ | CH | |
| CH₂CH₂OCON(CH₃)₂ | CH₃ | OCH₃ | N | |
| CH₂CH₂OCON(CH₃)₂ | OCH₃ | OCH₃ | N | |
| CH₂CH₂OSO₂N(CH₃)₂ | CH₃ | CH₃ | CH | |
| CH₂CH₂OSO₂N(CH₃)₂ | CH₃ | OCH₃ | CH | |
| CH₂CH₂OSO₂N(CH₃)₂ | OCH₃ | OCH₃ | CH | |
| CH₂CH₂OSO₂N(CH₃)₂ | Cl | OCH₃ | CH | |
| CH₂CH₂OSO₂N(CH₃)₂ | OCH₃ | CH(OCH₃)₂ | CH | |
| CH₂CH₂OSO₂N(CH₃)₂ | CH₃ | OCH₃ | N | |
| CH₂CH₂OSO₂N(CH₃)₂ | OCH₃ | OCH₃ | N | |
| CH₂CH₂OSi(CH₃)₃ | CH₃ | CH₃ | CH | |
| CH₂CH₂OSi(CH₃)₃ | CH₃ | OCH₃ | CH | |
| CH₂CH₂OSi(CH₃)₃ | OCH₃ | OCH₃ | CH | |
| CH₂CH₂OSi(CH₃)₃ | Cl | OCH₃ | CH | |
| CH₂CH₂OSi(CH₃)₃ | OCH₃ | CH(OCH₃)₂ | CH | |
| CH₂CH₂OSi(CH₃)₃ | CH₃ | OCH₃ | N | |
| CH₂CH₂OSi(CH₃)₃ | OCH₃ | OCH₃ | N | |
| CH₂CH₂SOCH₃ | CH₃ | CH₃ | CH | |
| CH₂CH₂SOCH₃ | CH₃ | OCH₃ | CH | |
| CH₂CH₂SOCH₃ | OCH₃ | OCH₃ | CH | |
| CH₂CH₂SOCH₃ | Cl | OCH₃ | CH | |
| CH₂CH₂SOCH₃ | OCH₃ | CH(OCH₃)₂ | CH | |
| CH₂CH₂SOCH₃ | CH₃ | OCH₃ | N | |
| CH₂CH₂SOCH₃ | OCH₃ | OCH₃ | N | |
| CH₂CH₂N(CH₃)₂ | CH₃ | CH₃ | CH | |
| CH₂CH₂N(CH₃)₂ | CH₃ | OCH₃ | CH | |
| CH₂CH₂N(CH₃)₂ | OCH₃ | OCH₃ | CH | |
| CH₂CH₂N(CH₃)₂ | Cl | OCH₃ | CH | |
| CH₂CH₂N(CH₃)₂ | OCH₃ | CH(OCH₃)₂ | CH | |
| CH₂CH₂N(CH₃)₂ | CH₃ | OCH₃ | N | |
| CH₂CH₂N(CH₃)₂ | OCH₃ | OCH₃ | N | |
| CH₂CH₂OCF₂H | CH₃ | CH₃ | CH | |
| CH₂CH₂OCF₂H | CH₃ | OCH₃ | CH | |
| CH₂CH₂OCF₂H | OCH₃ | OCH₃ | CH | |
| CH₂CH₂OCF₂H | Cl | OCH₃ | CH | |
| CH₂CH₂OCF₂H | OCH₃ | CH(OCH₃)₂ | CH | |
| CH₂CH₂OCF₂H | CH₃ | OCH₃ | N | |
| CH₂CH₂OCF₂H | OCH₃ | OCH₃ | N | |
| CH₂CH₂OCH₂CH₂F | CH₃ | CH₃ | CH | |
| CH₂CH₂OCH₂CH₂F | CH₃ | OCH₃ | CH | |
| CH₂CH₂OCH₂CH₂F | OCH₃ | OCH₃ | CH | |

TABLE 1-continued

[Structure: benzoate with -C(=O)OR₁ ortho to -SO₂NHC(=O)NH- linked to a triazine/pyrimidine ring bearing X, Y, Z substituents]

| R₁ | X | Y | Z | m.p. (°C.) |
|---|---|---|---|---|
| CH₂CH₂OCH₂CH₂F | Cl | OCH₃ | CH | |
| CH₂CH₂OCH₂CH₂F | OCH₃ | CH(OCH₃)₂ | CH | |
| CH₂CH₂OCH₂CH₂F | CH₃ | OCH₃ | N | |
| CH₂CH₂OCH₂CH₂F | OCH₃ | OCH₃ | N | |
| CH₂CH₂OCH₂CF₃ | CH₃ | CH₃ | CH | |
| CH₂CH₂OCH₂CF₃ | CH₃ | OCH₃ | CH | |
| CH₂CH₂OCH₂CF₃ | OCH₃ | OCH₃ | CH | |
| CH₂CH₂OCH₂CF₃ | Cl | OCH₃ | CH | |
| CH₂CH₂OCH₂CF₃ | OCH₃ | CH(OCH₃)₂ | CH | |
| CH₂CH₂OCH₂CF₃ | CH₃ | OCH₃ | N | |
| CH₂CH₂OCH₂CF₃ | OCH₃ | OCH₃ | N | |
| CH₂CH₂OCONHCH₃ | CH₃ | CH₃ | CH | |
| CH₂CH₂OCONHCH₃ | CH₃ | OCH₃ | CH | |
| CH₂CH₂OCONHCH₃ | OCH₃ | OCH₃ | CH | |
| CH₂CH₂OCONHCH₃ | Cl | OCH₃ | CH | |
| CH₂CH₂OCONHCH₃ | OCH₃ | CH(OCH₃)₂ | CH | |
| CH₂CH₂OCONHCH₃ | CH₃ | OCH₃ | N | |
| CH₂CH₂OCONHCH₃ | OCH₃ | OCH₃ | N | |
| CH₂CH₂OCSNHCH₃ | CH₃ | CH₃ | CH | |
| CH₂CH₂OCSNHCH₃ | CH₃ | OCH₃ | CH | |
| CH₂CH₂OCSNHCH₃ | OCH₃ | OCH₃ | CH | |
| CH₂CH₂OCSNHCH₃ | Cl | OCH₃ | CH | |
| CH₂CH₂OCSNHCH₃ | OCH₃ | CH(OCH₃)₂ | CH | |
| CH₂CH₂OCSNHCH₃ | CH₃ | OCH₃ | N | |
| CH₂CH₂OCSNHCH₃ | OCH₃ | OCH₃ | N | |
| CH₂CH₂OPO(OCH₃)₂ | CH₃ | CH₃ | CH | |
| CH₂CH₂OPO(OCH₃)₂ | CH₃ | OCH₃ | CH | |
| CH₂CH₂OPO(OCH₃)₂ | OCH₃ | OCH₃ | CH | |
| CH₂CH₂OPO(OCH₃)₂ | Cl | OCH₃ | CH | |
| CH₂CH₂OPO(OCH₃)₂ | OCH₃ | CH(OCH₃)₂ | CH | |
| CH₂CH₂OPO(OCH₃)₂ | CH₃ | OCH₃ | N | |
| CH₂CH₂OPO(OCH₃)₂ | OCH₃ | OCH₃ | N | |
| CH₂CH₂OPS(OCH₃)₂ | CH₃ | CH₃ | CH | |
| CH₂CH₂OPS(OCH₃)₂ | CH₃ | OCH₃ | CH | |
| CH₂CH₂OPS(OCH₃)₂ | OCH₃ | OCH₃ | CH | |
| CH₂CH₂OPS(OCH₃)₂ | Cl | OCH₃ | CH | |
| CH₂CH₂OPS(OCH₃)₂ | OCH₃ | CH(OCH₃)₂ | CH | |
| CH₂CH₂OPS(OCH₃)₂ | CH₃ | OCH₃ | N | |
| CH₂CH₂OPS(OCH₃)₂ | OCH₃ | OCH₃ | N | |
| CH₂CH₂OCO₂C₆H₅ | CH₃ | CH₃ | CH | |
| CH₂CH₂OCO₂C₆H₅ | CH₃ | OCH₃ | CH | |
| CH₂CH₂OCO₂C₆H₅ | OCH₃ | OCH₃ | CH | |
| CH₂CH₂OCO₂C₆H₅ | Cl | OCH₃ | CH | |
| CH₂CH₂OCO₂C₆H₅ | OCH₃ | CH(OCH₃)₂ | CH | |
| CH₂CH₂OCO₂C₆H₅ | CH₃ | OCH₃ | N | |
| CH₂CH₂OCO₂C₆H₅ | OCH₃ | OCH₃ | N | |
| CH₂CH(OH)CH₂OH | CH₃ | CH₃ | CH | |
| CH₂CH(OH)CH₂OH | CH₃ | OCH₃ | CH | |
| CH₂CH(OH)CH₂OH | OCH₃ | OCH₃ | CH | |
| CH₂CH(OH)CH₂OH | Cl | OCH₃ | CH | |
| CH₂CH(OH)CH₂OH | OCH₃ | CH(OCH₃)₂ | CH | |
| CH₂CH(OH)CH₂OH | CH₃ | OCH₃ | N | |
| CH₂CH(OH)CH₂OH | OCH₃ | OCH₃ | N | |
| CH(CH₂OH)₂ | CH₃ | CH₃ | CH | |
| CH(CH₂OH)₂ | CH₃ | OCH₃ | CH | |
| CH(CH₂OH)₂ | OCH₃ | OCH₃ | CH | |
| CH(CH₂OH)₂ | Cl | OCH₃ | CH | |
| CH(CH₂OH)₂ | OCH₃ | CH(OCH₃)₂ | CH | |
| CH(CH₂OH)₂ | CH₃ | OCH₃ | N | |
| CH(CH₂OH)₂ | OCH₃ | OCH₃ | N | |
| CH₂CH₂OSO₂CH₃ | CH₃ | CH₃ | N | 150–153 (d) |
| CH₂CH₂CH₂OSO₂CH₃ | CH₃ | CH₃ | N | 158.5–160 (d) |
| CH₂CH₂OPO(OCH₂CH₃)₂ | CH₃ | CH₃ | CH | |
| CH₂CH₂OPO(OCH₂CH₃)₂ | CH₃ | OCH₃ | CH | |
| CH₂CH₂OPO(OCH₂CH₃)₂ | OCH₃ | OCH₃ | CH | |
| CH₂CH₂OPO(OCH₂CH₃)₂ | Cl | OCH₃ | CH | |
| CH₂CH₂OPO(OCH₂CH₃)₂ | CH₃ | OCH₃ | N | |
| CH₂CH₂OPO(OCH₂CH₃)₂ | OCH₃ | OCH₃ | N | |
| CH₂CH₂OSO₂—n-C₈H₁₇ | CH₃ | CH₃ | CH | |
| CH₂CH₂OSO₂—n-C₈H₁₇ | CH₃ | OCH₃ | CH | 79–82 (d) |

TABLE 1-continued

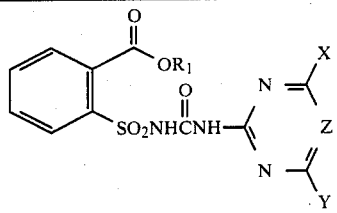

| R₁ | X | Y | Z | m.p. (°C.) |
|---|---|---|---|---|
| CH₂CH₂OSO₂—n-C₈H₁₇ | OCH₃ | OCH₃ | CH | wax |
| CH₂CH₂OSO₂—n-C₈H₁₇ | Cl | OCH₃ | CH | wax |
| CH₂CH₂OSO₂—n-C₈H₁₇ | CH₃ | OCH₃ | N | oil |
| CH₂CH₂OSO₂—n-C₈H₁₇ | OCH₃ | OCH₃ | N | wax |
| CH(CH₃)CH₂OSO₂CH₃ | CH₃ | CH₃ | CH | |
| CH(CH₃)CH₂OSO₂CH₃ | CH₃ | OCH₃ | CH | |
| CH(CH₃)CH₂OSO₂CH₃ | OCH₃ | OCH₃ | CH | |
| CH(CH₃)CH₂OSO₂CH₃ | Cl | OCH₃ | CH | |
| CH(CH₃)CH₂OSO₂CH₃ | CH₃ | OCH₃ | N | |
| CH(CH₃)CH₂OSO₂CH₃ | OCH₃ | OCH₃ | N | |
| CH₂CH₂OH | OCH₂CH₃ | NHCH₃ | N | 132–135 (d) |
| CH₂CH₂OSO₂CH₃ | OCH₂CH₃ | NHCH₃ | N | 144–146 (d) |
| CH₂CH₂OCH₂C₆H₅ | CH₃ | CH₃ | CH | |
| CH₂CH₂OCH₂C₆H₅ | CH₃ | OCH₃ | CH | |
| CH₂CH₂OCH₂C₆H₅ | OCH₃ | OCH₃ | CH | 133–135 (d) |
| CH₂CH₂OCH₂C₆H₅ | Cl | OCH₃ | CH | |
| CH₂CH₂OCH₂C₆H₅ | CH₃ | OCH₃ | N | 118–121 (d) |
| CH₂CH₂OCH₂C₆H₅ | OCH₃ | OCH₃ | N | |
| CH₂CH₂OCH₂C₆H₅ | OCH₂CH₃ | NHCH₃ | N | |
| CH₂CH₂OCONH₂ | CH₃ | CH₃ | CH | |
| CH₂CH₂OCONH₂ | CH₃ | OCH₃ | CH | |
| CH₂CH₂OCONH₂ | OCH₃ | OCH₃ | CH | |
| CH₂CH₂OCONH₂ | Cl | OCH₃ | CH | |
| CH₂CH₂OCONH₂ | CH₃ | OCH₃ | N | |
| CH₂CH₂OCONH₂ | OCH₃ | OCH₃ | N | |
| CH₂CH₂OCH₂p-ClC₆H₄ | OCH₃ | OCH₃ | CH | |
| CH₂CH₂OCH₂p-ClC₆H₄ | CH₃ | OCH₃ | N | |
| CH₂CH₂OCH₂m-ClC₆H₄ | OCH₃ | OCH₃ | CH | |
| CH₂CH₂OCH₂m-ClC₆H₄ | CH₃ | OCH₃ | N | |
| CH₂CH₂OCH₂o-ClC₆H₄ | OCH₃ | OCH₃ | CH | |
| CH₂CH₂OCH₂o-ClC₆H₄ | CH₃ | OCH₃ | N | |
| CH₂CH₂SH | CH₃ | CH₃ | CH | |
| CH₂CH₂SH | CH₃ | OCH₃ | CH | |
| CH₂CH₂SH | OCH₃ | OCH₃ | CH | |
| CH₂CH₂SH | Cl | OCH₃ | CH | |
| CH₂CH₂SH | CH₃ | CH₃ | N | |
| CH₂CH₂SH | CH₃ | OCH₃ | N | |
| CH₂CH₂SH | OCH₃ | OCH₃ | N | |
| CH₂CH₂SH | OCH₂CH₃ | NHCH₃ | N | |
| CH₂CH₂SH | OCH₃ | N(CH₃)₂ | N | |
| CH₂CH(SH)CH₃ | CH₃ | CH₃ | CH | |
| CH₂CH(SH)CH₃ | CH₃ | OCH₃ | CH | |
| CH₂CH(SH)CH₃ | OCH₃ | OCH₃ | CH | |
| CH₂CH(SH)CH₃ | Cl | OCH₃ | CH | |
| CH₂CH(SH)CH₃ | CH₃ | OCH₃ | N | |
| CH₂CH(SH)CH₃ | OCH₃ | OCH₃ | N | |
| CH₂CH₂CH₂SH | CH₃ | CH₃ | CH | |
| CH₂CH₂CH₂SH | CH₃ | OCH₃ | CH | |
| CH₂CH₂CH₂SH | OCH₃ | OCH₃ | CH | |
| CH₂CH₂CH₂SH | Cl | OCH₃ | CH | |
| CH₂CH₂CH₂SH | CH₃ | OCH₃ | N | |
| CH₂CH₂CH₂SH | OCH₃ | OCH₃ | N | |
| CH₂CH(SH)CH₂SH | CH₃ | CH₃ | CH | |
| CH₂CH(SH)CH₂SH | CH₃ | OCH₃ | CH | |
| CH₂CH(SH)CH₂SH | OCH₃ | OCH₃ | CH | |
| CH₂CH(SH)CH₂SH | Cl | OCH₃ | CH | |
| CH₂CH(SH)CH₂SH | CH₃ | OCH₃ | N | |
| CH₂CH(SH)CH₂SH | OCH₃ | OCH₃ | N | |
| CH₂CH₂SCOCH₃ | CH₃ | CH₃ | CH | |
| CH₂CH₂SCOCH₃ | CH₃ | OCH₃ | CH | |
| CH₂CH₂SCOCH₃ | OCH₃ | OCH₃ | CH | |
| CH₂CH₂SCOCH₃ | Cl | OCH₃ | CH | |
| CH₂CH₂SCOCH₃ | CH₃ | OCH₃ | N | |
| CH₂CH₂SCOCH₃ | OCH₃ | OCH₃ | N | |
| CH₂CH₂SCOCH₂CH₃ | OCH₃ | OCH₃ | CH | |
| CH₂CH₂SCOCH₂CH₂CH₃ | OCH₃ | OCH₃ | CH | |
| CH₂CH₂SCOCH(CH₃)₂ | OCH₃ | OCH₃ | CH | |
| CH₂CH₂SCO₂CH₃ | CH₃ | CH₃ | CH | |
| CH₂CH₂SCO₂CH₃ | CH₃ | OCH₃ | CH | |
| CH₂CH₂SCO₂CH₃ | OCH₃ | OCH₃ | CH | |

TABLE 1-continued

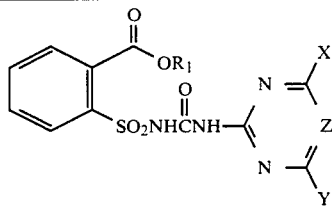

| R₁ | X | Y | Z | m.p. (°C.) |
|---|---|---|---|---|
| CH₂CH₂SCO₂CH₃ | Cl | OCH₃ | CH | |
| CH₂CH₂SCO₂CH₃ | CH₃ | OCH₃ | N | |
| CH₂CH₂SCO₂CH₃ | OCH₃ | OCH₃ | N | |
| CH₂CH₂SCO₂C₆H₅ | OCH₃ | OCH₃ | CH | |
| CH₂CH₂SCO₂C₆H₅ | CH₃ | OCH₃ | N | |
| CH₂CH₂SCON(CH₃)₂ | CH₃ | OCH₃ | CH | |
| CH₂CH₂SCON(CH₃)₂ | OCH₃ | OCH₃ | CH | |
| CH₂CH₂SCON(CH₃)₂ | CH₃ | OCH₃ | N | |
| CH₂CH₂SCONH₂ | CH₃ | CH₃ | CH | |
| CH₂CH₂SCONH₂ | CH₃ | OCH₃ | CH | |
| CH₂CH₂SCONH₂ | OCH₃ | OCH₃ | CH | |
| CH₂CH₂SCONH₂ | Cl | OCH₃ | CH | |
| CH₂CH₂SCONH₂ | CH₃ | OCH₃ | N | |
| CH₂CH₂SCONH₂ | OCH₃ | OCH₃ | N | |
| CH₂CH₂SP(=O)(OCH₂CH₃)₂ | CH₃ | CH₃ | CH | |
| CH₂CH₂SP(=O)(OCH₂CH₃)₂ | CH₃ | OCH₃ | CH | |
| CH₂CH₂SP(=O)(OCH₂CH₃)₂ | OCH₃ | OCH₃ | CH | |
| CH₂CH₂SP(=O)(OCH₂CH₃)₂ | Cl | OCH₃ | CH | |
| CH₂CH₂SP(=O)(OCH₂CH₃)₂ | CH₃ | OCH₃ | N | |
| CH₂CH₂SP(=O)(OCH₂CH₃)₂ | OCH₃ | OCH₃ | N | |
| CH₂CH₂SP(=S)(OCH₃)₂ | CH₃ | CH₃ | CH | |
| CH₂CH₂SP(=S)(OCH₃)₂ | CH₃ | OCH₃ | CH | |
| CH₂CH₂SP(=S)(OCH₃)₂ | OCH₃ | OCH₃ | CH | |
| CH₂CH₂SP(=S)(OCH₃)₂ | Cl | OCH₃ | CH | |
| CH₂CH₂SP(=S)(OCH₃)₂ | CH₃ | OCH₃ | N | |
| CH₂CH₂SP(=S)(OCH₃)₂ | OCH₃ | OCH₃ | N | |
| CH₂CH₂OH | OCH₃ | NH₂ | CH | |
| CH₂CH₂OH | OCH₃ | NH₂ | N | |
| CH₂CH₂OH | CH₃ | CH₂OCH₂CH₃ | CH | |
| CH₂CH₂OH | OCH₃ | CH₂OCH₂CH₃ | CH | |
| CH₂CH₂OH | OCH₃ | CH₂OCH₂CH₃ | N | |
| CH₂CH₂OH | CH₃ | cyclopropyl | CH | |
| CH₂CH₂OH | OCH₃ | cyclopropyl | CH | |
| CH₂CH₂OH | CH₃ | cyclopropyl | N | |
| CH₂CH₂OH | OCH₃ | cyclopropyl | N | |
| CH₂CH₂OH | CH₃ | CH₂SCH₃ | CH | |
| CH₂CH₂OH | OCH₃ | CH₂SCH₃ | CH | |
| CH₂CH₂OH | OCH₃ | CH₂SOCH₃ | CH | |
| CH₂CH₂OH | CH₃ | CH₂SO₂CH₃ | CH | |
| CH₂CH₂OH | OCH₃ | CH₂SO₂CH₃ | CH | |

TABLE 2

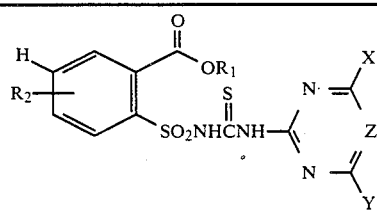

TABLE 2-continued

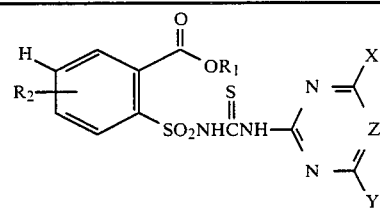

| R₁ | R₂ | X | Y | Z | m.p. (°C.) | R₁ | R₂ | X | Y | Z | m.p. (°C.) |
|---|---|---|---|---|---|---|---|---|---|---|---|
| CH₂CH₂OH | H | CH₃ | CH₃ | CH | | CH₂CH₂OSO₂CH₃ | H | OCH₃ | OCH₃ | N | |
| CH₂CH₂OH | H | CH₃ | OCH₃ | CH | | CH₂CH₂OH | 3-Cl | CH₃ | CH₃ | CH | |
| CH₂CH₂OH | H | OCH₃ | OCH₃ | CH | | CH₂CH₂OH | 6-Cl | CH₃ | OCH₃ | CH | |
| CH₂CH₂OH | H | Cl | OCH₃ | CH | | CH₂CH₂OH | 5-CF₃ | OCH₃ | OCH₃ | CH | |
| CH₂CH₂OH | H | OCH₃ | CH(OCH₃)₂ | CH | | CH₂CH₂OH | 5-CH₃ | Cl | OCH₃ | CH | |
| CH₂CH₂OH | H | CH₃ | OCH₃ | N | | CH₂CH₂OH | 5-SCH₃ | OCH₃ | CH(OCH₃)₂ | CH | |
| CH₂CH₂OH | H | OCH₃ | OCH₃ | N | | CH₂CH₂OH | 5-OCH₃ | CH₃ | OCH₃ | N | |
| CH₂CH₂OSO₂CH₃ | H | CH₃ | CH₃ | CH | | CH₂CH₂OH | 3-CH₃ | OCH₃ | OCH₃ | N | |
| CH₂CH₂OSO₂CH₃ | H | CH₃ | OCH₃ | CH | | CH₂CH₂OSO₂CH₃ | 5-C₂H₅ | CH₃ | CH₃ | CH | |
| CH₂CH₂OSO₂CH₃ | H | OCH₃ | OCH₃ | CH | | CH₂CH₂OSO₂CH₃ | 5-F | CH₃ | OCH₃ | CH | |
| CH₂CH₂OSO₂CH₃ | H | Cl | OCH₃ | CH | | CH₂CH₂OSO₂CH₃ | 5-Br | OCH₃ | OCH₃ | CH | |
| CH₂CH₂OSO₂CH₃ | H | OCH₃ | CH(OCH₃)₂ | CH | | CH₂CH₂OSO₂CH₃ | 5-OCF₂H | Cl | OCH₃ | CH | |
| CH₂CH₂OSO₂CH₃ | H | CH₃ | OCH₃ | N | | CH₂CH₂OSO₂CH₃ | 5-SCF₂H | OCH₃ | CH(OCH₃)₂ | CH | |

TABLE 2-continued

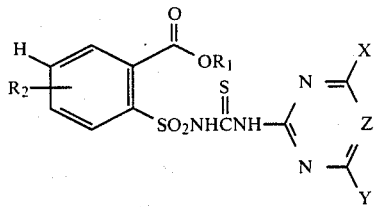

| R₁ | R₂ | X | Y | Z | m.p. (°C.) |
|---|---|---|---|---|---|
| CH₂CH₂OSO₂CH₃ | 5-OCH₃ | CH₃ | OCH₃ | N | |
| CH₂CH₂OSO₂CH₃ | 5-OCH₃ | OCH₃ | OCH₃ | N | |
| CH₂CH₂SH | H | CH₃ | OCH₃ | CH | |
| CH₂CH₂SH | H | OCH₃ | OCH₃ | CH | |
| CH₂CH₂SH | H | CH₃ | OCH₃ | N | |
| CH₂CH₂SH | H | OCH₃ | OCH₃ | N | |

TABLE 3

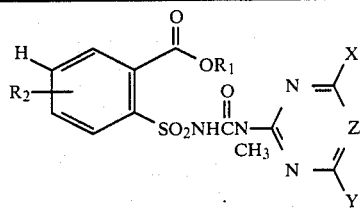

| R₁ | R₂ | X | Y | Z | m.p. (°C.) |
|---|---|---|---|---|---|
| CH₂CH₂OH | H | CH₃ | CH₃ | CH | |
| CH₂CH₂OH | H | CH₃ | OCH₃ | CH | |
| CH₂CH₂OH | H | OCH₃ | OCH₃ | CH | |
| CH₂CH₂OH | H | Cl | OCH₃ | CH | |
| CH₂CH₂OH | H | OCH₃ | CH(OCH₃)₂ | CH | |
| CH₂CH₂OH | H | CH₃ | OCH₃ | N | |
| CH₂CH₂OH | H | OCH₃ | OCH₃ | N | |
| CH₂CH₂OSO₂CH₃ | H | CH₃ | CH₃ | CH | |
| CH₂CH₂OSO₂CH₃ | H | CH₃ | OCH₃ | CH | |
| CH₂CH₂OSO₂CH₃ | H | OCH₃ | OCH₃ | CH | |
| CH₂CH₂OSO₂CH₃ | H | Cl | OCH₃ | CH | |
| CH₂CH₂OSO₂CH₃ | H | OCH₃ | CH(OCH₃)₂ | CH | |
| CH₂CH₂OSO₂CH₃ | H | CH₃ | OCH₃ | N | |
| CH₂CH₂OSO₂CH₃ | H | OCH₃ | OCH₃ | N | |
| CH₂CH₂OH | 3-Cl | CH₃ | CH₃ | CH | |
| CH₂CH₂OH | 3-Cl | CH₃ | OCH₃ | CH | |
| CH₂CH₂OH | 6-Cl | OCH₃ | OCH₃ | CH | |
| CH₂CH₂OH | 5-Cl | Cl | OCH₃ | CH | |
| CH₂CH₂OH | 5-CF₃ | OCH₃ | CH(OCH₃)₂ | CH | |
| CH₂CH₂OH | 5-OCH₃ | CH₃ | OCH₃ | N | |
| CH₂CH₂OH | 5-OCH₃ | OCH₃ | OCH₃ | N | |
| CH₂CH₂OSO₂CH₃ | 5-Cl | CH₃ | CH₃ | CH | |
| CH₂CH₂OSO₂CH₃ | 5-Cl | CH₃ | OCH₃ | CH | |
| CH₂CH₂OSO₂CH₃ | 5-CH₃ | OCH₃ | OCH₃ | CH | |
| CH₂CH₂OSO₂CH₃ | 5-CH₃ | Cl | OCH₃ | CH | |
| CH₂CH₂OSO₂CH₃ | 5-CH₃ | OCH₃ | CH(OCH₃)₂ | CH | |
| CH₂CH₂OSO₂CH₃ | 5-OCH₃ | CH₃ | OCH₃ | N | |
| CH₂CH₂OSO₂CH₃ | 5-OCH₃ | OCH₃ | OCH₃ | N | |
| CH₂CH₂OH | 5-SCH₃ | CH₃ | OCH₃ | CH | |
| CH₂CH₂OH | 5-SCH₃ | OCH₃ | OCH₃ | CH | |
| CH₂CH₂OH | 5-SCH₃ | CH₃ | OCH₃ | N | |
| CH₂CH₂OH | 5-SCH₃ | OCH₃ | OCH₃ | N | |
| CH₂CH₂OH | 5-Cl | CH₃ | OCH₃ | N | |
| CH₂CH₂OH | 5-Cl | OCH₃ | OCH₃ | N | |
| CH₂CH₂OH | 5-CH₂OCH₃ | CH₃ | OCH₃ | CH | |
| CH₂CH₂OH | 5-CH₂OCH₃ | OCH₃ | OCH₃ | CH | |
| CH₂CH₂OH | 5-CH₂OCH₃ | CH₃ | OCH₃ | N | |
| CH₂CH₂OH | 5-CH₂OCH₃ | OCH₃ | OCH₃ | N | |
| CH₂CH₂OSO₂CH₃ | 5-Cl | CH₃ | OCH₃ | N | |
| CH₂CH₂OSO₂CH₃ | 5-SCH₃ | CH₃ | OCH₃ | N | |
| CH₂CH₂OSO₂CH₃ | 5-SCH₃ | OCH₃ | OCH₃ | N | |
| CH₂CH₂SH | H | CH₃ | OCH₃ | CH | |
| CH₂CH₂SH | H | OCH₃ | OCH₃ | CH | |
| CH₂CH₂SH | H | Cl | OCH₃ | CH | |
| CH₂CH₂SH | H | CH₃ | OCH₃ | N | |

TABLE 3-continued

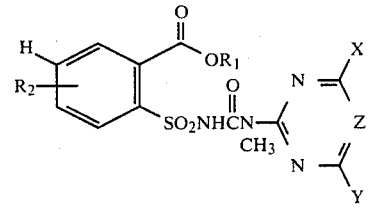

| R₁ | R₂ | X | Y | Z | m.p. (°C.) |
|---|---|---|---|---|---|
| CH₂CH₂SH | H | OCH₃ | OCH₃ | N | |

TABLE 4

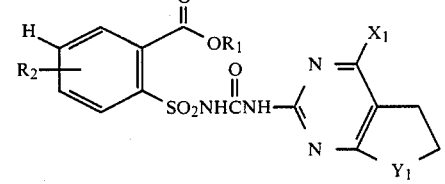

| R₁ | R₂ | X₁ | Y₁ | m.p. (°C.) |
|---|---|---|---|---|
| CH₂CH₂OH | H | CH₃ | O | |
| CH₂CH₂OH | H | OCH₃ | O | |
| CH₂CH₂OH | H | OCH₂CH₃ | O | |
| CH₂CH₂OH | H | OCF₂H | O | |
| CH₂CH₂OH | H | CH₃ | CH₂ | |
| CH₂CH₂OH | H | OCH₃ | CH₂ | |
| CH₂CH₂OH | H | OCH₂CH₃ | CH₂ | |
| CH₂CH₂OH | H | OCF₂H | CH₂ | |
| CH₂CH₂OSO₂CH₃ | H | CH₃ | O | |
| CH₂CH₂OSO₂CH₃ | H | OCH₃ | O | |
| CH₂CH₂OSO₂CH₃ | H | OCH₂CH₃ | O | |
| CH₂CH₂OSO₂CH₃ | H | OCF₂H | O | |
| CH₂CH₂OSO₂CH₃ | H | CH₃ | CH₂ | |
| CH₂CH₂OSO₂CH₃ | H | OCH₃ | CH₂ | |
| CH₂CH₂OSO₂CH₃ | H | OCH₂CH₃ | CH₂ | |
| CH₂CH₂OSO₂CH₃ | H | OCF₂H | CH₂ | |
| CH₂CH₂CH₂OH | H | CH₃ | O | |
| CH₂CH(OH)CH₃ | H | CH₃ | O | |
| CH(CH₃)CH₂OH | H | CH₃ | O | |
| CH₂CH₂OCONHCH₃ | H | CH₃ | | |
| CH₂CH₂OCONHCH₃ | H | OCH₃ | | |
| CH₂CH₂OCSNHCH₃ | H | OCH₃ | | |
| CH₂CH(OSO₂CH₃)CH₃ | H | OCH₃ | | |
| CH(CH₃)CH₂OSO₂CH₃ | H | OCH₃ | | |
| CH₂CH₂OSO₂CH₃ | 3-Cl | OCH₃ | O | |
| CH₂CH₂OSO₂CH₃ | 5-Cl | OCH₃ | O | |
| CH₂CH₂OH | 6-Cl | OCH₃ | O | |
| CH₂CH₂OH | 5-OCH₃ | OCH₃ | O | |
| CH₂CH₂SH | H | CH₃ | O | |
| CH₂CH₂SH | H | OCH₃ | O | |
| CH₂CH₂SH | H | OCH₂CH₃ | O | |

TABLE 5

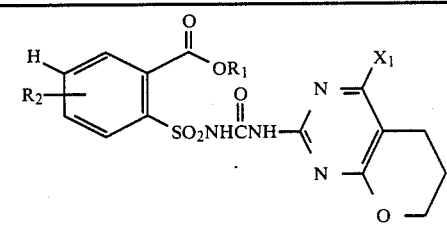

| R₁ | R₂ | X₁ | m.p. (°C.) |
|---|---|---|---|
| CH₂CH₂OH | H | CH₃ | |
| CH₂CH₂OH | H | OCH₃ | |
| CH₂CH₂OH | H | OCH₂CH₃ | |

TABLE 5-continued

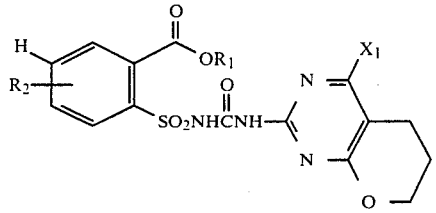

| R₁ | R₂ | X₁ | m.p. (°C.) |
|---|---|---|---|
| CH₂CH₂OH | H | OCF₂H | |
| CH₂CH₂OSO₂CH₃ | H | CH₃ | |
| CH₂CH₂OSO₂CH₃ | H | OCH₃ | |
| CH₂CH₂OSO₂CH₃ | H | OCH₂CH₃ | |
| CH₂CH₂OSO₂CH₃ | H | OCF₂H | |
| CH₂CH₂OCONHCH₃ | 5-Cl | OCH₃ | |
| CH₂CH₂OCSNHCH₃ | 5-OCH₃ | OCH₃ | |
| CH₂CH₂OSi(CH₃)₃ | H | OCH₃ | |
| CH₂CH₂CH₂OH | H | OCH₃ | |
| CH₂CH₂SH | H | CH₃ | |
| CH₂CH₂SH | H | OCH₃ | |

TABLE 6

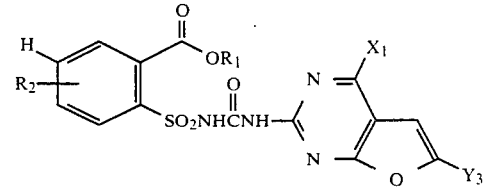

| R₁ | R₂ | X₁ | Y₃ | m.p. (°C.) |
|---|---|---|---|---|
| CH₂CH₂OSO₂CH₃ | H | CH₃ | H | |
| CH₂CH₂OSO₂CH₃ | H | OCH₃ | H | |
| CH₂CH₂OSO₂CH₃ | H | OCH₂CH₃ | H | |
| CH₂CH₂OSO₂CH₃ | H | OCF₂H | H | |
| CH₂CH₂OSO₂CH₃ | H | CH₃ | CH₃ | |
| CH₂CH₂OSO₂CH₃ | H | OCH₃ | CH₃ | |
| CH₂CH₂OSO₂CH₃ | H | OCH₂CH₃ | CH₃ | |
| CH₂CH₂OSO₂CH₃ | H | OCF₂H | CH₃ | |
| CH₂CH₂OH | H | CH₃ | H | |
| CH₂CH₂OH | H | OCH₃ | H | |
| CH₂CH₂OH | H | OCH₃ | CH₃ | |
| CH₂CH₂OH | H | CH₃ | CH₃ | |
| CH₂CH₂OPO(OCH₃)₂ | H | CH₃ | H | |
| CH₂CH₂CH₂OH | H | OCH₃ | H | |
| CH₂CH(OH)CH₂OH | 5-Cl | OCH₃ | H | |
| CH₂CH(OSO₂CH₃)CH₃ | 5-OCH₃ | OCH₃ | CH₃ | |
| CH₂CH₂N(CH₃)₂ | 6-Cl | CH₃ | H | |
| CH₂CH₂SOCH₃ | 3-Cl | CH₃ | CH₃ | |
| CH₂CH₂SH | H | CH₃ | H | |
| CH₂CH₂SH | H | CH₃ | CH₃ | |
| CH₂CH₂SH | H | OCH₃ | H | |
| CH₂CH₂SH | H | OCH₃ | CH₃ | |

TABLE 7

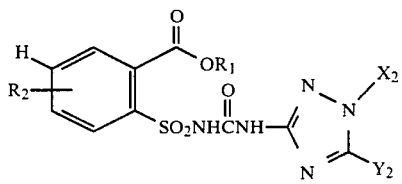

| R₁ | R₂ | X₂ | Y₂ | m.p. (°C.) |
|---|---|---|---|---|
| CH₂CH₂OH | H | CH₃ | OCH₃ | |
| CH₂CH₂CH₂OH | H | CH₂CH₃ | OCH₃ | |
| CH₂CH(OH)CH₃ | H | CH₂CF₃ | OCH₃ | |
| CH₂CH(OSO₂CH₃)CH₃ | H | CH₃ | OCH₂CH₃ | |
| CH₂CH(OH)CH₂OH | H | CH₂CH₃ | OCH₂CH₃ | |
| CH₂CH(OSO₂CH₃)CH₂OSO₂CH₃ | H | CH₂CF₃ | OCH₂CH₃ | |
| CH(CHOH)₂ | H | CH₃ | SCH₃ | |
| CH(CH₃)CH₂CH₂OH | H | CH₂CH₃ | SCH₃ | |
| CH₂CH₂SOCH₃ | H | CH₂CF₃ | SCH₃ | |
| CH₂CH₂OCF₂H | H | CH₃ | SCH₂CH₃ | |
| CH₂CH₂OCH₂CH₂F | H | CH₂CH₃ | SCH₂CH₃ | |
| CH₂CH₂OPO(OCH₃)₂ | H | CH₂CF₃ | SCH₂CH₃ | |
| CH₂CH₂OSO₂N(CH₃)₂ | H | CH₃ | CH₃ | |
| CH₂CH₂Si(CH₃)₂C₆H₅ | H | CH₂CH₃ | CH₃ | |
| CH₂CH₂OH | H | CH₂CF₃ | CH₃ | |
| CH₂CH₂OH | H | CH₃ | CH₂CH₃ | |
| CH₂CH₂OH | H | CH₂CH₃ | CH₂CH₃ | |
| CH₂CH₂OSO₂CH₂CH₃ | H | CH₂CF₃ | CH₂CH₃ | |
| CH₂CH₂OSO₂CH(CH₃)₂ | H | CH₃ | OCH₃ | |
| CH₂CH₂CH₂CH₂OH | H | CH₂CH₃ | OCH₃ | |
| CH₂C≡CCH₂OH | H | CH₂CF₃ | OCH₃ | |
| CH₂CH₂OSO₂CH₃ | H | CH₃ | OCH₃ | |
| CH₂CH₂OSO₂CH₃ | 5-OCH₃ | CH₃ | OCH₃ | |
| CH₂CH₂OSO₂CH₃ | 5-Cl | CH₃ | OCH₃ | |
| CH₂CH₂SH | H | CH₃ | OCH₃ | |

TABLE 8

| R₁ | R₃ | X | Y | Z | m.p. (°C.) |
|---|---|---|---|---|---|
| CH$_2$CH$_2$OH | H | CH$_3$ | CH$_3$ | CH | |
| CH$_2$CH$_2$OH | H | CH$_3$ | OCH$_3$ | CH | |
| CH$_2$CH$_2$OH | H | OCH$_3$ | OCH$_3$ | CH | |
| CH$_2$CH$_2$OH | H | Cl | OCH$_3$ | CH | |
| CH$_2$CH$_2$OH | H | OCH$_3$ | CH(OCH$_3$)$_2$ | CH | |
| CH$_2$CH$_2$OH | H | CH$_3$ | OCH$_3$ | N | |
| CH$_2$CH$_2$OH | H | OCH$_3$ | OCH$_3$ | N | |
| CH$_2$CH$_2$OSO$_2$CH$_3$ | H | CH$_3$ | CH$_3$ | CH | |
| CH$_2$CH$_2$OSO$_2$CH$_3$ | H | CH$_3$ | OCH$_3$ | CH | |
| CH$_2$CH$_2$OSO$_2$CH$_3$ | H | OCH$_3$ | OCH$_3$ | CH | |
| CH$_2$CH$_2$OSO$_2$CH$_3$ | H | Cl | OCH$_3$ | CH | |
| CH$_2$CH$_2$OSO$_2$CH$_3$ | H | OCH$_3$ | CH(OCH$_3$)$_2$ | CH | |
| CH$_2$CH$_2$OSO$_2$CH$_3$ | H | CH$_3$ | OCH$_3$ | N | |
| CH$_2$CH$_2$OSO$_2$CH$_3$ | H | OCH$_3$ | OCH$_3$ | N | |
| CH$_2$CH$_2$OH | 3-Cl | CH$_3$ | CH$_3$ | CH | |
| CH$_2$CH(OH)CH$_3$ | 5-F | CH$_3$ | OCH$_3$ | CH | |
| CH$_2$CH$_2$CH$_2$OSO$_2$CH$_3$ | 5-Cl | OCH$_3$ | OCH$_3$ | CH | |
| CH(CHOH)$_2$ | 5-CH$_3$ | Cl | OCH$_3$ | CH | |
| CH$_2$CH$_2$CH(OH)CH$_3$ | 5-OCH$_3$ | OCH$_3$ | CH(OCH$_3$)$_2$ | CH | |
| CH$_2$CH$_2$N(CH$_3$)$_2$ | 6-Cl | CH$_3$ | OCH$_3$ | N | |
| CH$_2$CH$_2$OCONHCH$_3$ | H | OCH$_3$ | OCH$_3$ | N | |
| CH$_2$CH$_2$OCF$_2$H | H | CH$_3$ | CH$_3$ | CH | |
| CH$_2$CH$_2$OCH$_2$CF$_3$ | H | CH$_3$ | OCH$_3$ | CH | |
| CH$_2$CH$_2$OCF$_2$H | H | OCH$_3$ | OCH$_3$ | CH | |
| CH$_2$CH$_2$SOCH$_3$ | H | Cl | OCH$_3$ | CH | |
| CH$_2$CH$_2$OSO$_2$N(CH$_3$)$_2$ | H | OCH$_3$ | CH(OCH$_3$)$_2$ | CH | |
| CH$_2$CH(OSO$_2$CH$_3$)CH$_3$ | H | CH$_3$ | OCH$_3$ | N | |
| CH$_2$CH(OSO$_2$CH$_3$)CH$_3$ | H | OCH$_3$ | OCH$_3$ | N | |
| CH$_2$CH$_2$SH | H | OCH$_3$ | OCH$_3$ | CH | |

TABLE 9

| R₁ | R₁₆ | X | Y | Z | m.p. (°C.) |
|---|---|---|---|---|---|
| CH$_2$CH$_2$OH | H | CH$_3$ | CH$_3$ | CH | |
| CH$_2$CH$_2$OH | H | CH$_3$ | OCH$_3$ | CH | |
| CH$_2$CH$_2$OH | H | OCH$_3$ | OCH$_3$ | CH | |
| CH$_2$CH$_2$OH | H | Cl | OCH$_3$ | CH | |
| CH$_2$CH$_2$OH | H | OCH$_3$ | CH(OCH$_3$)$_2$ | CH | |
| CH$_2$CH$_2$OH | H | CH$_3$ | OCH$_3$ | N | |
| CH$_2$CH$_2$OH | H | OCH$_3$ | OCH$_3$ | N | |
| CH$_2$CH$_2$OSO$_2$CH$_3$ | H | CH$_3$ | CH$_3$ | CH | |
| CH$_2$CH$_2$OSO$_2$CH$_3$ | H | CH$_3$ | OCH$_3$ | CH | |
| CH$_2$CH$_2$OSO$_2$CH$_3$ | H | OCH$_3$ | OCH$_3$ | CH | |
| CH$_2$CH$_2$OSO$_2$CH$_3$ | H | Cl | OCH$_3$ | CH | |
| CH$_2$CH$_2$OSO$_2$CH$_3$ | H | OCH$_3$ | CH(OCH$_3$)$_2$ | CH | |
| CH$_2$CH$_2$OSO$_2$CH$_3$ | H | CH$_3$ | OCH$_3$ | N | |
| CH$_2$CH$_2$OSO$_2$CH$_3$ | H | OCH$_3$ | OCH$_3$ | N | |
| CH$_2$CH$_2$CH$_2$OH | H | CH$_3$ | CH$_3$ | CH | |
| CH$_2$CH$_2$CH$_2$OSO$_2$CH$_3$ | H | CH$_3$ | OCH$_3$ | CH | |
| CH$_2$CH$_2$CH$_2$OSO$_2$CH$_3$ | H | OCH$_3$ | OCH$_3$ | CH | |
| CH$_2$CH(OH)CH$_3$ | H | Cl | OCH$_3$ | CH | |
| CH$_2$CH(OSO$_2$CH$_3$)CH$_3$ | H | OCH$_3$ | CH(OCH$_3$)$_2$ | CH | |
| CH(CH$_2$OH)CH$_3$ | H | CH$_3$ | OCH$_3$ | N | |
| CH(CH$_2$OSO$_2$CH$_3$)CH$_3$ | H | OCH$_3$ | OCH$_3$ | N | |
| CH$_2$CH$_2$OCF$_2$H | H | CH$_3$ | CH$_3$ | CH | |
| CH$_2$CH$_2$OCF$_2$H | H | CH$_3$ | OCH$_3$ | CH | |
| CH$_2$CH$_2$N(CH$_3$)$_2$ | H | OCH$_3$ | OCH$_3$ | CH | |
| CH$_2$CH$_2$OCONHCH$_3$ | H | Cl | OCH$_3$ | CH | |

TABLE 9-continued

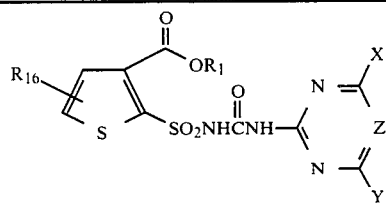

| R₁ | R₁₆ | X | Y | Z | m.p. (°C.) |
|---|---|---|---|---|---|
| CH₂CH₂CH₂CH₂OH | H | OCH₃ | CH(OCH₃)₂ | CH | |
| CH₂CH₂OSO₂CH₂CH₃ | H | CH₃ | OCH₃ | N | |
| CH₂CH₂OPO(OCH₃)₂ | H | OCH₃ | OCH₃ | N | |
| CH₂CH₂OH | 4-CH₃ | CH₃ | CH₃ | CH | |
| CH₂CH₂OH | 4-CH₃ | CH₃ | OCH₃ | CH | |
| CH₂CH₂OH | 4-CH₃ | OCH₃ | OCH₃ | CH | |
| CH₂CH₂OH | 4-CH₃ | Cl | OCH₃ | CH | |
| CH₂CH₂OH | 4-CH₃ | CH₃ | OCH₃ | N | |
| CH₂CH₂OH | 4-CH₃ | OCH₃ | OCH₃ | N | |
| CH₂CH₂OH | 4-Cl | OCH₃ | OCH₃ | CH | |
| CH₂CH₂OH | 4-Cl | CH₃ | OCH₃ | N | |
| CH₂CH₂OH | 4-F | CH₃ | OCH₃ | N | |
| CH₂CH₂OH | 5-CH₃ | CH₃ | OCH₃ | N | |
| CH₂CH₂OH | 5-Cl | CH₃ | OCH₃ | N | |
| CH₂CH₂OH | 5-F | CH₃ | OCH₃ | N | |
| CH₂CH₂OSO₂CH₃ | 4-CH₃ | OCH₃ | OCH₃ | CH | |
| CH₂CH₂OSO₂CH₃ | 4-CH₃ | CH₃ | OCH₃ | N | |
| CH₂CH₂OSO₂CH₃ | 4-Cl | CH₃ | OCH₃ | N | |
| CH₂CH₂SH | H | CH₃ | CH₃ | CH | |
| CH₂CH₂SH | H | CH₃ | OCH₃ | CH | |
| CH₂CH₂SH | H | OCH₃ | OCH₃ | CH | |
| CH₂CH₂SH | H | Cl | OCH₃ | CH | |
| CH₂CH₂SH | H | CH₃ | OCH₃ | N | |
| CH₂CH₂SH | H | OCH₃ | OCH₃ | N | |

TABLE 10

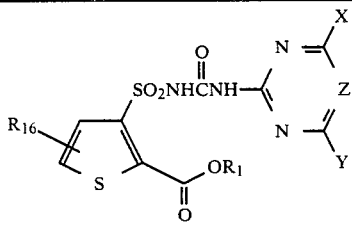

| R₁ | R₁₆ | X | Y | Z | m.p. (°C.) |
|---|---|---|---|---|---|
| CH₂CH₂OH | H | CH₃ | CH₃ | CH | |
| CH₂CH₂OH | H | CH₃ | OCH₃ | CH | |
| CH₂CH₂OH | H | OCH₃ | OCH₃ | CH | |
| CH₂CH₂OH | H | Cl | OCH₃ | CH | |
| CH₂CH₂OH | H | OCH₃ | CH(OCH₃)₂ | CH | |
| CH₂CH₂OH | H | CH₃ | OCH₃ | N | |
| CH₂CH₂OH | H | OCH₃ | OCH₃ | N | |
| CH₂CH₂OSO₂CH₃ | H | CH₃ | CH₃ | CH | |
| CH₂CH₂OSO₂CH₃ | H | CH₃ | OCH₃ | CH | |
| CH₂CH₂OSO₂CH₃ | H | OCH₃ | OCH₃ | CH | |
| CH₂CH₂OSO₂CH₃ | H | Cl | OCH₃ | CH | |
| CH₂CH₂OSO₂CH₃ | H | OCH₃ | CH(OCH₃)₂ | CH | |
| CH₂CH₂OSO₂CH₃ | H | CH₃ | OCH₃ | N | |
| CH₂CH₂OSO₂CH₃ | H | OCH₃ | OCH₃ | N | |
| CH₂CH₂CH₂OH | H | CH₃ | CH₃ | CH | |
| CH₂CH₂CH₂OSO₂CH₃ | H | CH₃ | OCH₃ | CH | |
| CH₂CH₂CH₂OSO₂CH₃ | H | OCH₃ | OCH₃ | CH | |
| CH₂CH(OH)CH₃ | H | Cl | OCH₃ | CH | |
| CH₂CH(OSO₂CH₃)CH₃ | H | OCH₃ | CH(OCH₃)₂ | CH | |
| CH(CH₂OH)CH₃ | H | CH₃ | OCH₃ | N | |
| CH(CH₂OSO₂CH₃)CH₃ | H | OCH₃ | OCH₃ | N | |
| CH₂CH₂OCF₂H | H | CH₃ | CH₃ | CH | |
| CH₂CH₂OCF₂H | H | CH₃ | OCH₃ | CH | |
| CH₂CH₂N(CH₃)₂ | H | OCH₃ | OCH₃ | CH | |
| CH₂CH₂OCONHCH₃ | H | Cl | OCH₃ | CH | |
| CH₂CH₂CH₂CH₂OH | H | OCH₃ | CH(OCH₃)₂ | CH | |
| CH₂CH₂OSO₂CH₂CH₃ | H | CH₃ | OCH₃ | N | |
| CH₂CH₂OPO(OCH₃)₂ | H | OCH₃ | OCH₃ | N | |
| CH₂CH₂OH | 4-CH₃ | CH₃ | CH₃ | CH | |

TABLE 10-continued

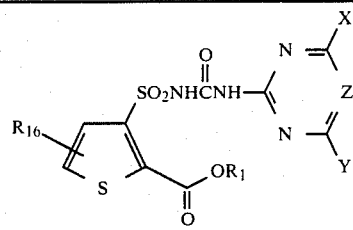

| $R_1$ | $R_{16}$ | X | Y | Z | m.p. (°C.) |
|---|---|---|---|---|---|
| CH₂CH₂OH | 4-CH₃ | CH₃ | OCH₃ | CH | |
| CH₂CH₂OH | 4-CH₃ | OCH₃ | OCH₃ | CH | |
| CH₂CH₂OH | 4-CH₃ | Cl | OCH₃ | CH | |
| CH₂CH₂OH | 4-CH₃ | CH₃ | OCH₃ | N | |
| CH₂CH₂OH | 4-CH₃ | OCH₃ | OCH₃ | N | |
| CH₂CH₂OH | 4-Cl | OCH₃ | OCH₃ | CH | |
| CH₂CH₂OH | 4-Cl | CH₃ | OCH₃ | N | |
| CH₂CH₂OH | 4-F | CH₃ | OCH₃ | N | |
| CH₂CH₂OH | 5-CH₃ | CH₃ | OCH₃ | N | |
| CH₂CH₂OH | 5-Cl | CH₃ | OCH₃ | N | |
| CH₂CH₂OH | 5-F | CH₃ | OCH₃ | N | |
| CH₂CH₂OSO₂CH₃ | 4-CH₃ | OCH₃ | OCH₃ | CH | |
| CH₂CH₂OSO₂CH₃ | 4-CH₃ | CH₃ | OCH₃ | N | |
| CH₂CH₂OSO₂CH₃ | 4-Cl | CH₃ | OCH₃ | N | |
| CH₂CH₂SH | H | CH₃ | CH₃ | CH | |
| CH₂CH₂SH | H | CH₃ | OCH₃ | CH | |
| CH₂CH₂SH | H | OCH₃ | OCH₃ | CH | |
| CH₂CH₂SH | H | Cl | OCH₃ | CH | |
| CH₂CH₂SH | H | CH₃ | OCH₃ | N | |
| CH₂CH₂SH | H | OCH₃ | OCH₃ | N | |

TABLE 11

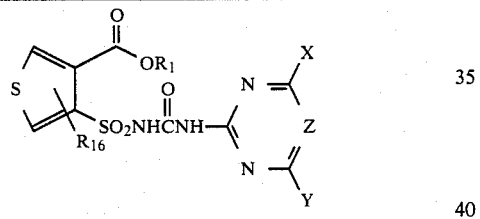

| $R_1$ | $R_{16}$ | X | Y | Z | m.p. (°C.) |
|---|---|---|---|---|---|
| CH₂CH₂OH | H | CH₃ | CH₃ | CH | |
| CH₂CH₂OH | H | CH₃ | OCH₃ | CH | |
| CH₂CH₂OH | H | OCH₃ | OCH₃ | CH | |
| CH₂CH₂OH | H | Cl | OCH₃ | CH | |
| CH₂CH₂OH | H | OCH₃ | CH(OCH₃)₂ | CH | |
| CH₂CH₂OH | H | CH₃ | OCH₃ | N | |
| CH₂CH₂OH | H | OCH₃ | OCH₃ | N | |
| CH₂CH₂OSO₂CH₃ | H | CH₃ | CH₃ | CH | |
| CH₂CH₂OSO₂CH₃ | H | CH₃ | OCH₃ | CH | |
| CH₂CH₂OSO₂CH₃ | H | OCH₃ | OCH₃ | CH | |
| CH₂CH₂OSO₂CH₃ | H | Cl | OCH₃ | CH | |
| CH₂CH₂OSO₂CH₃ | H | OCH₃ | CH(OCH₃)₂ | CH | |
| CH₂CH₂OSO₂CH₃ | H | CH₃ | OCH₃ | N | |
| CH₂CH₂OSO₂CH₃ | H | OCH₃ | OCH₃ | N | |
| CH₂CH₂CH₂OH | H | CH₃ | CH₃ | CH | |
| CH₂CH₂CH₂OSO₂CH₃ | H | CH₃ | CH₃ | CH | |
| CH₂CH₂CH₂OSO₂CH₃ | H | CH₃ | OCH₃ | CH | |
| CH₂CH(OH)CH₃ | H | Cl | OCH₃ | CH | |
| CH₂CH(OSO₂CH₃)CH₃ | H | OCH₃ | CH(OCH₃)₂ | CH | |
| CH(CH₂OH)CH₃ | H | CH₃ | OCH₃ | N | |
| CH(CH₂OSO₂CH₃)CH₃ | H | OCH₃ | OCH₃ | N | |
| CH₂CH₂OCF₂H | H | CH₃ | CH₃ | CH | |
| CH₂CH₂OCF₂H | H | CH₃ | OCH₃ | CH | |
| CH₂CH₂N(CH₃)₂ | H | OCH₃ | OCH₃ | CH | |
| CH₂CH₂OCONHCH₃ | H | Cl | OCH₃ | CH | |
| CH₂CH₂CH₂CH₂OH | H | OCH₃ | CH(OCH₃)₂ | CH | |
| CH₂CH₂OSO₂CH₂CH₃ | H | CH₃ | OCH₃ | N | |
| CH₂CH₂OPO(OCH₃)₂ | H | OCH₃ | OCH₃ | N | |
| CH₂CH₂OH | 2-CH₃ | CH₃ | CH₃ | CH | |
| CH₂CH₂OH | 2-CH₃ | CH₃ | OCH₃ | CH | |
| CH₂CH₂OH | 2-CH₃ | OCH₃ | OCH₃ | CH | |
| CH₂CH₂OH | 2-CH₃ | Cl | OCH₃ | CH | |

TABLE 11-continued

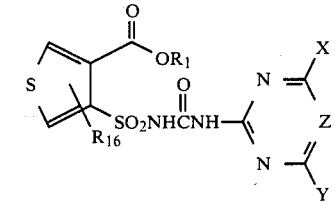

| $R_1$ | $R_{16}$ | X | Y | Z | m.p. (°C.) |
|---|---|---|---|---|---|
| CH₂CH₂OH | 2-CH₃ | CH₃ | OCH₃ | N | |
| CH₂CH₂OH | 2-CH₃ | OCH₃ | OCH₃ | N | |
| CH₂CH₂OH | 2-Cl | OCH₃ | OCH₃ | CH | |
| CH₂CH₂OH | 2-Cl | CH₃ | OCH₃ | N | |
| CH₂CH₂OH | 2-F | CH₃ | OCH₃ | N | |
| CH₂CH₂OH | 5-CH₃ | CH₃ | OCH₃ | N | |
| CH₂CH₂OH | 5-Cl | CH₃ | OCH₃ | N | |
| CH₂CH₂OH | 5-F | CH₃ | OCH₃ | N | |
| CH₂CH₂OSO₂CH₃ | 2-CH₃ | OCH₃ | OCH₃ | CH | |
| CH₂CH₂OSO₂CH₃ | 2-CH₃ | CH₃ | OCH₃ | N | |
| CH₂CH₂OSO₂CH₃ | 2-Cl | CH₃ | OCH₃ | N | |
| CH₂CH₂SH | H | CH₃ | CH₃ | CH | |
| CH₂CH₂SH | H | CH₃ | OCH₃ | CH | |
| CH₂CH₂SH | H | OCH₃ | OCH₃ | CH | |
| CH₂CH₂SH | H | Cl | OCH₃ | CH | |
| CH₂CH₂SH | H | CH₃ | OCH₃ | N | |
| CH₂CH₂SH | H | OCH₃ | OCH₃ | N | |

TABLE 12

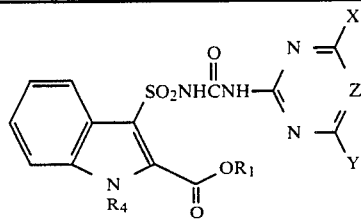

| R₁ | R₄ | X | Y | Z | m.p. (°C.) |
|---|---|---|---|---|---|
| CH₂CH₂OH | H | CH₃ | CH₃ | CH | |
| CH₂CH₂OH | H | CH₃ | OCH₃ | CH | |
| CH₂CH₂OH | H | OCH₃ | OCH₃ | CH | |
| CH₂CH₂OH | H | Cl | OCH₃ | CH | |
| CH₂CH₂OH | CH₃ | OCH₃ | CH(OCH₃)₂ | CH | |
| CH₂CH₂OH | CH₃ | CH₃ | OCH₃ | N | |
| CH₂CH₂OH | CH₃ | OCH₃ | OCH₃ | N | |
| CH₂CH₂OSO₂CH₃ | H | CH₃ | CH₃ | CH | |
| CH₂CH₂OSO₂CH₃ | H | CH₃ | OCH₃ | CH | |
| CH₂CH₂OSO₂CH₃ | H | OCH₃ | OCH₃ | CH | |
| CH₂CH₂OSO₂CH₃ | CH₃ | Cl | OCH₃ | CH | |
| CH₂CH₂OSO₂CH₃ | CH₃ | OCH₃ | CH(OCH₃)₂ | CH | |
| CH₂CH₂OSO₂CH₃ | CH₃ | CH₃ | OCH₃ | N | |
| CH₂CH₂OSO₂CH₃ | CH₃ | OCH₃ | OCH₃ | N | |
| CH₂CH₂CH₂OH | H | CH₃ | CH₃ | CH | |
| CH₂CH₂CH₂OSO₂CH₃ | H | CH₃ | OCH₃ | CH | |
| CH₂CH₂CH₂OSO₂CH₃ | H | OCH₃ | OCH₃ | CH | |
| CH₂CH(OH)CH₃ | CH₃ | Cl | OCH₃ | CH | |
| CH₂CH(OSO₂CH₃)CH₃ | CH₃ | OCH₃ | CH(OCH₃)₂ | CH | |

TABLE 12-continued

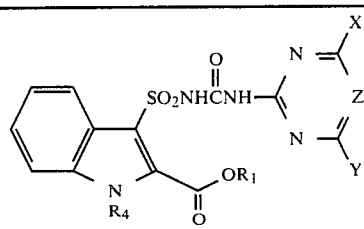

| R₁ | R₄ | X | Y | Z | m.p. (°C.) |
|---|---|---|---|---|---|
| CH(CH₂OH)CH₃ | CH₃ | CH₃ | OCH₃ | N | |
| CH(CH₂OSO₂CH₃)CH₃ | CH₃ | OCH₃ | OCH₃ | N | |
| CH₂CH₂OCF₂H | H | CH₃ | CH₃ | CH | |
| CH₂CH₂OCF₂H | H | CH₃ | OCH₃ | CH | |
| CH₂CH₂N(CH₃)₂ | H | OCH₃ | OCH₃ | CH | |
| CH₂CH₂OCONHCH₃ | H | Cl | OCH₃ | CH | |
| CH₂CH₂CH₂CH₂OH | CH₃ | OCH₃ | CH(OCH₃)₂ | CH | |
| CH₂CH₂OSO₂CH₂CH₃ | CH₃ | CH₃ | OCH₃ | N | |
| CH₂CH₂OPO(OCH₃)₂ | CH₃ | OCH₃ | OCH₃ | N | |
| CH₂CH₂SH | CH₃ | OCH₃ | OCH₃ | CH | |
| CH₂CH₂SH | CH₃ | CH₃ | OCH₃ | CH | |
| CH₂CH₂SH | CH₃ | Cl | OCH₃ | CH | |
| CH₂CH₂SH | CH₃ | CH₃ | OCH₃ | N | |
| CH₂CH₂SH | H | CH₃ | OCH₃ | CH | |
| CH₂CH₂SH | H | OCH₃ | OCH₃ | CH | |
| CH₂CH₂SH | H | CH₃ | OCH₃ | N | |
| CH₂CH₂SCOCH₃ | H | CH₃ | OCH₃ | N | |
| CH₂CH₂SCOCH₃ | H | CH₃ | OCH₃ | CH | |

TABLE 13

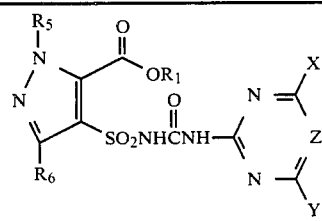

| R₁ | R₅ | R₆ | X | Y | Z | m.p. (°C.) |
|---|---|---|---|---|---|---|
| CH₂CH₂OH | H | H | CH₃ | CH₃ | CH | |
| CH₂CH₂OH | H | H | CH₃ | OCH₃ | CH | |
| CH₂CH₂OH | H | H | OCH₃ | OCH₃ | CH | |
| CH₂CH₂OH | CH₃ | H | CH₃ | CH₃ | CH | |
| CH₂CH₂OH | CH₃ | H | CH₃ | OCH₃ | CH | |
| CH₂CH₂OH | CH₃ | H | OCH₃ | OCH₃ | CH | |
| CH₂CH₂OSO₂CH₃ | H | CH₃ | CH₃ | CH₃ | CH | |
| CH₂CH₂OSO₂CH₃ | H | CH₃ | CH₃ | OCH₃ | CH | |
| CH₂CH₂OSO₂CH₃ | H | CH₃ | OCH₃ | OCH₃ | CH | |
| CH₂CH₂OSO₂CH₃ | CH₃ | CH₃ | CH₃ | CH₃ | CH | |
| CH₂CH₂OSO₂CH₃ | CH₃ | CH₃ | CH₃ | OCH₃ | CH | |
| CH₂CH₂OSO₂CH₃ | CH₃ | CH₃ | OCH₃ | OCH₃ | CH | |
| CH₂CH₂CH₂OSO₂CH₃ | H | H | Cl | OCH₃ | CH | |
| CH₂CH(OSO₂CH₃)CH₃ | CH₃ | H | Cl | OCH₃ | CH | |
| CH₂CH₂N(CH₃)₂ | H | CH₃ | Cl | OCH₃ | CH | |
| CH₂CH₂SOCH₃ | CH₃ | CH₃ | Cl | OCH₃ | CH | |
| CH₂CH₂OCF₂H | H | H | CH₃ | OCH₃ | N | |
| CH₂CH(OH)CH₂OH | H | H | OCH₃ | OCH₃ | N | |
| CH₂CH₂CH₂CH₂OSO₂CH₃ | H | CH₃ | CH₃ | OCH₃ | N | |
| CH₂CH₂OSi(CH₃)₃ | H | CH₃ | OCH₃ | OCH₃ | N | |
| CH₂CH₂OPO(OCH₃)₂ | CH₃ | H | CH₃ | OCH₃ | N | |
| CH₂CH₂OCONHCH₃ | CH₃ | H | OCH₃ | OCH₃ | N | |
| CH₂CH₂OSO₂CH₂CH₃ | CH₃ | CH₃ | CH₃ | OCH₃ | N | |
| CH₂CH₂CH(OH)CH₃ | CH₃ | CH₃ | OCH₃ | OCH₃ | N | |
| CH₂CH₂OH | CH₂CH₃ | H | CH₃ | OCH₃ | CH | |
| CH₂CH₂OH | CH₂CH₃ | H | OCH₃ | OCH₃ | CH | |
| CH₂CH₂OH | CH₂CH₂CH₃ | H | CH₃ | OCH₃ | CH | |
| CH₂CH₂OH | CH₂CH₂CH₃ | H | OCH₃ | OCH₃ | CH | |
| CH₂CH₂OH | CH₂CH=CH₂ | H | CH₃ | OCH₃ | CH | |
| CH₂CH₂OH | CH₂CH=CH₂ | H | OCH₃ | OCH₃ | CH | |
| CH₂CH₂OH | C₆H₅ | H | CH₃ | OCH₃ | CH | |
| CH₂CH₂OH | C₆H₅ | H | OCH₃ | OCH₃ | CH | |
| CH₂CH₂OH | CH₃ | CH₂CH₃ | CH₃ | OCH₃ | CH | |

TABLE 13-continued

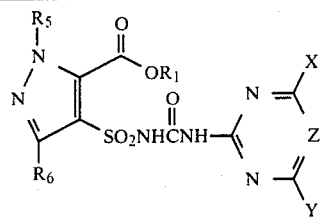

| $R_1$ | $R_5$ | $R_6$ | X | Y | Z | m.p. (°C.) |
|---|---|---|---|---|---|---|
| $CH_2CH_2OH$ | $CH_3$ | $CH_2CH_3$ | $OCH_3$ | $OCH_3$ | CH | |
| $CH_2CH_2OH$ | $CH_3$ | $CH_2CH_2CH_3$ | $CH_3$ | $OCH_3$ | CH | |
| $CH_2CH_2OH$ | $CH_3$ | $CH_2CH_2CH_3$ | $OCH_3$ | $OCH_3$ | CH | |
| $CH_2CH_2SH$ | $CH_3$ | $CH_3$ | $CH_3$ | $OCH_3$ | CH | |
| $CH_2CH_2SH$ | $CH_3$ | $CH_3$ | $OCH_3$ | $OCH_3$ | CH | |

TABLE 14

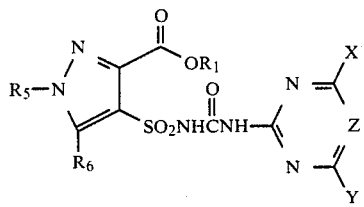

| $R_1$ | $R_5$ | $R_6$ | X | Y | Z | m.p. (°C.) |
|---|---|---|---|---|---|---|
| $CH_2CH_2OH$ | H | H | $CH_3$ | $CH_3$ | CH | |
| $CH_2CH_2OH$ | H | H | $CH_3$ | $OCH_3$ | CH | |
| $CH_2CH_2OH$ | H | H | $OCH_3$ | $OCH_3$ | CH | |
| $CH_2CH_2OH$ | $CH_3$ | H | $CH_3$ | $CH_3$ | CH | |
| $CH_2CH_2OH$ | $CH_3$ | H | $CH_3$ | $OCH_3$ | CH | |
| $CH_2CH_2OH$ | $CH_3$ | H | $OCH_3$ | $OCH_3$ | CH | |
| $CH_2CH_2OSO_2CH_3$ | H | $CH_3$ | $CH_3$ | $CH_3$ | CH | |
| $CH_2CH_2OSO_2CH_3$ | H | $CH_3$ | $CH_3$ | $OCH_3$ | CH | |
| $CH_2CH_2OSO_2CH_3$ | H | $CH_3$ | $OCH_3$ | $OCH_3$ | CH | |
| $CH_2CH_2OSO_2CH_3$ | $CH_3$ | $CH_3$ | $CH_3$ | $CH_3$ | CH | |
| $CH_2CH_2OSO_2CH_3$ | $CH_3$ | $CH_3$ | $CH_3$ | $OCH_3$ | CH | |
| $CH_2CH_2OSO_2CH_3$ | $CH_3$ | $CH_3$ | $OCH_3$ | $OCH_3$ | CH | |
| $CH_2CH_2CH_2OSO_2CH_3$ | H | H | Cl | $OCH_3$ | CH | |
| $CH_2CH(OSO_2CH_3)CH_3$ | $CH_3$ | H | Cl | $OCH_3$ | CH | |
| $CH_2CH_2N(CH_3)_2$ | H | $CH_3$ | Cl | $OCH_3$ | CH | |
| $CH_2CH_2SOCH_3$ | $CH_3$ | $CH_3$ | Cl | $OCH_3$ | CH | |
| $CH_2CH_2OCF_2H$ | H | H | $CH_3$ | $OCH_3$ | N | |
| $CH_2CH(OH)CH_2OH$ | H | H | $OCH_3$ | $OCH_3$ | N | |
| $CH_2CH_2CH_2CH_2OSO_2CH_3$ | H | $CH_3$ | $CH_3$ | $OCH_3$ | N | |
| $CH_2CH_2OSi(CH_3)_3$ | H | $CH_3$ | $OCH_3$ | $OCH_3$ | N | |
| $CH_2CH_2OPO(OCH_3)_2$ | $CH_3$ | H | $CH_3$ | $OCH_3$ | N | |
| $CH_2CH_2OCONHCH_3$ | $CH_3$ | H | $OCH_3$ | $OCH_3$ | N | |
| $CH_2CH_2OSO_2CH_2CH_3$ | $CH_3$ | $CH_3$ | $CH_3$ | $OCH_3$ | N | |
| $CH_2CH_2CH(OH)CH_3$ | $CH_3$ | $CH_3$ | $OCH_3$ | $OCH_3$ | N | |
| $CH_2CH_2OH$ | $CH_2CH_3$ | H | $CH_3$ | $OCH_3$ | CH | |
| $CH_2CH_2OH$ | $CH_2CH_3$ | H | $OCH_3$ | $OCH_3$ | CH | |
| $CH_2CH_2OH$ | $CH_2CH_2CH_3$ | H | $CH_3$ | $OCH_3$ | CH | |
| $CH_2CH_2OH$ | $CH_2CH_2CH_3$ | H | $OCH_3$ | $OCH_3$ | CH | |
| $CH_2CH_2OH$ | $CH_2CH=CH_2$ | H | $CH_3$ | $OCH_3$ | CH | |
| $CH_2CH_2OH$ | $CH_2CH=CH_2$ | H | $OCH_3$ | $OCH_3$ | CH | |
| $CH_2CH_2OH$ | $C_6H_5$ | H | $CH_3$ | $OCH_3$ | CH | |
| $CH_2CH_2OH$ | $C_6H_5$ | H | $OCH_3$ | $OCH_3$ | CH | |
| $CH_2CH_2OH$ | $CH_3$ | $CH_2CH_3$ | $CH_3$ | $OCH_3$ | CH | |
| $CH_2CH_2OH$ | $CH_3$ | $CH_2CH_3$ | $OCH_3$ | $OCH_3$ | CH | |
| $CH_2CH_2OH$ | $CH_3$ | $CH_2CH_2CH_3$ | $CH_3$ | $OCH_3$ | CH | |
| $CH_2CH_2OH$ | $CH_3$ | $CH_2CH_2CH_3$ | $OCH_3$ | $OCH_3$ | CH | |
| $CH_2CH_2SH$ | $CH_3$ | $CH_3$ | $CH_3$ | $OCH_3$ | CH | |
| $CH_2CH_2SH$ | $CH_3$ | $CH_3$ | $OCH_3$ | $OCH_3$ | CH | |

TABLE 15

| $R_1$ | $R_5$ | $R_6$ | X | Y | Z | m.p. (°C.) |
|---|---|---|---|---|---|---|
| CH₂CH₂OH | H | H | CH₃ | CH₃ | CH | |
| CH₂CH₂OH | H | H | CH₃ | OCH₃ | CH | |
| CH₂CH₂OH | H | H | OCH₃ | OCH₃ | CH | |
| CH₂CH₂OH | CH₃ | H | CH₃ | CH₃ | CH | |
| CH₂CH₂OH | CH₃ | H | CH₃ | OCH₃ | CH | |
| CH₂CH₂OH | CH₃ | H | OCH₃ | OCH₃ | CH | |
| CH₂CH₂OSO₂CH₃ | H | CH₃ | CH₃ | CH₃ | CH | |
| CH₂CH₂OSO₂CH₃ | H | CH₃ | CH₃ | OCH₃ | CH | |
| CH₂CH₂OSO₂CH₃ | H | CH₃ | OCH₃ | OCH₃ | CH | |
| CH₂CH₂OSO₂CH₃ | CH₃ | CH₃ | CH₃ | CH₃ | CH | |
| CH₂CH₂OSO₂CH₃ | CH₃ | CH₃ | CH₃ | OCH₃ | CH | |
| CH₂CH₂OSO₂CH₃ | CH₃ | CH₃ | OCH₃ | OCH₃ | CH | |
| CH₂CH₂CH₂OSO₂CH₃ | H | H | Cl | OCH₃ | CH | |
| CH₂CH(OSO₂CH₃)CH₃ | CH₃ | H | Cl | OCH₃ | CH | |
| CH₂CH₂N(CH₃)₂ | H | CH₃ | Cl | OCH₃ | CH | |
| CH₂CH₂SOCH₃ | CH₃ | CH₃ | Cl | OCH₃ | CH | |
| CH₂CH₂OCF₂H | H | H | CH₃ | OCH₃ | N | |
| CH₂CH(OH)CH₂OH | H | H | OCH₃ | OCH₃ | N | |
| CH₂CH₂CH₂CH₂OSO₂CH₃ | H | CH₃ | CH₃ | OCH₃ | N | |
| CH₂CH₂OSi(CH₃)₃ | H | CH₃ | OCH₃ | OCH₃ | N | |
| CH₂CH₂OPO(OCH₃)₂ | CH₃ | H | CH₃ | OCH₃ | N | |
| CH₂CH₂OCONHCH₃ | CH₃ | H | OCH₃ | OCH₃ | N | |
| CH₂CH₂OSO₂CH₂CH₃ | CH₃ | CH₃ | CH₃ | OCH₃ | N | |
| CH₂CH₂CH(OH)CH₃ | CH₃ | CH₃ | OCH₃ | OCH₃ | N | |
| CH₂CH₂OH | CH₂CH₃ | H | CH₃ | OCH₃ | CH | |
| CH₂CH₂OH | CH₂CH₃ | H | OCH₃ | OCH₃ | CH | |
| CH₂CH₂OH | CH₂CH₂CH₃ | H | CH₃ | OCH₃ | CH | |
| CH₂CH₂OH | CH₂CH₂CH₃ | H | OCH₃ | OCH₃ | CH | |
| CH₂CH₂OH | CH₂CH=CH₂ | H | CH₃ | OCH₃ | CH | |
| CH₂CH₂OH | CH₂CH=CH₂ | H | OCH₃ | OCH₃ | CH | |
| CH₂CH₂OH | C₆H₅ | H | CH₃ | OCH₃ | CH | |
| CH₂CH₂OH | C₆H₅ | H | OCH₃ | OCH₃ | CH | |
| CH₂CH₂OH | CH₃ | CH₂CH₃ | CH₃ | OCH₃ | CH | |
| CH₂CH₂OH | CH₃ | CH₂CH₃ | OCH₃ | OCH₃ | CH | |
| CH₂CH₂OH | CH₃ | CH₂CH₂CH₃ | CH₃ | OCH₃ | CH | |
| CH₂CH₂OH | CH₃ | CH₂CH₂CH₃ | OCH₃ | OCH₃ | CH | |
| CH₂CH₂SH | CH₃ | CH₃ | CH₃ | OCH₃ | CH | |
| CH₂CH₂SH | CH₃ | CH₃ | OCH₃ | OCH₃ | CH | |

TABLE 16

| $R_1$ | $R_5$ | $R_6$ | X | Y | Z | m.p. (°C.) |
|---|---|---|---|---|---|---|
| CH₂CH₂OH | H | H | CH₃ | CH₃ | CH | |
| CH₂CH₂OH | H | H | CH₃ | OCH₃ | CH | |
| CH₂CH₂OH | H | H | OCH₃ | OCH₃ | CH | |
| CH₂CH₂OH | CH₃ | H | CH₃ | CH₃ | CH | |
| CH₂CH₂OH | CH₃ | H | CH₃ | OCH₃ | CH | |
| CH₂CH₂OH | CH₃ | H | OCH₃ | OCH₃ | CH | |
| CH₂CH₂OSO₂CH₃ | H | CH₃ | CH₃ | CH₃ | CH | |
| CH₂CH₂OSO₂CH₃ | H | CH₃ | CH₃ | OCH₃ | CH | |
| CH₂CH₂OSO₂CH₃ | H | CH₃ | OCH₃ | OCH₃ | CH | |
| CH₂CH₂OSO₂CH₃ | CH₃ | CH₃ | CH₃ | CH₃ | CH | |
| CH₂CH₂OSO₂CH₃ | CH₃ | CH₃ | CH₃ | OCH₃ | CH | |
| CH₂CH₂OSO₂CH₃ | CH₃ | CH₃ | OCH₃ | OCH₃ | CH | |
| CH₂CH₂CH₂OSO₂CH₃ | H | H | Cl | OCH₃ | CH | |
| CH₂CH(OSO₂CH₃)CH₃ | CH₃ | H | Cl | OCH₃ | CH | |

TABLE 16-continued

| R1 | R5 | R6 | X | Y | Z | m.p. (°C.) |
|---|---|---|---|---|---|---|
| CH2CH2N(CH3)2 | H | CH3 | Cl | OCH3 | CH | |
| CH2CH2SOCH3 | CH3 | CH3 | Cl | OCH3 | CH | |
| CH2CH2OCF2H | H | H | CH3 | OCH3 | N | |
| CH2CH(OH)CH2OH | H | H | OCH3 | OCH3 | N | |
| CH2CH2CH2CH2OSO2CH3 | H | CH3 | CH3 | OCH3 | N | |
| CH2CH2OSi(CH3)3 | H | CH3 | OCH3 | OCH3 | N | |
| CH2CH2OPO(OCH3)2 | CH3 | H | CH3 | OCH3 | N | |
| CH2CH2OCONHCH3 | CH3 | H | OCH3 | OCH3 | N | |
| CH2CH2OSO2CH2CH3 | CH3 | CH3 | CH3 | OCH3 | N | |
| CH2CH2CH(OH)CH3 | CH3 | CH3 | OCH3 | OCH3 | N | |
| CH2CH2OH | CH2CH3 | H | CH3 | OCH3 | CH | |
| CH2CH2OH | CH2CH3 | H | OCH3 | OCH3 | CH | |
| CH2CH2OH | CH2CH2CH3 | H | CH3 | OCH3 | CH | |
| CH2CH2OH | CH2CH2CH3 | H | OCH3 | OCH3 | CH | |
| CH2CH2OH | CH2CH=CH2 | H | CH3 | OCH3 | CH | |
| CH2CH2OH | CH2CH=CH2 | H | OCH3 | OCH3 | CH | |
| CH2CH2OH | C6H5 | H | CH3 | OCH3 | CH | |
| CH2CH2OH | C6H5 | H | OCH3 | OCH3 | CH | |
| CH2CH2OH | CH3 | CH2CH3 | CH3 | OCH3 | CH | |
| CH2CH2OH | CH3 | CH2CH3 | OCH3 | OCH3 | CH | |
| CH2CH2OH | CH3 | CH2CH2CH3 | CH3 | OCH3 | CH | |
| CH2CH2OH | CH3 | CH2CH2CH3 | OCH3 | OCH3 | CH | |
| CH2CH2SH | CH3 | CH3 | CH3 | OCH3 | CH | |
| CH2CH2SH | CH3 | CH3 | OCH3 | OCH3 | CH | |

TABLE 17

| R1 | R2 | X | Y | Z | m.p. (°C.) |
|---|---|---|---|---|---|
| CH2CH2OH | 3-Cl | CH3 | OCH3 | N | |
| CH2CH2OH | 5-Cl | CH3 | CH3 | CH | 153–155(d) |
| CH2CH2OH | 5-Cl | CH3 | OCH3 | CH | 92–95(d) |
| CH2CH2OH | 5-Cl | OCH3 | OCH3 | CH | 95–98(d) |
| CH2CH2OH | 5-Cl | Cl | OCH3 | CH | 101–104(d) |
| CH2CH2OH | 5-Cl | CH3 | OCH3 | N | 143–146(d) |
| CH2CH2OH | 5-Cl | OCH3 | OCH3 | N | 108–111(d) |
| CH2CH2OH | 6-Cl | CH3 | OCH3 | N | |
| CH2CH2OH | 3-F | CH3 | OCH3 | N | |
| CH2CH2OH | 5-F | CH3 | OCH3 | N | |
| CH2CH2OH | 6-F | CH3 | OCH3 | N | |
| CH2CH2OH | 5-Br | CH3 | OCH3 | N | |
| CH2CH2OH | 5-CH3 | CH3 | CH3 | CH | |
| CH2CH2OH | 5-CH3 | Cl | OCH3 | CH | |
| CH2CH2OH | 5-CH3 | CH3 | OCH3 | N | |
| CH2CH2OH | 5-CH2CH3 | CH3 | OCH3 | N | |
| CH2CH2OH | 5-CF3 | CH3 | OCH3 | N | |
| CH2CH2OH | 5-CF3 | OCH2CF3 | OCH3 | N | |
| CH2CH2OH | 5-OCH3 | CH3 | CH3 | CH | |
| CH2CH2OH | 5-OCH3 | Cl | OCH3 | CH | |
| CH2CH2OH | 5-OCH3 | CH3 | OCH3 | N | |
| CH2CH2OH | 5-CH2CH3 | CH3 | OCH3 | N | |
| CH2CH2OH | 5-SCH3 | CH3 | OCH3 | N | 98–101(d) |
| CH2CH2OH | 5-SCH2CH3 | CH3 | OCH3 | N | |
| CH2CH2OH | 5-OCF2H | CH3 | OCH3 | N | |
| CH2CH2OH | 5-SCF2H | CH3 | OCH3 | N | |
| CH2CH2OSO2CH3 | 5-Cl | Cl | OCH3 | CH | |
| CH2CH2OSO2CH3 | 5-OCH3 | CH3 | OCH3 | N | |
| CH2CH2OCOCH3 | 5-Cl | CH3 | OCH3 | N | |

TABLE 17-continued

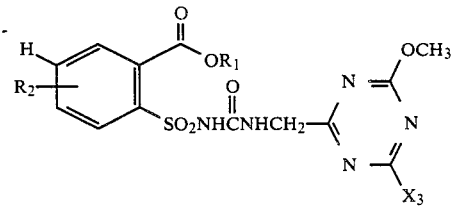

| R₁ | R₂ | X | Y | Z | m.p. (°C.) |
|---|---|---|---|---|---|
| CH₂CH₂OCON(CH₃)₂ | 5-OCH₃ | CH₃ | OCH₃ | N | |
| CH₂CH₂OSO₂N(CH₃₂ | 5-CF₃ | OCH₃ | OCH₃ | CH | |
| CH₂CH₂OCO₂CH₃ | 5-OCH₅ | OCH₃ | OCH₃ | N | |
| CH₂CH₂SOCH₃ | 5-SCH₃ | CH₃ | CH₃ | CH | |
| CH₂CH₂OCH₂CF₃ | 5-OCH₃ | CH₃ | OCH₃ | N | |
| CH₂CH₂OCSNHCH₃ | 3-F | CH₃ | OCH₃ | CH | |
| CH₂CH₂OCONHCH₃ | 6-F | CH₃ | CH₃ | CH | |
| CH₂CH₂OPO(OC₂H₃)₂ | 5-Cl | CH₃ | OCH₃ | N | |
| CH₂CH₂OSi(CH₃)₃ | 5-Cl | CH₃ | OCH₃ | N | |
| CH₂CH₂N(CH₃)₂ | 5-Br | CH₃ | OCH₃ | CH | |
| CH₂CH₂CH₂OH | 5-CH₃ | CH₃ | OCH₃ | N | |
| CH₂CH₂CH₂OSO₂CH₃ | 5-OCH₃ | CH₃ | OCH₃ | N | |
| CH₂CH(OH)CH₃ | 5-CF₃ | CH₃ | OCH₃ | CH | |
| CH₂CH₂CH₂CH₂OH | 5-CF₃ | OCH₃ | OCH₃ | CH | |
| CH₂CH₂OH | 5-Cl | OCH₂CH₃ | NHCH₃ | N | 134–136(d) |
| CH₂CH₂OH | 5-SCH₃ | CH₃ | CH₃ | CH | 98–102(d) |
| CH₂CH₂OH | 5-SCH₃ | CH₃ | OCH₃ | CH | 128–131(d) |
| CH₂CH₂OH | 5-SCH₃ | OCH₃ | OCH₃ | CH | 103–106(d) |
| CH₂CH₂OH | 5-SCH₃ | Cl | OCH₃ | CH | 100–103(d) |
| CH₂CH₂OH | 5-SCH₃ | OCH₃ | OCH₃ | N | 135–137(d) |
| CH₂CH₂OH | 5-SCH₃ | OCH₂CH₃ | NHCH₃ | N | |
| CH₂CH₂OH | 5-OCH₃ | CH₃ | OCH₃ | CH | |
| CH₂CH₂OH | 5-OCH₃ | OCH₃ | OCH₃ | CH | |
| CH₂CH₂OH | 5-OCH₃ | OCH₃ | OCH₃ | N | |
| CH₂CH₂OH | 5-OCH₃ | OCH₂CH₃ | NHCH₃ | N | |
| CH₂CH₂OH | 5-OCH₃ | OCH₃ | N(CH₃)₂ | N | |
| CH₂CH₂OH | 5-CH₃ | CH₃ | OCH₃ | CH | |
| CH₂CH₂OH | 5-CH₃ | OCH₃ | OCH₃ | CH | |
| CH₂CH₂OH | 5-CH₃ | OCH₃ | OCH₃ | N | |
| CH₂CH₂OH | 5-CH₂OCH₃ | CH₃ | CH₃ | CH | |
| CH₂CH₂OH | 5-CH₂OCH₃ | CH₃ | OCH₃ | CH | |
| CH₂CH₂OH | 5-CH₂OCH₃ | OCH₃ | OCH₃ | CH | |
| CH₂CH₂OH | 5-CH₂OCH₃ | Cl | OCH₃ | CH | |
| CH₂CH₂OH | 5-CH₂OCH₃ | CH₃ | OCH₃ | N | |
| CH₂CH₂OH | 5-CH₂OCH₃ | OCH₃ | OCH₃ | N | |
| CH₂CH₂OH | 5-CH₂SCH₃ | CH₃ | CH₃ | CH | |
| CH₂CH₂OH | 5-CH₂SCH₃ | CH₃ | OCH₃ | CH | |
| CH₂CH₂OH | 5-CH₂SCH₃ | OCH₃ | OCH₃ | CH | |
| CH₂CH₂OH | 5-CH₂SCH₃ | Cl | OCH₃ | CH | |
| CH₂CH₂OH | 5-CH₂SCH₃ | CH₃ | OCH₃ | N | |
| CH₂CH₂OH | 5-CH₂SCH₃ | OCH₃ | OCH₃ | N | |
| CH₂CH₂SH | 5-OCH₃ | OCH₃ | OCH₃ | CH | |
| CH₂CH₂SH | 5-OCH₃ | Cl | OCH₃ | CH | |
| CH₂CH₂SH | 5-OCH₃ | CH₃ | OCH₃ | N | |
| CH₂CH₂SH | 5-Cl | OCH₃ | OCH₃ | CH | |
| CH₂CH₂SH | 5-Cl | CH₃ | OCH₃ | N | |
| CH₂CH₂SH | 5-SCH₃ | OCH₃ | OCH₃ | CH | |
| CH₂CH₂SH | 5-SCH₃ | CH₃ | OCH₃ | N | |

TABLE 18

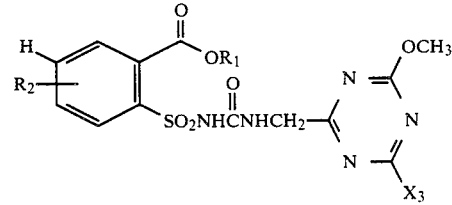

| R₁ | R₂ | X₃ | m.p. (°C.) |
|---|---|---|---|
| CH₂CH₂OH | H | CH₃ | |
| CH₂CH₂OH | H | OCH₃ | |
| CH₂CH₂OSO₂CH₃ | H | OCH₃ | |
| CH₂CH₂OSO₂CH₃ | H | CH₃ | |
| CH₂CH(OH)CH₃ | H | CH₃ | |
| CH₂CH(OH)CH₃ | H | OCH₃ | |

TABLE 18-continued

| R₁ | R₂ | X₃ | m.p. (°C.) |
|---|---|---|---|
| CH₂CH₂OH | 3-Cl | OCH₃ | |
| CH₂CH₂OH | 5-Cl | OCH₃ | |
| CH₂CH₂OH | 5-CH₃ | OCH₃ | |
| CH₂CH₂OH | 5-OCH₃ | OCH₃ | |
| CH₂CH₂OH | 5-SCH₃ | OCH₃ | |
| CH₂CH₂OH | 5-CH₂OCH₃ | OCH₃ | |

TABLE 18-continued

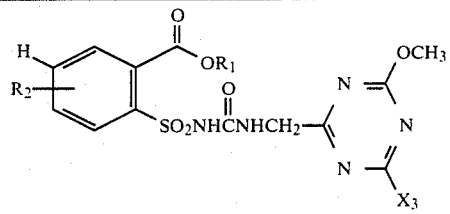

| R₁ | R₂ | X₃ | m.p. (°C.) |
|---|---|---|---|
| CH₂CH₂OH | 6-Cl | OCH₃ | |
| CH₂CH₂SH | H | CH₃ | |
| CH₂CH₂SH | H | OCH₃ | |

TABLE 19

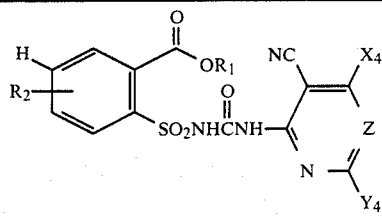

| R₁ | R₂ | X₄ | Y₄ | Z | m.p. (°C.) |
|---|---|---|---|---|---|
| CH₂CH₂OH | H | CH₃ | CH₃ | CH | |
| CH₂CH₂OH | H | CH₃ | CH₃ | N | |
| CH₂CH₂OH | H | CH₃ | OCH₃ | CH | |
| CH₂CH₂OH | H | CH₃ | OCH₃ | N | |
| CH₂CH₂OH | H | OCH₃ | CH₃ | CH | |
| CH₂CH₂OH | H | OCH₃ | CH₃ | N | |
| CH₂CH₂OH | H | Cl | CH₃ | N | |
| CH₂CH₂OH | H | CH₃ | Cl | CH | |
| CH₂CH₂OH | H | CH₂OCH₃ | CH₃ | CH | |
| CH₂CH₂OSO₂CH₃ | H | CH₃ | CH₃ | CH | |
| CH₂CH₂OSO₂CH₃ | H | CH₃ | CH₃ | N | |
| CH₂CH₂OH | 5-Cl | CH₃ | CH₃ | N | |
| CH₂CH₂OH | 5-Cl | CH₃ | CH₃ | CH | |
| CH₂CH₂OH | 5-OCH₃ | CH₃ | CH₃ | N | |
| CH₂CH₂OH | 5-OCH₃ | CH₃ | CH₃ | CH | |
| CH₂CH₂OH | 5-SCH₃ | CH₃ | CH₃ | N | |
| CH₂CH₂OH | 5-SCH₃ | CH₃ | CH₃ | CH | |
| CH₂CH₂OH | 5-CF₃ | CH₃ | CH₃ | CH | |
| CH₂CH₂OH | 5-CH₃ | CH₃ | CH₃ | CH | |
| CH₂CH₂OH | 5-CH₂OCH₃ | CH₃ | CH₃ | CH | |

TABLE 20

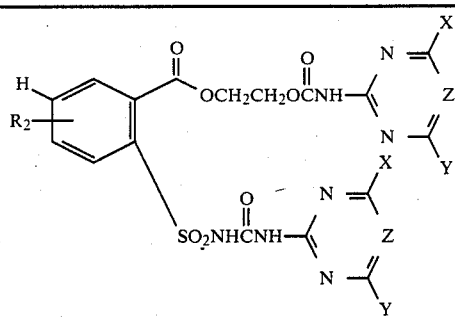

| R₂ | X | Y | Z | m.p. (°C.) |
|---|---|---|---|---|
| H | CH₃ | CH₃ | CH | |
| H | CH₃ | OCH₃ | CH | |
| H | OCH₃ | OCH₃ | CH | |
| H | Cl | OCH₃ | CH | 130(d) |
| H | CH₃ | CH₃ | N | |
| H | CH₃ | OCH₃ | N | |
| H | OCH₃ | OCH₃ | N | |
| H | OCH₃ | N(CH₃)₂ | N | |

TABLE 20-continued

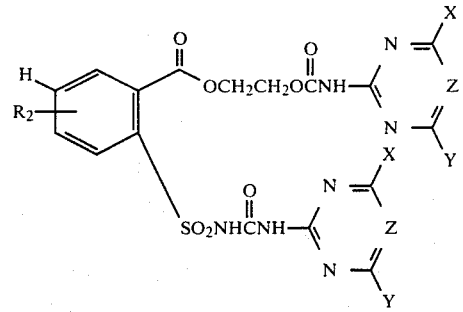

| R₂ | X | Y | Z | m.p. (°C.) |
|---|---|---|---|---|
| H | OCH₂CH₃ | NHCH₃ | N | |
| 5-Cl | OCH₃ | OCH₃ | CH | |
| 5-OCH₃ | OCH₃ | OCH₃ | CH | |
| 5-SCH₃ | OCH₃ | OCH₃ | CH | |
| 5-CH₂OCH₃ | OCH₃ | OCH₃ | CH | |
| 3-Cl | OCH₃ | OCH₃ | CH | |
| 6-Cl | OCH₃ | OCH₃ | CH | |
| 5-CH₃ | OCH₃ | OCH₃ | CH | |
| 5-CF₃ | OCH₃ | OCH₃ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 21

| | Active Ingredient | Weight Percent* | |
|---|---|---|---|
| | | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 6

Wettable Powder

2-[[(4,6-dimethylpyrimidin-2-yl)aminocarbonyl-]aminosulfonyl]benzoic acid, 2-hydroxyethyl ester: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 7

Wettable Powder

2-[[(4,6-dimethylpyrimidin-2-yl)aminocarbonyl-]aminosulfonyl]benzoic acid, 2-hydroxyethyl ester: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 8

Granule

Wettable Powder of Example 7: 5%
attapulgite granules (U.S.S. 20–40 mesh; 0.84–0.42 mm): 95%

A slurry of wettable powder containing 25% solids is sprayed on the surface of attapulgite granules while tumbling in a double-cone blender. The granules are dried and packaged.

EXAMPLE 9

Extruded Pellet

2-[[(4,6-dimethylpyrimidin-2-yl)aminocarbonyl-]aminosulfonyl]benzoic acid, 2-hydroxyethyl ester: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Oil Suspension

2-[[(4,6-dimethylpyrimidin-2-yl)aminocarbonyl-]aminosulfonyl]benzoic acid, 2-hydroxyethyl ester: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 11

Wettable Powder

2-[[(4,6-dimethylpyrimidin-2-yl)aminocarbonyl-]aminosulfonyl]benzoic acid, 2-hydroxyethyl ester: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 12

Low Strength Granule

2-[[(4,6-dimethylpyrimidin-2-yl)aminocarbonyl-]aminosulfonyl]benzoic acid, 2-hydroxyethyl ester: 1%
N,N-dimethylformamide: 9% attapulgite granules (U.S.S. 20–40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 13

Aqueous Suspension

2-[[(4,6-dimethylpyrimidin-2-yl)aminocarbonyl-]aminosulfonyl]benzoic acid, 2-hydroxyethyl ester: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 14

Solution

2-[[(4,6-dimethylpyrimidin-2-yl)aminocarbonyl-]aminosulfonyl]benzoic acid, 2-hydroxyethyl ester, sodium salt: 5%
water: 95%

The salt is added directly to the water with stirring to produce the solution, which may then be packaged for use.

EXAMPLE 15

Low Strength Granule

2-[[(4,6-dimethylpyrimidin-2-yl)aminocarbonyl-]aminosulfonyl]benzoic acid, 2-hydroxyethyl ester: 0.1%
attapulgite granules (U.S.S. 20–40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 16

Granule

'-[[(4,6-dimethylpyrimidin-2-yl)aminocarbonyl-]aminosulfonyl]benzoic acid, 2-hydroxyethyl ester: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 17

High Strength Concentrate

2-[[(4,6-dimethylpyrimidin-2-yl)aminocarbonyl-]aminosulfonyl]benzoic acid, 2-hydroxyethyl ester: 99%
silica aerogel: 0.5%
synthetic amorphous silica: 0.5%

The ingredients are blended and ground in a hammermill to produce a material essentially all passing a U.S.S. No. 50 screen (0.3 mm opening). The concentrate may be formulated further if necessary.

EXAMPLE 18

Wettable Powder

2-[[(4,6-dimethylpyrimidin-2-yl)aminocarbonyl-]aminosulfonyl]benzoic acid, 2-hydroxyethyl ester: 90%
dioctyl sodium sulfosuccinate: 0.1%
synthetic fine silica: 9.9%

The ingredients are blended and ground in a hammermill to produce particles essentially all below 100 microns. The material is sifted through a U.S.S. No. 50 screen and then packaged.

EXAMPLE 19

Wettable Powder

2-[[(4,6-dimethylpyrimidin-2-yl)aminocarbonyl-]aminosulfonyl]benzoic acid, 2-hydroxyethyl ester: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 20

Oil Suspension

2-[[(4,6-dimethylpyrimidin-2-yl)aminocarbonyl-]aminosulfonyl]benzoic acid, 2-hydroxyethyl ester: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

EXAMPLE 21

Dust

2-[[(4,6-dimethylpyrimidin-2-yl)aminocarbonyl-]aminosulfonyl]benzoic acid, 2-hydroxyethyl ester: 10%
attapulgite: 10%
Pyrophyllite: 80%

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulants. Many of them have utility for broad-spectrum pre- and/or postemergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Compounds

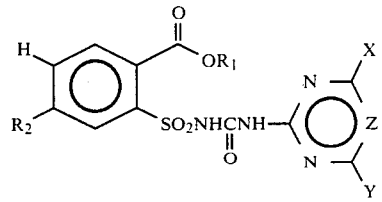

| Compound No. | $R_1$ | $R_2$ | X | Y | Z |
|---|---|---|---|---|---|
| 1 | $CH_2CH_2OH$ | H | $CH_3$ | $CH_3$ | CH |
| 2 | $CH_2CH_2OH$ | H | $OCH_3$ | $OCH_3$ | CH |
| 3 | $CH_2CH_2OH$ | H | Cl | $OCH_3$ | CH |
| 4 | $CH_2CH_2OH$ | H | $CH_3$ | $OCH_3$ | N |
| 5 | $CH_2CH_2OH$ | H | $OCH_3$ | $OCH_3$ | N |
| 6 | $CH_2CH_2OSO_2CH_3$ | H | $CH_3$ | $CH_3$ | CH |
| 7 | $CH_2CH_2OSO_2CH_3$ | H | $OCH_3$ | $OCH_3$ | CH |
| 8 | $CH_2CH_2OSO_2CH_3$ | H | Cl | $OCH_3$ | CH |
| 9 | $CH_2CH_2OSO_2CH_3$ | H | $CH_3$ | $OCH_3$ | N |
| 10 | $CH_2CH_2OSO_2CH_3$ | H | $OCH_3$ | $OCH_3$ | N |
| 11 | $CH_2CH_2CH_2OH$ | H | $CH_3$ | $CH_3$ | CH |
| 12 | $CH_2CH_2CH_2OH$ | H | $CH_3$ | $OCH_3$ | CH |
| 13 | $CH_2CH_2CH_2OH$ | H | $OCH_3$ | $OCH_3$ | CH |
| 14 | $CH_2CH_2CH_2OH$ | H | Cl | $OCH_3$ | CH |
| 15 | $CH_2CH_2CH_2OH$ | H | $CH_3$ | $CH_3$ | N |
| 16 | $CH_2CH_2CH_2OH$ | H | $CH_3$ | $OCH_3$ | N |
| 17 | $CH_2CH_2CH_2OH$ | H | $OCH_3$ | $OCH_3$ | N |
| 18 | $(CH_2)_3OSO_2CH_3$ | H | $CH_3$ | $CH_3$ | CH |

-continued
Compounds

| Compound No. | $R_1$ | $R_2$ | X | Y | Z |
|---|---|---|---|---|---|
| 19 | $(CH_2)_3OSO_2CH_3$ | H | $CH_3$ | $OCH_3$ | CH |
| 20 | $(CH_2)_3OSO_2CH_3$ | H | $OCH_3$ | $OCH_3$ | CH |
| 21 | $(CH_2)_3OSO_2CH_3$ | H | Cl | $OCH_3$ | CH |
| 22 | $(CH_2)_3OSO_2CH_3$ | H | $CH_3$ | $CH_3$ | N |
| 23 | $(CH_2)_3OSO_2CH_3$ | H | $CH_3$ | $OCH_3$ | N |
| 24 | $(CH_2)_3OSO_2CH_3$ | H | $OCH_3$ | $OCH_3$ | N |
| 25 | $CH_2CH_2OH$ | H | $CH_3$ | $CH_3$ | N |
| 26 | $CH_2CH_2OSO_2CH_3$ | H | $CH_3$ | $CH_3$ | N |
| 27 | $CH_2CH_2OC(O)CH_3$ | H | $CH_3$ | $CH_3$ | CH |
| 28 | $CH_2CH_2OC(O)CH_3$ | H | $CH_3$ | $OCH_3$ | CH |
| 29 | $CH_2CH_2OC(O)CH_3$ | H | $OCH_3$ | $OCH_3$ | CH |
| 30 | $CH_2CH_2OC(O)CH_3$ | H | $CH_3$ | $OCH_3$ | N |
| 31 | $CH_2CH_2OC(O)CH_3$ | H | $OCH_3$ | $OCH_3$ | N |
| 32 | $CH_2CH_2OSO_2-n-C_8H_{17}$ | H | $CH_3$ | $OCH_3$ | CH |
| 33 | $CH_2CH_2OSO_2-n-C_8H_{17}$ | H | $OCH_3$ | $OCH_3$ | CH |
| 34 | $CH_2CH_2OSO_2-n-C_8H_{17}$ | H | Cl | $OCH_3$ | CH |
| 35 | $CH_2CH_2OSO_2-n-C_8H_{17}$ | H | $CH_3$ | $OCH_3$ | N |
| 36 | $CH_2CH_2OSO_2-n-C_8H_{17}$ | H | $OCH_3$ | $OCH_3$ | N |
| 37 | $CH(CH_3)CH_2OSO_2CH_3$ | H | $OCH_3$ | $OCH_3$ | CH |
| 38 | $CH_2CH_2OC(O)NHA*$ | H | Cl | $OCH_3$ | CH |
| 39 | $CH_2CH(OH)CH_3$ | H | $CH_3$ | $CH_3$ | CH |
| 40 | $CH_2CH(OH)CH_3$ | H | $CH_3$ | $OCH_3$ | CH |
| 41 | $CH_2CH(OH)CH_3$ | H | $OCH_3$ | $OCH_3$ | CH |
| 42 | $CH_2CH(OH)CH_3$ | H | Cl | $OCH_3$ | CH |
| 43 | $CH_2CH(OH)CH_3$ | H | $CH_3$ | $OCH_3$ | N |
| 44 | $CH_2CH(OH)CH_3$ | H | $OCH_3$ | $OCH_3$ | N |
| 45 | $CH_2CH_2OH$ | Cl | $CH_3$ | $CH_3$ | CH |
| 46 | $CH_2CH_2OH$ | Cl | $CH_3$ | $OCH_3$ | CH |
| 47 | $CH_2CH_2OH$ | Cl | $OCH_3$ | $OCH_3$ | CH |
| 48 | $CH_2CH_2OH$ | Cl | Cl | $OCH_3$ | CH |
| 49 | $CH_2CH_2OH$ | Cl | $CH_3$ | $OCH_3$ | N |
| 50 | $CH_2CH_2OH$ | Cl | $OCH_3$ | $OCH_3$ | N |
| 51 | $CH_2CH_2OH$ | Cl | $OC_2H_5$ | $NHCH_3$ | N |
| 52 | $CH_2CH_2OH$ | H | $OC_2H_5$ | $NHCH_3$ | N |
| 53 | $CH_2CH_2OSO_2CH_3$ | H | $OC_2H_5$ | $NHCH_3$ | N |

*A is 4-chloro-6-methoxypyrimidin-2-yl

Test A

Seeds of crabgrass (Digitaria sp.), barnyardgrass (Echinochloa crusgalli), wild oats (Avena fatua), sicklepod (Cassia obtusifolia), morningglory (Ipomoea spp.), cocklebur (Xanthium Pensylvanicum), sorghum, corn, soybean, cotton, sugar beet, rice, wheat and purple nutsedge (Cyperus routundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to &=complete kill. The accompanying descriptive symbols have the following meanings:
B=burn;
C=chlorosis/necrosis;
D=defoliation;
E=emergence inhibition;
G=growth retardation;
H=formative effect;
U=unusual pigmentation;
X=axillary stimulation;
S=albiniusm; and
6Y=abscised buds or flowers.

TABLE A

| TYPE TEST | RATE K/HA | MORNING GLORY | COCKLE-BUR | VELVET-LEAF | NUT-SEDGE | CRAB GRASS | BARNYARD GRASS | CHEAT GRASS | WILD OATS | SICKLE POD | WHEAT | CORN | SOY-BEAN | RICE | SOR-GHUM | SUGARBEET | COTTON |
|---|---|---|---|---|---|---|---|---|---|---|---|---|---|---|---|---|---|
| Compound 1 |
| POST | 0.05 | 9C | 9C | | 7C 9G 8E | 2C 5G 3C 7G | 9C | | 2C 8G 2C 9G | 9C | 2C 8G 7C 9H | 3U 9G 9G | 3C 9G 9H | 7C 9G 8E | 3U 9G 8E | 3C 9H 5C 9G | 2C 9G |
| POST | 0.05 | | | | | | | | | | | | | | | | |
| PRE | 0.05 | 9G | 9H | | | | 4C 9H | | | 9G | | | | | | | 4C 9G |
| PRE | 0.05 | | | | | | | | | | | | | | | | |
| Compound 2 |
| POST | 0.05 | 8C | 9C | | 9C | 3C 8G 7G | 9C | | 3C 9G 4C 9G | 9C | 8C | 7U 9C 9G | 6C 9G 9H | 9C | 9C | 9C | 8C |
| POST | 0.05 | | | | | | | | | | | | | | | | |
| PRE | 0.05 | 9G | 9H | | 8E | | 5C 9H | | | 4C 9H | 5C 9H | | | 8E | 8H | 5C 9G | 8C |
| PRE | 0.05 | | | | | | | | | | | | | | | | |
| Compound 3 |
| POST | 0.05 | 4C 9G 9G | 9C | | 3C 9G 8E | 8G 2C | 9C | | 1C 2G 3C 8G | 3C 3H 5C 9G | 5G 3C 9G | 2C 7H 2U 9G | 5C 9G 4C 8G | 5C 9G 8E | 3C 9G 8H | 5C 9G 5C 9G | 5C 9G 9G |
| POST | 0.05 | | | | | | | | | | | | | | | | |
| PRE | 0.05 | | 9H | | | | 5C 9H | | | | | | | | | | |
| PRE | 0.05 | | | | | | | | | | | | | | | | |
| Compound 4 |
| POST | 0.05 | 2C 4H 3C 7G | 3C 5G 8H | | 2C 6G 3G | 1H 2G | 3C 9H 3C 3H | | 0 2C | 0 3C 8G | 2G 0 | 2G 0 | 3U 9G 2C 9G | 5C 9G 2C 3H | 4G 3C 6G | 3U 9G 3C 9H | 3C 6G 6G | 4C 7H 7G |
| POST | 0.05 | | | | | | | | | | | | | | | | |
| PRE | 0.05 | | | | | | | | | | | | | | | | |
| PRE | 0.05 | | | | | | | | | | | | | | | | |
| Compound 5 |
| POST | 0.05 | 2C 3G 3G | 2C 0 | | 3G 0 | 0 0 | 3C 9H 1C | | 0 0 | 1C 0 | 0 0 | 0 0 | 2U 9H 8G | 3C 9G 3H | 2G 2C | 3C 8G 2C 8H | 3C 4H 5G | 2C 5G 5G |
| POST | 0.05 | | | | | | | | | | | | | | | | |
| PRE | 0.05 | | | | | | | | | | | | | | | | |
| PRE | 0.05 | | | | | | | | | | | | | | | | |
| Compound 6 |
| POST | 0.05 | 6C 9G 9G | 6C 9G 8H | | 9C 9G | 3C 6G 5G | 9C | | 4C 9G 9G 3C 6G | 4C 8H 7G | 3C 9G 3C 9H | 2U 9H 3C 9G | 4C 9G 3C 7H | 9C | 5C 9G 5C 9H | 5C 9G 9G | 5C 9G 9G |
| POST | 0.05 | | | | | | | | | | | | | | | | |
| PRE | 0.05 | | | | | | | | | | | | | | | | |
| PRE | 0.05 | | | | | | | | | | | | | | | | |
| Compound 7 |
| POST | 0.05 | 9C | 9C | | 8C 8E | 3C 7G 7G | 9C | | 9C | 5C 9G | 4C 9G 5C 9H | 3U 9G 9G | 9C | 9C 8E | 3U 9G 8H | 9C | 9C |
| POST | 0.05 | | 9H | | | | 9H | | | | | | | | | | |
| PRE | 0.05 | 9H | | | | | | | | | | | | | | 8E | |
| PRE | 0.05 | | | | | | | | | | | | | | | | |
| Compound 8 |
| POST | 0.05 | 8C | 9C | | 3C 9G 8E | 4H 5G | 9H | | 6C 9G 2C 6G | 4C 6G 3C 6G | 7C 9G 2C 8G | 4H | 2C 8G 3C 7G | 5C 9G 8E | 4C 9G 8H | 3C 7G 4C 9G | 9C |
| POST | 0.05 | | 8H | | | | | | | | | | | | | | |
| PRE | 0.05 | 9G | | | | | 4C 9H | | | | | | | | | | |
| PRE | 0.05 | | | | | | | | | | | | | | | | |
| Compound 9 |
| POST | 0.05 | 2C 4H 7G | 9C 7H | | 0 0 | 2G 0 0 | 2C 7H 0 | | 7G 0 | 4C 8H 3C 6G | 6G 0 | 2C 9H 8G | 2C 8G 3H | 2G 2C | 3C 9H 2C 8H | 5C 9C 5C 9G | 4C 8H 7G |
| POST | 0.05 | | | | | | | | | | | | | | | | |
| PRE | 0.05 | | | | | | | | | | | | | | | | |
| PRE | 0.05 | | | | | | | | | | | | | | | | |
| Compound 10 |
| POST | 0.05 | 3C 6G | 4C 9G | | 3G | 0 | 3H | | 0 | 4C 8H | 0 | 3H | 2C 4G | 3G | 3H | 5C 9G | 4C 8G |
| POST | 0.05 | | | | | | | | | | | | | | | | |

TABLE A-continued

| TYPE TEST | RATE K/HA | MORNING GLORY | COCKLE-BUR | VELVET-LEAF | NUT-SEDGE | CRAB GRASS | BARNYARD GRASS | CHEAT GRASS | WILD OATS | SICKLE POD | WHEAT | CORN | SOY-BEAN | RICE | SOR-GHUM | SUGARBEET | COTTON |
|---|---|---|---|---|---|---|---|---|---|---|---|---|---|---|---|---|---|
| PRE | 0.05 | 8G | 8H | | | | | | | 7G | 0 | 3C/6C | 2C | 0 | 2C/6G | 5C/9G | 3C/7G |
| PRE | 0.05 | | | | | | | | | | | | | | | | |

Compound 11

| TYPE TEST | RATE | MG | CB | VL | NS | CG | BG | CHG | WO | SP | WH | CN | SB | RI | SO | SU | CT |
|---|---|---|---|---|---|---|---|---|---|---|---|---|---|---|---|---|---|
| POST | 0.05 | 2C/5H | 4C/9H/6H | | 2C/5G | 2G | 9H | 1C | | 2C | 8G | 3C/7H/3G | 4H | 4C/9G/3G | 3C/7H/4G | 3C/7H/4H | 2C/6G/5G |
| POST | 0.05 | 2G | 4C/9H/8H | | 3C/8G/5G | 0 | 1H | 0 | | 2G | 0 | 3C/7H/3G | 2G | 5C/9G/3C/8H | 3C/7H/2C/8G | 3C/7H/4H | 9C |
| PRE | 0.05 | 3C/7H/8G | | | | 3G | 9H | | 1C | 3C/5G/3C/7H | 3G | 3C/7H/2C/8G | 5C/9G/9H | 3C/9G/5G | 2C/7H/2C/8G | 3C/7H/8G | |
| PRE | 0.05 | 3G | 5C/9G/8H | | 3C/8G/0 | 3G | 9C | | 0 | 3C/7G/7G | 5G | 2C/5H/6G | 4C/8H/8H | 3C/9G/5G | 3C/8H/7G | 5G | 9G |

Compound 14 / 15 / 16 / 17

| TYPE TEST | RATE | MG | CB | VL | NS | CG | BG | CHG | WO | SP | WH | CN | SB | RI | SO | SU | CT |
|---|---|---|---|---|---|---|---|---|---|---|---|---|---|---|---|---|---|
| POST | 0.05 | 2G | 4C/9H/8H | | 0 | 0 | 9H | | 0 | 1C | 0 | 0 | 2H | 2C/6G | 1C/5G/3G | 0 | 5C/9G/6G |
| POST | 0.05 | 5G | 4C/9H/8H | | 0 | 0 | 3C/6G | | 0 | 3C/4G | 3G | 4G | 0 | 0 | 0 | 4G | 0 |
| PRE | 0.05 | 0 | 4C/9H/5G | | 0 | 0 | 2C/4H/0 | | 0 | 0 | 0 | 2G | 0 | 2G | 2G | 0 | 0 |
| PRE | 0.05 | 0 | 3C/9H/5H | | 0 | 0 | 3C/5H/0 | | 0 | 0 | 0 | 0 | 0 | 0 | 0 | 0 | 7G |
| POST | 0.05 | 0 | 2C/8H/4G | | 0 | 2G | 3C/5H | | 0 | 2C/3G/3H | 0 | 4G | 3H | 0 | 3G | 4C/9H/2C/5H | 0 |

Compound 18

| TYPE TEST | RATE | MG | CB | VL | NS | CG | BG | CHG | WO | SP | WH | CN | SB | RI | SO | SU | CT |
|---|---|---|---|---|---|---|---|---|---|---|---|---|---|---|---|---|---|
| POST | 0.05 | 2G | 5C/9G/3H | | 3C/8G/3G | 2G | 3C/8H/1H | 2C | 3C/8G/2C/4G | 3C/3G/1C | 8G | 1C/2H/2C/3G | 7H | 5C/9G/2C/4G | 4C/9G/3C/9H | 4C/8H/8E | 4C/9H/8G |
| POST | 0.05 | | | | | | | | 0 | | | | 2C | | | | |

Compound 19

| TYPE TEST | RATE | MG | CB | VL | NS | CG | BG | CHG | WO | SP | WH | CN | SB | RI | SO | SU | CT |
|---|---|---|---|---|---|---|---|---|---|---|---|---|---|---|---|---|---|
| POST | 0.05 | 3C/8H/2H | 8C | | 9G | 3C/5G/3C/7G | 3C/9H/4C/9H | 3C/8G/5C/9G | 3G | 4C/8H/4C/7G | 5G | 2C/3H/2C/7G | 9H | 5C/9G/5C/9H | 4C/9G/6C/9H | 9C | 9C |
| PRE | 0.05 | 9G | | | 2C/8G | | | 3C/9H | | | 6G | | 3C/6H | | | 4C/8H | 8G |

Compound 20

| TYPE TEST | RATE | MG | CB | VL | NS | CG | BG | CHG | WO | SP | WH | CN | SB | RI | SO | SU | CT |
|---|---|---|---|---|---|---|---|---|---|---|---|---|---|---|---|---|---|
| POST | 0.05 | 3C/8G/7G | 8C | | 5C/9G/5G | 2G/3G | 3C/9H/5H | 3C/7G/5G | 3G/5G | 3C/7H/5G | 3G/0 | 2G/6G | 3C/9G/6H | 5C/9G/2C | 3C/9H/3C | 4C/8H/9G | 9C/8G |
| PRE | 0.05 | | 7H | | | | | | | | | | | | | | |

TABLE A-continued

| TYPE TEST | RATE K/HA | MORNING GLORY | COCKLE-BUR | VELVET-LEAF | NUT-SEDGE | CRAB GRASS | BARNYARD GRASS | CHEAT GRASS | WILD OATS | SICKLE POD | WHEAT | CORN | SOY-BEAN | RICE | SOR-GHUM | SUGARBEET | COTTON |
|---|---|---|---|---|---|---|---|---|---|---|---|---|---|---|---|---|---|
| PRE | 0.05 | | | | | | | | | | | | | 6G | 9H | | |
| | | | | | | | | Compound 21 | | | | | | | | | |
| POST | 0.05 | 3C 5H | 9C | | 3C 6G 4G | 0 | 3C 7H 2G | 0 | 3G | 3C 3H 2G | 2G | 1C 3H 4G | 3G | 3C 8G 4G | 5C 9H 2C 9H | 3C 7H 8G | 5C 9G 6G |
| POST | 0.05 | 5G | 5H | | | 3G | | | 0 | 0 | 0 | 0 | 0 | 4G | | | |
| PRE | 0.05 | 0 | 0 | | 0 | 0 | 0 | 0 | 0 | 0 | 0 | 0 | 0 | 0 | 0 | 0 | 0 |
| PRE | 0.05 | 0 | 0 | | 0 | 0 | 0 | 0 | 0 | 0 | 0 | 0 | 0 | 0 | 0 | 0 | 0 |
| | | | | | | | | Compound 22 | | | | | | | | | |
| POST | 0.05 | 0 | 0 | | 0 | 0 | 0 | 0 | 0 | 0 | 0 | 0 | 0 | 0 | 0 | 0 | 0 |
| PRE | 0.05 | 0 | 0 | | 0 | 0 | 0 | 0 | 0 | 0 | 0 | 0 | 0 | 0 | 0 | 0 | 0 |
| | | | | | | | | Compound 23 | | | | | | | | | |
| POST | 0.05 | 3C 7G 2C | 4C 9G 2C 5H | | 0 | 0 | 0 | 3C 5G | 0 | 3C | 0 | 2G | 2C 6H | 0 | 3C 9H 3C 9H | 4C 9H 3C 3H | 4C 8H |
| POST | 0.05 | | | | | | | | | | | | | | | | 0 |
| PRE | 0.05 | | | | | | | | | | | | | | | | |
| PRE | 0.05 | | | | | | | | | | 0 | 2C 5G | 0 | 0 | | | |
| | | | | | | | | Compound 24 | | | | | | | | | |
| POST | 0.05 | 3C 5H 0 | 3C 9H 2C 2H | | 0 | 0 | 0 | 0 | 0 | 2C | 0 | 0 | 2C 5H | 0 | 3C 6H 0 | 3C 8H 0 | 6G 0 |
| PRE | 0.05 | | | | | | | | | | | | | | | | |
| | | | | | | | | Compound 25 | | | | | | | | | |
| POST | 0.05 | 8C 9G | 8C | | 5C 9G 8E | 1C 4G 0 | 9C | 5C 8G 4C 9G | 0 | 9C 3C 7H | 0 | 3H | | 5C 9G 5C 9G | 9H | 9C | 9C |
| POST | 0.05 | | | | | | | | | | 2G | 2C 8H | 3H | | 4C 9H | 9C | 9C |
| PRE | 0.05 | | | | | | | | | | | | | | | | |
| PRE | 0.05 | | | | | | | | | | | | | | | | |
| | | | | | | | | Compound 26 | | | | | | | | | |
| POST | 0.05 | 9C 9G | 8C 9H | | 4C 9G 8E | 5G 1C | 5C 9H 3C 9H | 3C 9G 4C 9H | 3C 6G 3C 9H | 3C 8H 2C 8H | 3G 6G | 2C 8H | 2C 5H | 5C 9G 8E | 2C 9G 5C 9H | 9C | 9C |
| POST | 0.05 | | | | | | | | | | | 3C 9H 9G | 5C 9G 6H | | | | |
| PRE | 0.05 | | | | | | | | | | | | | | | | |
| PRE | 0.05 | | | | | | | | | | | | | | | | |
| | | | | | | | | Compound 27 | | | | | | | | | |
| POST | 0.05 | 6C 9G 9G | 5C 9G 9H | | 5C 9G 3C 9G | 3C 8G 2C 4G | 9C 4C 9H | 2C 8G 3C 7G | 2C 8G 6G 3C 9H | 6C 9G 3C 9G | 2C 9G 3C 9G | 3C 9H 5C 9H | 5C 9G 6C 9G 4C 8H | 5C 9G 9C | 5C 9H 5C 9H | 5C 9G 5C 9G | 9C |
| POST | 0.05 | | | | | | | | | | | | | | | | |
| PRE | 0.05 | | | | | | | | | | | | | | | | |
| PRE | 0.05 | | | | | | | | | | | | | | | | |
| | | | | | | | | Compound 28 | | | | | | | | | |
| POST | 0.05 | 8C 9G | 8C 9G | | 6C 9G 8E | 3C 6G 3C 7G | 9C 5C 9H | 2C 8G 3C 6G 3C 9H | 2C 9G 3C 9G | 9C 4C 9G | 2C 9G 3C 9G | 3C 9H 5C 9H | 6C 9G 4C 8H | 5C 9G 9C | 5C 9H 5C 9H | 5C 9G 9C | 9C |
| POST | 0.05 | | | | | | | | | | | 3C 9H | 9H | 8E | 3C 9H | | 9C |
| PRE | 0.05 | | | | | | | | | | | | | | | | |
| PRE | 0.05 | | | | | | | | | | | | | | | | |
| | | | | | | | | Compound 29 | | | | | | | | | |
| POST | 0.05 | 8C 9G | 8C 9H | | 9C 8E | 3C 9G 7G | 8C 5C 9H | | 2C 9G 0 | 8C 3G 0 | 9C 5C 9H | 2C 9G 9H | 4C 9H | 8E | 3C 9G 6C 9H | 6C 9G 9C | 3C 9G 3C 9G |
| POST | 0.05 | 9G | 9H | | | | | | | | | 5C 9H | | | | | |
| PRE | 0.05 | | | | | | | | | | | | | | | | |
| PRE | 0.05 | | | | | | | | | | | | | | | | |
| | | | | | | | | Compound 30 | | | | | | | | | |
| POST | 0.05 | 2C 4H 2C | 2C 4G 2C | | 0 | 2G 0 | 3C 8H 2G | 0 | 0 | 3G 0 | 0 | 4C 9H 2C | 4C 8H 2C | 2C 5G 5G | 3C 9H 3C | 3C 4G 5G | 5C 9H 5G |
| POST | 0.05 | | | | | | | | | | | | | | | | |
| PRE | 0.05 | | | | | | | | | | | | | | | | |
| PRE | 0.05 | | | | | | | | | | | | | | | | |

TABLE A-continued

| TYPE TEST | RATE K/HA | MORNING GLORY | COCKLE-BUR | VELVET-LEAF | NUT-SEDGE | CRAB GRASS | BARNYARD GRASS | CHEAT GRASS | WILD OATS | SICKLE POD | WHEAT | CORN | SOY-BEAN | RICE | SOR-GHUM | SUGARBEET | COTTON |
|---|---|---|---|---|---|---|---|---|---|---|---|---|---|---|---|---|---|
| | | | | | | | | Compound 31 | | | | | | | | | |
| PRE | 0.05 | | | | | | | | 0 | | 0 | 9G | 3H | | 9G | | |
| POST | 0.05 | 3C | 3G | | 0 | 0 | 2C | | | | | 2C | 2C | 2C | 3C | 4C | 3C |
| POST | 0.05 | 5G | 8G | | 0 | 0 | 8H | | 0 | 4G | 0 | 6H | 5H | 4G | 8G | 5H | 6G |
| PRE | 0.05 | 3C | | | | | 2C | | | | 0 | 2C | 5H | 2C | 2C | 2C | 5G |
| PRE | 0.05 | 5G | | | | | | | | | | 8G | | | 5G | 5G | |
| | | | | | | | | Compound 32 | | | | | | | | | |
| POST | 0.05 | 8C | 9C | 9C | 4C | 3C | 9C | 8C | 3C | | 2C | 6C | 2C | 9C | 9C | 8C | 5C |
| POST | 0.05 | | | | 8G | 3G | | | 8G | | 8G | 9H | 5H | | 8G | | 9G |
| PRE | 0.05 | 5C | 9H | 5C | 8E | 2C | 4C | 8E | 3C | | 3C | 4C | 4C | 8E | 5C | 5C | 9G |
| PRE | 0.05 | 9H | | 9G | | 3G | 9H | | 9G | | 9G | 9G | 8G | | 9H | 9G | |
| | | | | | | | | Compound 33 | | | | | | | | | |
| POST | 0.05 | 8C | 8C | 8C | 9C | 3C | 9C | 8C | 2C | | 2C | 8C | 8C | 9C | 8C | 8C | 9C |
| POST | 0.05 | | | | | 6G | | | 9G | | 8G | 9G | 8G | | | | |
| PRE | 0.05 | 9G | 9H | 5C | 8E | 2C | 3C | 9H | 3C | | 2C | 2C | 2C | 8E | 3C | 9C | 9C |
| PRE | 0.05 | | | 9G | | 5G | 9H | | 8G | | 8G | 9G | 8G | | 9H | | |
| | | | | | | | | Compound 34 | | | | | | | | | |
| POST | 0.05 | 8C | 4C | 3C | 4C | 0 | 5C | 4C | 2C | | 2C | 2C | 5C | 4C | 3C | 9C | 4C |
| POST | 0.05 | 8G | 9G | 7G | 9G | 0 | 9H | 8G | 3G | | 4C | 6H | 9H | 9G | 9H | 5C | 9G |
| PRE | 0.05 | | 8H | 8G | 8G | | 3C | 7G | 3G | | 2C | 7G | 2C | 9G | 3C | 5G | 8G |
| PRE | 0.05 | | | | | | 7G | | | | 5G | | 6G | | 9H | | |
| | | | | | | | | Compound 35 | | | | | | | | | |
| POST | 0.05 | 4C | 8C | 4C | 0 | 0 | 0 | 4G | 0 | | 0 | 3C | 2C | 0 | 3C | 8C | 4C |
| POST | 0.05 | 8G | 6H | 8G | 0 | 0 | 0 | 2G | 0 | | 0 | 8H | 8G | 2C | 9H | 5C | 9H |
| PRE | 0.05 | 7G | | | | | | | | | | 3C | 4H | | 3C | 9G | 8G |
| PRE | 0.05 | | | | | | | | | | | 8H | | | 9H | | |
| | | | | | | | | Compound 36 | | | | | | | | | |
| POST | 0.05 | 3C | 8C | 4C | 2C | 0 | 0 | 0 | 0 | | 0 | 2H | 4H | 0 | 0 | 3C | 3C |
| POST | 0.05 | 8G | 5G | 8G | 0 | 0 | 0 | | 0 | | | | | | 3G | 9H | 7G |
| PRE | 0.05 | 8G | | 0 | | 0 | | | | | 0 | 2C | 1C | 0 | | 9C | 6G |
| PRE | 0.05 | | | | | | | | | | | 4G | | | | | |
| | | | | | | | | Compound 37 | | | | | | | | | |
| POST | 0.05 | 3C | 8C | 9C | 4C | 3G | 9C | 8G | 4C | | 5C | 3C | 4C | 9C | 3C | 4C | 5C |
| POST | 0.05 | 7G | 9H | 5C | 9G | 0 | 5C | 5C | 8G | | 9H | 9H | 9G | 5C | 9H | 8H | 9G |
| PRE | 0.05 | 8G | | 9G | 8E | | 9H | 9G | 4C | | 4C | 3C | 3C | 9G | 5C | 4C | 9G |
| PRE | 0.05 | | | | | | | | 9G | | 9H | 8H | 9H | | | 8G | |
| | | | | | | | | Compound 38 | | | | | | | | | |
| POST | 0.05 | 3C | 9C | 5C | 4C | 0 | 3C | 2C | 0 | | 0 | 3C | 4C | 4C | 4C | 3C | 5C |
| POST | 0.05 | 7H | 8H | 9G | 9G | 2G | 9H | 4G | 0 | | | 7G | 8G | 8G | 7C | 9H | 9G |
| PRE | 0.05 | 9G | | 7G | 8G | | 3C | 0 | | | 4G | 3C | 3C | 4C | 9H | 4C | 3C |
| PRE | 0.05 | | | | | | 8H | | | | | 7G | 6H | 9H | | 8G | 8G |
| | | | | | | | | Compound 39 | | | | | | | | | |
| POST | 0.05 | 3C | 8C | 2C | 2C | 2C | 5C | 2C | 0 | | 0 | 2U | 5C | 6C | 4C | 8C | 4C |
| POST | 0.05 | 8G | 9H | 9G | 9G | 0 | 9H | 9G | 2C | | | 9C | 9G | 9G | 8G | | 8H |
| PRE | 0.05 | 7G | | 3C | 6G | 2C | 7H | 7G | 5G | | 3G | 3C | 2C | 9H | 9H | 5C | 2C |
| PRE | 0.05 | | | 5H | | | | | | | | 8H | 6G | | | 9G | 6H |
| | | | | | | | | Compound 40 | | | | | | | | | |
| POST | 0.05 | 9C | 9C | 9C | 2C | 3G | 9C | 8G | 2C | | 8G | 3U | 5C | 6C | 6C | 9C | 8C |

TABLE A-continued

| TYPE TEST | RATE K/HA | MORNING GLORY | COCKLE-BUR | VELVET-LEAF | NUT-SEDGE | CRAB GRASS | BARNYARD GRASS | CHEAT GRASS | WILD OATS | SICKLE POD | WHEAT | CORN | SOY-BEAN | RICE | SOR-GHUM | SUGARBEET | COTTON |
|---|---|---|---|---|---|---|---|---|---|---|---|---|---|---|---|---|---|
| POST | 0.05 | | 9H | 2C 8G | 9G 8E | 2G | 4C 9H | 9H | 5G 3C 8H | | 2C 9H | 9G 2C 9H | 9G 9H | 9G 8E | 9G 9H | 5C 9G | 3C 9G |
| PRE | 0.05 | 9G | | | | | | | | | | | | | | | |
| PRE | 0.05 | | | | | | | | | | | | | | | | |
| POST | 0.05 | 8C | 8C | 8C | 8C | 5G | 9C | 3C 9G 9H | 2C 6G 4C 8G | | 7G | 8C | 9C | 5C 9G 8E | 4C 9G 8H | 8C | 8C |
| PRE | 0.05 | | | | | | | | | | | | | | | | |
| PRE | 0.05 | 9G | | 9G | 8E | 0 | 5C 9H | | | | 2C 9H | 2C 9H | 9H | | 4C 9G | 4C 9H 3C 8G | 9G |
| | | | | | | | | Compound 41 | | | | | | | | | |
| POST | 0.05 | 2C 9H 7G | 9C 8H | 2C 8G 5G | 8G 8E | 0 | 9H | 3G | 0 | | 0 | 1H 5G 4G | 2C 9G 2H | 5C 9G 9H | 5C 9G 3C 8H | 4C 9H 3C 8G | 9C 8G |
| PRE | 0.05 | | | | | | | | | | | | | | | | |
| PRE | 0.05 | | | | | | | | 2G | | 5G | | | | | | |
| | | | | | | | | Compound 42 | | | | | | | | | |
| POST | 0.05 | 2C 6H 3H | 3C 8H 2H | 2C 6G 0 | 2C 8G 0 | 0 | 3C 0 | 1C 0 | 0 | | 0 | 9C | 4C 8H 5H | 4G | 3C 9G 3C 8H | 3C 8H 8G | 2C 3G 0 |
| PRE | 0.05 | | | | | | | | | | | | | | | | |
| PRE | 0.05 | | | | | | | | | | | | | | | | |
| | | | | | | | | Compound 43 | | | | | | | | | |
| POST | 0.05 | 2C 5H 0 | 2C 5G 4H | 2G 3G | 7G 0 | 0 | 2H 0 | 0 | 0 | | 0 | 8H 5G | 3H 7G 2G | 0 | 2C 6G 2C 5G | 2C 6H 0 | 0 |
| PRE | 0.05 | | | | | | | | | | | | | | | | |
| PRE | 0.05 | | | | | | | | | | | | | | | | |
| | | | | | | | | Compound 44 | | | | | | | | | |
| POST | 0.05 | 2C 6H 8G | 9C 9H | 9C 8H | 2C 8G 5G | 4G 2G | 9C 8H | 3C 8G | 0 8G 2G | | 2C 7G | 9C 5G 9G | 9C 7H | 2C 2C 8G | 3C 5G 3C 9H | 3H 9H 7G | 9C 8G |
| PRE | 0.05 | | | | | | | | | | | | | | | | |
| PRE | 0.05 | | | | | | | | | | | | | | | | |
| | | | | | | | | Compound 45 | | | | | | | | | |
| POST | 0.05 | 6C 9G 9G | 8C 9H | 8C 4C 9G | 3C 8G 3C 9G | 5G 3G | 9C 5C 9H | 7G | 0 8G | | 5G 3C 9G | 9C 3C 9H | 9C 8H | 5C 9G 8E | 4C 9H 3C 9H | 3C 5H 4C 9G | 8C 2C 8G |
| PRE | 0.05 | | | | | | | | | | | | | | | | |
| PRE | 0.05 | | | | | | | | | | | | | | | | |
| | | | | | | | | Compound 46 | | | | | | | | | |
| POST | 0.05 | 5C 9G 9G | 9C 9H | 8C 8C | 4C 4C 9G 9G | 3G 2C 3G | 9C 3C 9H | 6G | 0 2G | | 3C 9G 8G | 5C 9G 3C 9H | 9C 9H | 4C 9G 4C 9H | 3C 9H 2C 9H | 2C 6G 8G | 9C 4C 9G |
| PRE | 0.05 | | | | | | | | | | | | | | | | |
| PRE | 0.05 | | | | | | | | | | | | | | | | |
| | | | | | | | | Compound 47 | | | | | | | | | |
| POST | 0.05 | 5C 9G 5G | 9C 8G 0 | 4C 8G 8G | 2C 7G 0 | 0 | 4C 9H 3G | 8G | 0 1C | | 0 4G | 0 7G | 5C 9G 2H | 2C 8G 7H | 4C 9H 3C 7G | 1C 5G | 4C 9G 6G |
| PRE | 0.05 | | | | | | | | | | | | | | | | |
| PRE | 0.05 | | | | | | | | | | | | | | | | |
| | | | | | | | | Compound 48 | | | | | | | | | |
| POST | 0.05 | 4G 4H | 4C 9H 0 | 2G 0 | 0 0 | 0 0 | 6C 9H 3C 6G | 5G 5G | 2G 2C 8G | | 5G 5G | 5C 9G 3C 9G | 3C 7G 3H | 3C 7G 3C 6H | 3C 8H 2C 7G | 2C 3G 0 | 0 0 |
| PRE | 0.05 | | | | | | | | | | | | | | | | |
| PRE | 0.05 | | | | | | | | | | | | | | | | |
| | | | | | | | | Compound 49 | | | | | | | | | |

TABLE A-continued

| TYPE TEST | RATE K/HA | MORNING GLORY | COCKLE-BUR | VELVET-LEAF | NUT-SEDGE | CRAB GRASS | BARNYARD GRASS | CHEAT GRASS | WILD OATS | SICKLE POD | WHEAT | CORN | SOY-BEAN | RICE | SOR-GHUM | SUGARBEET | COTTON |
|---|---|---|---|---|---|---|---|---|---|---|---|---|---|---|---|---|---|
| | | | | | | | | Compound 50 | | | | | | | | | |
| POST | 0.05 | 0 | 4H | 0 | 0 | 0 | 4C | 4G | 0 | | 0 | 3C | 3C | 4C | 1C | 3C | 0 |
| POST | 0.05 | | | | | | 9H | | | | | 9H | 6H | 9G | | 5H | |
| PRE | 0.05 | 0 | 2H | 4H | 0 | 0 | 0 | 4G | 2C | | 5G | 3C | 2G | 3C | 3C | 6G | 2G |
| PRE | 0.05 | | | | | | | | 6G | | | 8G | | 8H | 8G | | |
| | | | | | | | | Compound 51 | | | | | | | | | |
| POST | 0.05 | 2C | 8G | 3C | 5G | 2G | 5C | 3G | 0 | | 0 | 3C | 3C | 5C | 3C | 2C | 2C |
| POST | 0.05 | 8G | | 7G | | | 9H | | | | | 9H | 9H | 9G | 7H | 2H | |
| PRE | 0.05 | 6G | 7G | 7G | 0 | 4G | 2C | 8G | 2C | | 8G | 3C | 5H | 3C | 3C | 3G | 2G |
| PRE | 0.05 | | | | | | 8G | | 8G | | | 8G | | 8H | 7G | | |
| | | | | | | | | Compound 52 | | | | | | | | | |
| POST | 0.05 | 3C | 4C | 4C | 2C | 3G | 5C | 3C | 6G | | 2G | 5C | 9C | 9C | 5C | 9C | 5C |
| POST | 0.05 | 8H | 9G | 9G | 5G | | 9H | 8G | | | | 9G | | | 9G | | 9G |
| PRE | 0.05 | 9C | 8G | 9G | 5G | 6G | 9H | 9H | 9G | | 8G | 9G | 9H | 9H | 9H | 5C | 9G |
| PRE | 0.05 | | | | | | | | | | | | | | | 9G | |
| | | | | | | | | Compound 53 | | | | | | | | | |
| POST | 0.05 | 4C | 3C | 4C | 0 | 3G | 5C | 4C | 9G | | 0 | 3U | 5C | 9C | 4C | 9C | 4C |
| POST | 0.05 | 8H | 6G | 8H | | | 9H | 9G | | | | 9G | 9G | | 9H | | 9G |
| PRE | 0.05 | 9G | 8H | 3C | 5G | 3G | 9H | 9H | 3C | | 2G | 9G | 3C | 4C | 3C | 5C | 2C |
| PRE | 0.05 | | | 7G | | | | | 8G | | | | 7H | 9H | 9H | 9G | 9G |

What is claimed is:
1. A compound of the formula :

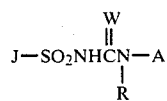

wherein
J is

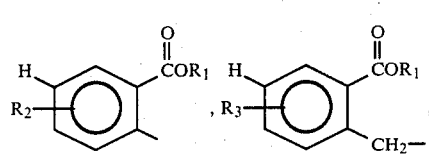

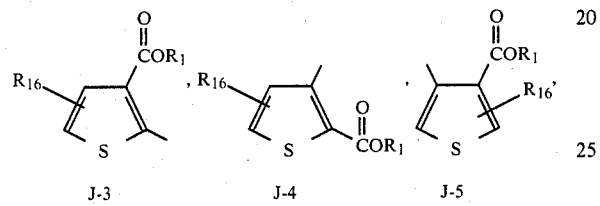

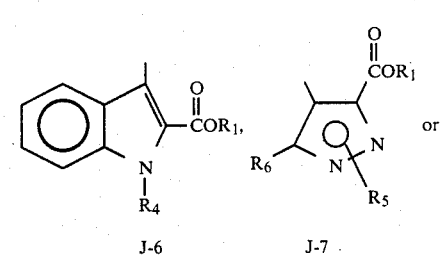

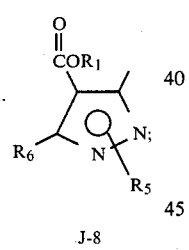

W is O or S;
R is H or CH$_3$;
R$_1$ is C$_2$–C$_5$ alkyl, C$_4$ akenyl or C$_4$ alkynyl substituted with one or two substituents selected from:

—OH, —SH, —OCR$_{17}$(=W$_1$), —SCR$_{17}$(=O), —OCOR$_{17}$(=W$_1$), —SCOR$_{17}$(=O),

—OCNR$_8$R$_{17}$(=W$_1$), —SCNR$_8$R$_{17}$(=O), —OCNH$_2$(=W$_1$), —SCNH$_2$(=O),

—OCNR$_8$A(=W$_1$), —OP(OR$_{10}$)$_2$(=W$_1$), —SP(OR$_{10}$)$_2$(=W$_1$), —OSO$_2$R$_{17}$,

—OSO$_2$NR$_8$R$_{17}$, —OSi(R$_9$)$_2$R$_{10}$, —NR$_7$R$_8$, or —OCF$_2$H;

provided that
(1) when R$_1$ is disubstituted, then the two substituents are identical and are not on the same carbon atom; and (2) the carbon atom of R$_1$ adjacent to the ester oxygen does not carry any of the above substituents and must be substituted by at least one hydrogen atom;
W$_1$ is O or S;
R$_2$ is H, Cl, F, Br, C$_1$–C$_3$ alkyl, C$_1$–C$_3$ alkoxy, C$_1$–C$_3$ alkylthio, C$_1$–C$_3$ haloalkoxy, C$_1$–C$_3$ haloalkylthio, C$_1$–C$_2$ haloalkyl, or C$_1$–C$_2$ alkyl substituted with OCH$_3$ or SCH$_3$;
R$_3$ is H, F, Cl, CH$_3$ or OCH$_3$;
R$_4$ is H or CH$_3$;
R$_5$ is H, C$_1$–C$_3$ alkyl, CH$_2$CH=CH$_2$ or phenyl;
R$_6$ is H or C$_1$–C$_3$ alkyl;
R$_8$ is H or C$_1$–C$_2$ alkyl;
R$_9$ is C$_1$–C$_2$ alkyl;
R$_{10}$ is C$_1$–C$_4$ alkyl or C$_6$H$_5$;
A is

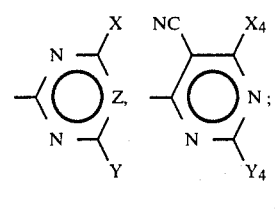

X is CH$_3$, OCH$_3$, OCH$_2$CH$_3$, Cl, F, Br, OCF$_2$H, CH$_2$F, OCH$_2$CH$_2$F, OCH$_2$CHF$_2$, OCH$_2$CF$_3$ or CF$_3$;
Y is H, CH$_3$, OCH$_3$, OC$_2$H$_5$, CH$_2$OCH$_3$, NHCH$_3$, N(OCH$_3$)CH$_3$, NH$_2$, N(CH$_3$)$_2$, C$_2$H$_5$, CF$_3$, SCH$_3$, OCH$_2$CH=CH$_2$, OCH$_2$C≡CH, OCH$_2$CH$_2$OCH$_3$,

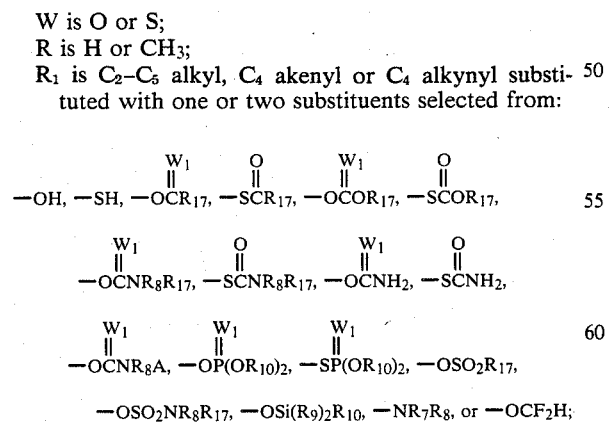

OCF$_2$H, SCF$_2$H, CH$_2$S(O)$_p$(C$_1$–C$_4$ alkyl), cyclopropyl or CH$_2$OC$_2$H$_5$;
m is 2 or 3;
p is 0, 1 or 2;
Q$_1$ and Q$_2$ are independently O or S;
R$_{13}$ is H or CH$_3$;
R$_{14}$ and R$_{15}$ are independently C$_1$–C$_2$ alkyl;
R$_{16}$ is H, F, Cl or CH$_3$;
R$_{17}$ is C$_1$–C$_{10}$ alkyl substituted with 0–3 atoms of F, Cl or Br, 0–2 methoxy groups or 0–1 cyano groups, C$_3$–C$_{10}$ alkenyl substituted with 0–3 atoms of F, Cl or Br, C$_3$–C$_{10}$ alkynyl substituted with 0–3 atoms of F, Cl or Br, or

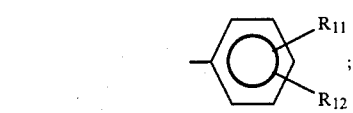

Z is CH;
X$_4$ is CH$_3$, OCH$_3$, OC$_2$H$_5$, CH$_2$OCH$_3$ or Cl; and
Y$_4$ is CH$_3$, OCH$_3$, OC$_2$H$_5$ or Cl;
provided that
(a) when W is S, then R is H. A is

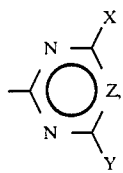

and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CF_3$, $OCH_2CH_2OCH_3$, $CH(OCH_3)_2$ or

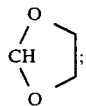

(b) when X is Cl, F or Br, then Y is $OCH_3$, $OC_2H_5$, $NH_2$, $N(OCH_3)CH_3$, $NHCH_3$, $N(CH_3)_2$ or $OCF_2H$;

and their agriculturally suitable salts.

2. A compound of claim 1 wherein W is O; R is H; $R_1$ is monosubstituted $C_2$–$C_5$ alkyl; $R_7$ is $CH_3$, $C_2H_5$, $C_3$ alkenyl or $C_3$ alkynyl; $R_9$ is $CH_3$; $R_{10}$ is $CH_3$; and $R_{17}$ is $C_1$–$C_4$ alkyl substituted with 0–3 atoms of F, Cl or Br, 0–2 methoxy groups or 0–1 cyano group, $C_3$–$C_4$ alkenyl substituted with 0–3 atoms of F, Cl or Br or $C_3$–$C_4$ alkynyl.

3. A compound of claim 2 wherein A is A-1; $R_2$ is H, F, Cl, $CH_3$, $OCH_3$, $OC_2H_5$, $SCH_3$, $SC_2H_5$, $CH_2OCH_3$ or $CF_3$; $R_6$ is H; $R_{16}$ is H; and Y is $CH_3$, $C_2H_5$, $OCH_3$, $OC_2H_5$, $CH_2OCH_3$, $CH_2OC_2H_5$, $NHCH_3$, $N(CH_3)_2$, cyclopropyl, $CH(OCH_3)_2$ or

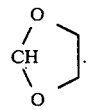

4. A compound of claim 3 wherein $R_{17}$ is $CH_3$, $C_2H_5$ or $CH_2CH=CH_2$; $W_1$ is O; and $R_1$ is monosubstituted $C_2$–$C_3$ alkyl.

5. A compound of claim 4 wherein J is J-1 and $R_2$ is H.

6. A compound of claim 4 wherein J is J-2.
7. A compound of claim 4 wherein J is J-3.
8. A compound of claim 4 wherein J is J-4.
9. A compound of claim 4 wherein J is J-5.
10. A compound of claim 4 wherein J is J-6.
11. A compound of claim 4 wherein J is J-7.
12. A compound of claim 4 wherein J is J-8.
13. A compound of claim 4 wherein X is $CH_3$, $OCH_3$, $OC_2H_5$, Cl, Br, $OCHF_2$ or $CF_3$; and Y is $CH_3$, $OCH_3$, $NHCH_3$ or $CH(OCH_3)_2$.

14. A compound of claim 1 which is 2-[[(4,6-dimethylpyrimidin-2-yl)-aminocarbonyl]aminosulfonyl]benzoic acid, 2-hydroxyethyl ester.

15. A composition suitable for controlling the growth of undesired vegetation which comprises an effective amount of a compound of claim 1 and at least one of the following: surfactant, solid or liquid diluent.

16. A composition suitable for controlling the growth of undesired vegetation which comprises an effective amount of a compound of claim 2 and at least one of the following: surfactant, solid or liquid diluent.

17. A composition suitable for controlling the growth of undesired vegetation which comprises an effective amount of a compound of claim 3 and at least one of the following: surfactant, solid or liquid diluent.

18. A composition suitable for controlling the growth of undesired vegetation which comprises an effective amount of a compound of claim 4 and at least one of the following: surfactant, solid or liquid diluent.

19. A composition suitable for controlling the growth of undesired vegetation which comprises an effective amount of a compound of claim 5 and at least one of the following: surfactant, solid or liquid diluent.

20. A composition suitable for controlling the growth of undesired vegetation which comprises an effective amount of a compound of claim 6 and at least one of the following: surfactant, solid or liquid diluent.

21. A composition suitable for controlling the growth of undesired vegetation which comprises an effective amount of a compound of claim 7 and at least one of the following: surfactant, solid or liquid diluent.

22. A composition suitable for controlling the growth of undesired vegetation which comprises an effective amount of a compound of claim 8 and at least one of the following: surfactant, solid or liquid diluent.

23. A method for controlling the growth of undesired vegetation which comprises applying to the locus to be protected an effective amount of a compound of claim 1.

24. A method for controlling the growth of undesired vegetation which comprises applying to the locus to be protected an effective amount of a compound of claim 2.

25. A method for controlling the growth of undesired vegetation which comprises applying to the locus to be protected an effective amount of a compound of claim 3.

26. A method for controlling the growth of undesired vegetation which comprises applying to the locus to be protected an effective amount of a compound of claim 4.

27. A method for controlling the growth of undesired vegetation which comprises applying to the locus to be protected an effective amount of a compound of claim 5.

28. A method for controlling the growth of undesired vegetation which comprises applying to the locus to be protected an effective amount of a compound of claim 6.

29. A method for controlling the growth of undesired vegetation which comprises applying to the locus to be protected an effective amount of a compound of claim 7.

30. A method for controlling the growth of undesired vegetation which comprises applying to the locus to be protected an effective amount of a compound of claim 8.

* * * * *

UNITED STATES PATENT AND TRADEMARK OFFICE
CERTIFICATE OF CORRECTION

PATENT NO. : 4,661,147
DATED : April 28, 1987
INVENTOR(S) : Donald J. Dumas

It is certified that error appears in the above—identified patent and that said Letters Patent is hereby corrected as shown below:

Column 70, after line 13 add:

"$R_7$ is $C_1$-$C_4$ alkyl substituted with 0-3 atoms of F, Cl or Br, 0-2 methoxy groups or 0-1 cyano groups, $C_3$-$C_4$ alkenyl substituted with 0-3 atoms of F, Cl, or Br, $C_3$-$C_4$ alkynyl or 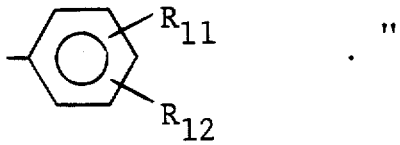 ."

Column 70, after line 16 add:

"$R_{11}$ and $R_{12}$ are independently H, F, Cl, Br, $CH_3$, $OCH_3$, $SCH_3$, $SO_2CH_3$, $NO_2$ or $CF_3$."

UNITED STATES PATENT AND TRADEMARK OFFICE
CERTIFICATE OF CORRECTION

PATENT NO. : 4,661,147
DATED : April 28, 1987
INVENTOR(S) : Donald J. Dumas

It is certified that error appears in the above-identified patent and that said Letters Patent is hereby corrected as shown below:

Column 70 -

In the definition of A, after A-1 add "or" and identify the structural formula next to A-1 as A-7.

Signed and Sealed this

Fifth Day of January, 1988

Attest:

DONALD J. QUIGG

Attesting Officer

Commissioner of Patents and Trademarks